US009198952B2

(12) United States Patent
Alvarez et al.

(10) Patent No.: US 9,198,952 B2
(45) Date of Patent: Dec. 1, 2015

(54) COMPOSITIONS OF AND METHODS OF USING LIGAND DIMERS

(75) Inventors: Luis M. Alvarez, Cambridge, MA (US); Linda G. Griffith, Cambridge, MA (US); Richard T. Lee, Weston, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 279 days.

(21) Appl. No.: 13/120,184

(22) PCT Filed: Sep. 22, 2009

(86) PCT No.: PCT/US2009/005252
§ 371 (c)(1),
(2), (4) Date: Nov. 7, 2011

(87) PCT Pub. No.: WO2010/033249
PCT Pub. Date: Mar. 25, 2010

(65) Prior Publication Data
US 2012/0040900 A1 Feb. 16, 2012

Related U.S. Application Data

(60) Provisional application No. 61/192,945, filed on Sep. 22, 2008.

(51) Int. Cl.
C07K 16/44 (2006.01)
G01N 33/573 (2006.01)
A61K 38/18 (2006.01)
C07K 14/475 (2006.01)
C07K 14/78 (2006.01)

(52) U.S. Cl.
CPC ......... *A61K 38/1808* (2013.01); *A61K 38/1841* (2013.01); *C07K 14/475* (2013.01); *C07K 14/78* (2013.01); *C07K 2319/70* (2013.01); *C07K 2319/73* (2013.01); *C07K 2319/74* (2013.01)

(58) Field of Classification Search
None
See application file for complete search history.

(56) References Cited

U.S. PATENT DOCUMENTS

| 5,218,093 | A | | 6/1993 | Guo et al. |
|---|---|---|---|---|
| 5,580,726 | A | | 12/1996 | Villeponteau et al. |
| 5,763,584 | A | * | 6/1998 | Godowski ............... 530/402 |
| 6,004,555 | A | | 12/1999 | Thorpe et al. |
| 6,127,337 | A | | 10/2000 | Konishi et al. |
| 6,500,934 | B1 | | 12/2002 | Lerner et al. |
| 6,635,249 | B1 | | 10/2003 | Marchionni et al. |
| 2002/0002276 | A1 | | 1/2002 | Fitzpatrick et al. |
| 2003/0087306 | A1 | | 5/2003 | Christensen et al. |
| 2003/0186868 | A1 | | 10/2003 | Rosenbaum et al. |
| 2003/0190702 | A1 | | 10/2003 | Maihle et al. |
| 2003/0207391 | A1 | | 11/2003 | Pappa |
| 2005/0036984 | A1 | | 2/2005 | Harrison et al. |
| 2006/0019888 | A1 | | 1/2006 | Zhou |
| 2006/0183194 | A1 | | 8/2006 | Ballinger et al. |
| 2006/0183887 | A1 | | 8/2006 | Jakobovits et al. |
| 2006/0228357 | A1 | | 10/2006 | Chang et al. |
| 2007/0009972 | A1 | | 1/2007 | Chao et al. |
| 2007/0092528 | A1 | | 4/2007 | Sun |
| 2007/0117755 | A1 | | 5/2007 | Liang |
| 2007/0154994 | A1 | | 7/2007 | De Crescenzo et al. |
| 2007/0196379 | A1 | | 8/2007 | Marchionni et al. |
| 2013/0196911 | A1 | | 8/2013 | Jay et al. |

FOREIGN PATENT DOCUMENTS

| WO | WO 93/23550 A2 | 11/1993 |
|---|---|---|
| WO | WO 95/25166 A1 | 9/1995 |
| WO | WO 98/02540 A2 | 1/1998 |
| WO | WO 00/64400 A2 | 11/2000 |
| WO | WO 01/90192 A2 | 11/2001 |
| WO | WO 02/051869 A1 | 7/2002 |
| WO | WO 02/102854 A2 | 12/2002 |
| WO | WO 02/102972 A2 | 12/2002 |
| WO | WO 02/102973 A2 | 12/2002 |
| WO | WO 03/012045 A2 | 2/2003 |
| WO | WO 03/014159 A1 | 2/2003 |
| WO | WO 03/099300 A1 | 12/2003 |
| WO | WO 2004/087766 A2 | 10/2004 |
| WO | WO 2004/112717 A2 | 12/2004 |
| WO | WO 2007/046893 A2 | 4/2007 |
| WO | WO 2007/066106 A1 | 6/2007 |
| WO | WO 2007/066109 A1 | 6/2007 |
| WO | WO 2007/146959 A2 | 12/2007 |
| WO | WO 2008/140814 A1 | 11/2008 |
| WO | WO 2010/033249 A2 | 3/2010 |

OTHER PUBLICATIONS

Witton et al., Expression of the HER1-4 family of receptor tyrosine kinases in breast cancer, Mar. 31, 2003, Journal of Pathology 200:290-297.*
Zaczek et al., The diverse signaling network of EGFR, HER2, HER3 and HER4 tyrosine kinase receptors and the consequences for therapeutic approaches, 2005, Histol Histopathol 20: 1005-1015.*
Guillemard et al., HER2-Mediated Internalization of a Targeted Prodrug Cytotoxic Conjugate is Dependent on the Valency of the Targeting Ligand, 2005, DNA and Cell Biology 24(6):350-358.*
Extended European Search Report for Application No. 11760220.1 mailed Dec. 13, 2013.

(Continued)

*Primary Examiner* — John Ulm
(74) *Attorney, Agent, or Firm* — Wolf, Greenfield & Sacks, P.C.

(57) ABSTRACT

Provided herein are ligand dimers, compositions thereof, as well as methods of their use. The ligand dimers provided can comprise at least one ligand to a Her receptor and can be used to force dimerization of specific receptor pairs. The forced dimerization of specific receptor pairs can be used to control (e.g., promote or inhibit) signaling, and, therefore, the ligand dimers provided can also be used in various forms of treatment in which such signaling control is beneficial to a subject. It follows that methods for controlling signaling are provided as are various methods of treatment.

16 Claims, 53 Drawing Sheets

(56) References Cited

OTHER PUBLICATIONS

Invitation to Pay Additional Fees for Application No. PCT/US2011/029799 mailed Jun. 16, 2011.
International Search Report and Written Opinion for Application No. PCT/US2011/029799 mailed Aug. 18, 2011.
International Preliminary Report on Patentability for Application No. PCT/US2011/029799 mailed Oct. 4, 2012.
International Search Report and Written Opinion for Application No. PCT/US2009/005252 mailed Jun. 14, 2010.
International Preliminary Report on Patentability for Application No. PCT/US2009/005252 mailed Mar. 31, 2011.
Alvarez, Modulating Cell Behavior With Engineered Bivalent HER-Receptor Ligands. Thesis sumitted to the Department of Biological Engineering on Aug. 24, 2009 in Partial Fulfillment of the Requirements for the Degree of Doctor of Philosophy in Biological Engineering at Massachusetts Institute of Technology. 130 pages.
Arteaga et al., Unliganded epidermal growth factor receptor dimerization induced by direct interaction of quinazolines with the ATP binding site. J Biol Chem. Sep. 12, 1997;272(37):23247-54.
Bazley et al., The epidermal growth factor receptor family. Endocr Relat Cancer. Jul. 2005;12 Suppl 1:S17-27.
Bersell et al., Neuregulin1/ErbB4 signaling induces cardiomyocyte proliferation and repair of heart injury. Cell. Jul. 23, 2009;138(2):257-70. doi: 10.1016/j.cell.2009.04.060.
Bian et al., Neuregulin-1 attenuated doxorubicin-induced decrease in cardiac troponins. Am J Physiol Heart Circ Physiol. Dec. 2009;297(6):H1974-83. Epub Oct. 2, 2009.
Chen et al., Transmembrane domain sequence requirements for activation of the p185c-neu receptor tyrosine kinase. J Cell Biol. May 5, 1997;137(3):619-31.
Comoglio et al., Interactions between growth factor receptors and adhesion molecules: breaking the rules. Curr Opin Cell Biol. Oct. 2003;15(5):565-71.
Crone et al., ErbB2 is essential in the prevention of dilated cardiomyopathy. Nat Med. May 2002;8(5):459-65.
Davis et al., Local myocardial insulin-like growth factor 1 (IGF-1) delivery with biotinylated peptide nanofibers improves cell therapy for myocardial infarction. Proc Natl Acad Sci U S A. May 23, 2006;103(21):8155-60. Epub May 12, 2006.
Fan et al., Antibody-induced epidermal growth factor receptor dimerization mediates inhibition of autocrine proliferation of A431 squamous carcinoma cells. J Biol Chem. Nov. 4, 1994;269(44):27595-602.
Fan et al., Regulation of epidermal growth factor receptor in NIH3T3/HER14 cells by antireceptor monoclonal antibodies. J Biol Chem. Oct. 5, 1993;268(28):21073-9.
Fan et al., Tethered epidermal growth factor provides a survival advantage to mesenchymal stem cells. Stem Cells. May 2007;25(5):1241-51. Epub Jan. 18, 2007.
Faress et al., Bleomycin-induced pulmonary fibrosis is attenuated by a monoclonal antibody targeting HER2. J Appl Physiol (1985). Dec. 2007;103(6):2077-83. Epub Oct. 4, 2007.
Ferguson et al., Ligand-induced conformational changes in the epidermal growth factor receptor. FASEB Journal. ASBMB Annual Meeting and 8$^{th}$ IUBMB Conference. Boston, Massachusetts. Jun. 12-16, 2004. Abstract 103.2, p. C228.
Fukazawa et al., Neuregulin-1 protects ventricular myocytes from anthracycline-induced apoptosis via erbB4-dependent activation of PI3-kinase/Akt. J Mol Cell Cardiol. Dec. 2003;35(12):1473-9.
Guillemard et al., HER2-mediated internalization of a targeted prodrug cytotoxic conjugate is dependent on the valency of the targeting ligand. DNA Cell Biol. Jun. 2005;24(6):350-8.
Hsieh et al., Controlled delivery of PDGF-BB for myocardial protection using injectable self-assembling peptide nanofibers. J Clin Invest. Jan. 2006;116(1):237-48. Epub Dec. 15, 2005.
Hsieh et al., Local controlled intramyocardial delivery of platelet-derived growth factor improves postinfarction ventricular function without pulmonary toxicity. Circulation. Aug. 15, 2006;114(7):637-44. Epub Aug. 7, 2006.

Hynes, Integrins: bidirectional, allosteric signaling machines. Cell. Sep. 20, 2002;110(6):673-87.
Jay et al., An engineered bivalent neuregulin protects against doxorubicin-induced cardiotoxicity with reduced proneoplastic potential. Circulation. Jul. 9, 2013;128(2):152-61. Doi:10.1161/CIRCULATIONAHA.113.002203. Epub Jun. 11, 2013.
Jay et al., Engineered bivalent ligands to bias ErbB receptor-mediated signaling and phenotypes. J Biol Chem. Aug. 5, 2011;286(31):27729-40. Doi: 10.1074/jbc.M111.221093. Epub May 26, 2011.
Jay et al., Supplemental Data to Engineered bivalent ligands to bias ErbB receptor-mediated signaling and phenotypes. J Biol Chem. Aug. 5, 2011;286(31):27729-40. Doi: 10.1074/jbc.M111.221093. Epub May 26, 2011.
Jones et al., Binding specificities and affinities of egf domains for ErbB receptors. FEBS Lett. Mar. 26, 1999;447(2-3):227-31.
Knowlden et al., Elevated levels of epidermal growth factor receptor/c-erbB2 heterodimers mediate an autocrine growth regulatory pathway in tamoxifen-resistant MCF-7 cells. Endocrinology. Mar. 2003;144(3):1032-44.
Kühn et al., Periostin induces proliferation of differentiated cardiomyocytes and promotes cardiac repair. Nat Med. Aug. 2007;13(8):962-9. Epub Jul. 15, 2007.
Kumagai et al., Role of extracellular subdomains of p185c-neu and the epidermal growth factor receptor in ligand-independent association and transactivation. Proc Natl Acad Sci U S A. Aug. 5, 2003;100(16):9220-5. Epub Jul. 16, 2003.
Kuramochi et al., Neuregulin activates erbB2-dependent src/FAK signaling and cytoskeletal remodeling in isolated adult rat cardiac myocytes. J Mol Cell Cardiol. Aug. 2006;41(2):228-35.
Langenickel et al., Forced homodimerization by site-directed mutagenesis alters guanylyl cyclase activity of natriuretic peptide receptor B. Hypertension. Feb. 2004;43(2):460-5. Epub Dec. 22, 2003.
Liotta et al., Cancer metastasis and angiogenesis: an imbalance of positive and negative regulation. Cell. Jan. 25, 1991;64(2):327-36.
Liu et al., Neuregulin-1/erbB-activation improves cardiac function and survival in models of ischemic, dilated, and viral cardiomyopathy. J Am Coll Cardiol. Oct. 3, 2006;48(7):1438-47. Epub Sep. 14, 2006.
Maradia et al., Pharmacologic prevention of anthracycline-induced cardiomyopathy. Cardiol Rev. Sep.-Oct. 2009;17(5):243-52. doi: 10.1097/CRD.0b013e3181b8e4c8. Erratum in Cardiol Rev. Nov.-Dec. 2009;17(6):299.
Martin et al., Rebuilt AAA + motors reveal operating principles for ATP-fuelled machines. Nature. Oct. 20, 2005;437(7062):1115-20.
Menendez et al., Targeting human epidermal growth factor receptor 2: it is time to kill kinase death human epidermal growth factor receptor 3. J Clin Oncol. Jun. 10, 2007;25(17):2496-8; author reply 2499.
Moll et al., Designed heterodimerizing leucine zippers with a ranger of pIs and stabilities up to 10(-15) M. Protein Sci. Mar. 2001;10(3):649-55.
Montero et al., Neuregulins and cancer. Clin Cancer Res. Jun. 1, 2008;14(11):3237-41.
Muthuswamy et al., ErbB2, but not ErbB1, reinitiates proliferation and induces luminal repopulation in epithelial acini. Nat Cell Biol. Sep. 2001;3(9):785-92.
Muthuswamy et al, Controlled dimerization of ErbB receptors provides evidence for differential signaling by homo- and heterodimers. Mol Cell Biol. Oct. 1999;19(10):6845-57.
Nakaji-Hirabayashi et al., Surface-anchoring of spontaneously dimerized epidermal growth factor for highly selective expansion of neural stem cells. Bioconjug Chem. Jan. 2009;20(1):102-10. Doi: 10.1021/bc800331t.
Ogiso et al., Crystal structure of the complex of human epidermal growth factor and receptor extracellular domains. Cell. Sep. 20, 2002;110(6):775-87.
Otto et al., Cell proliferation through forced engagement of c-Kit and Flt-3. Blood. Jun. 1, 2001;97(11):3662-4.
Park et al., PEGylated PLGA nanoparticles for the improved delivery of doxorubicin. Nanomedicine. Dec. 2009;5(4):410-8. doi: 10.1016/j.nano.2009.02.002. Epub Mar. 31, 2009.

(56) References Cited

OTHER PUBLICATIONS

Qazi et al., Ligand-independent homo- and heterodimerization of human prolactin receptor variants: inhibitory action of the short forms by heterodimerization. Mol Endocrinol. Aug. 2006;20(8):1912-23. Epub Mar. 23, 2006.
Rahman et al., Doxorubicin-induced chronic cardiotoxicity and its protection by liposomal administration. Cancer Res. May 1982;42(5):1817-25.
Rayson et al., Anthracycline-trastuzumab regimens for HER2/neu-overexpressing breast cancer: current experience and future strategies. Ann Oncol. Sep. 2008;19(9):1530-9. doi: 10.1093/annonc/mdn292. Epub May 13, 2008.
Sawyer et al., Modulation of anthracycline-induced myofibrillar disarray in rat ventricular myocytes by neuregulin-1beta and anti-erbB2: potential mechanism for trastuzumab-induced cardiotoxicity. Circulation. Apr. 2, 2002;105(13):1551-4
Segers et al., Local delivery of protease-resistant stromal cell derived factor-1 for stem cell recruitment after myocardial infarction. Circulation. Oct. 9, 2007;116(15):1683-92. Epub Sep. 17, 2007.
Shi et al., Study of inhibition effect of herceptin on interaction between heregulin and erbB receptors HER3/HER2 by single-molecule force spectroscopy. Exp Cell Res. Oct. 1, 2009;315(16):2847-55. doi: 10.1016/j.yexcr.2009.05.023. Epub Jun. 1, 2009. Abstract Only.
Spaargaren et al., Antibody-induced dimerization activates the epidermal growth factor receptor tyrosine kinase. J Biol Chem. Jan. 25, 1991;266(3):1733-9.
Sternsdorf et al., Forced retinoic acid receptor alpha homodimers prime mice for APL-like leukemia. Cancer Cell. Feb. 2006;9(2):81-94.
Stuhlmann-Laeisz et al., Forced dimerization of gp130 leads to constitutive STAT3 activation, cytokine-independent growth, and blockade of differentiation of embryonic stem cells. Mol Biol Cell. Jul. 2006;17(7):2986-95. Epub Apr. 19, 2006.
Surette et al., Role of alpha-helical coiled-coil interactions in receptor dimerization, signaling, and adaptation during bacterial chemotaxis. J Biol Chem. Jul. 26, 1996;271(30):17966-73.
Tamama et al., Epidermal growth factor as a candidate for ex vivo expansion of bone marrow-derived mesenchymal stem cells. Stem Cells. Mar. 2006;24(3):686-95. Epub Sep. 8, 2005.
Tzahar et al., Bivalence of EGF-like ligands drives the ErbB signaling network. EMBO J. Aug. 15, 1997; 16(16): 4938-4950. doi: 10.1093/emboj/16.16.
Wiley, Trafficking of the ErbB receptors and its influence on signaling. Exp Cell Res. Mar. 10, 2003;284(1):78-88.
Witton et al., Expression of the HER1-4 family of receptor tyrosine kinases in breast cancer. J Pathol. Jul. 2003;200(3):290-7.
Wouters et al., Protecting against anthracycline-induced myocardial damage: a review of the most promising strategies. Br J Haematol. Dec. 2005;131(5):561-78.
Xu et al., Neuregulin-1/ErbB signaling: a druggable target for treating heart failure. Curr Opin Pharmacol. Apr. 2009;9(2):214-9. Epub Dec. 11, 2008.
Yarden et al., Untangling the ErbB signalling network. Nat Rev Mol Cell Biol. Feb. 2001;2(2):127-37.
Zaczek et al., The diverse signaling network of EGFR, HER2, HER3 and HER4 tyrosine kinase receptors and the consequences for therapeutic approaches. Histol Histopathol. Jul. 2005;20(3):1005-15.
Zhan et al., Controlled activation of ErbB1/ErbB2 heterodimers promote invasion of three-dimensional organized epithelia in an ErbB1-dependent manner: implications for progression of ErbB2-overexpressing tumors. Cancer Res. May 15, 2006;66(10):5201-8.

* cited by examiner

SEQUENCE LISTING

```
<160> NUMBER OF SEQ ID NOS: 5

<210> SEQ ID NO 1
<211> LENGTH: 7
<212> TYPE: PRT
<213> ORGANISM: artificial sequence
<220> FEATURE:
<223> OTHER INFORMATION: synthetic polypeptide

<400> SEQUENCE: 1

Lys Val Gly Phe Phe Lys Arg
1               5

<210> SEQ ID NO 2
<211> LENGTH: 6
<212> TYPE: PRT
<213> ORGANISM: artificial sequence
<220> FEATURE:
<223> OTHER INFORMATION: synthetic polypeptide

<400> SEQUENCE: 2

Gly Arg Gly Asp Ser Pro
1               5

<210> SEQ ID NO 3
<211> LENGTH: 7
<212> TYPE: PRT
<213> ORGANISM: artificial sequence
<220> FEATURE:
<223> OTHER INFORMATION: synthetic polypeptide

<400> SEQUENCE: 3

Ser Val Val Tyr Gly Leu Arg
1               5

<210> SEQ ID NO 4
<211> LENGTH: 47
<212> TYPE: PRT
<213> ORGANISM: artificial sequence
<220> FEATURE:
<223> OTHER INFORMATION: synthetic peptide, EE1234L

<400> SEQUENCE: 4

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr Gly Pro Leu Gly Gly Gly Lys
        35                  40                  45

<210> SEQ ID NO 5
<211> LENGTH: 47
<212> TYPE: PRT
<213> ORGANISM: artificial sequence
<220> FEATURE:
<223> OTHER INFORMATION: synthetic polypeptide, RR1234L

<400> SEQUENCE: 5

Lys Gly Gly Gly Leu Glu Ile Arg Ala Ala Phe Leu Arg Arg Arg Asn
1               5                   10                  15

Thr Ala Leu Arg Thr Arg Val Ala Glu Leu Arg Gln Arg Val Gln Arg
            20                  25                  30

Leu Arg Asn Ile Val Ser Gln Tyr Glu Thr Arg Tyr Gly Pro Leu
        35                  40                  45
```

COMPOSITIONS OF AND METHODS OF USING LIGAND DIMERS

RELATED APPLICATIONS

This application claims the benefit under 35 U.S.C. §119 (e) from U.S. provisional application Ser. No. 61/192,945, filed Sep. 22, 2008, the entire contents of which are herein incorporated by reference.

GOVERNMENT SUPPORT

This invention has been made using funding from National Institutes of Health grant numbers EB003805 and GM059870. The government has certain rights in the invention.

SUMMARY OF THE INVENTION

In one aspect a method of controlling Her receptor dimerization is provided. In one embodiment the method comprises the step of contacting cells that express at least one type of Her receptor with one or more types of ligand dimers in an amount effective to cause the dimerization of one or more specific receptor pairs, wherein at least one of the receptors of the one or more specific receptor pairs is a Her receptor.

In one embodiment of the methods provided one specific receptor pair is Her-1-Her-1. In another embodiment one specific receptor pair is Her-1-Her-3. In still another embodiment one specific receptor pair is Her-1-Her-4. In a further embodiment one specific receptor pair is Her-3-Her-3. In yet another embodiment, one specific receptor pair is Her-3-Her-4. In still another embodiment one specific receptor pair is Her-4-Her-4.

In one embodiment of the methods provided the cells also express at least one type of integrin. In one embodiment one specific receptor pair is a Her receptor and an integrin. In another embodiment the Her receptor is Her-1, Her-2, Her-3 or Her-4. In yet another embodiment the integrin is $\alpha v\beta 3$. In still another embodiment the integrin is $\alpha 5\beta 1$.

In another embodiment of the methods provided the cells express at least two types of Her receptors. In one embodiment the at least two types of Her receptors include Her-2 and at least one other type of Her receptor, and wherein at least one type of ligand dimer is contacted with the cells in an amount effective to cause dimerization of the at least one other type of Her receptor but not with Her-2. In one embodiment Her-2 is left without another type of Her receptor with which to pair and Her-2 signaling is inhibited. It is not a requirement of this embodiment, however, that all of the Her-2 receptors on the cells are left without another receptor with which to pair. Instead what is required is that more Her-2 receptors are left without another receptor with which to pair as compared to the number of such Her-2 receptors in the absence of contact with the one or more ligand dimers. In one embodiment, enough of the Her-2 receptors are left without another receptor with which to pair to elicit the desired biological result.

In one embodiment the at least one other type of Her receptor includes Her-3. In one embodiment the at least one type of ligand dimer causes Her-3 homodimerization. In still another embodiment the at least one other type of Her receptor includes Her-3 and Her-1. In one embodiment the at least one type of ligand dimer includes a ligand dimer that causes Her-3 homodimerization, a ligand dimer that causes Her-1 homodimerization, a ligand dimer that causes Her-1-Her-3 heterodimerization or some combination thereof. In yet another embodiment at least one other type of Her receptor includes Her-3 and Her-4. In one embodiment the at least one type of ligand dimer includes a ligand dimer that causes Her-3 homodimerization, a ligand dimer that causes Her-4 homodimerization, a ligand dimer that causes Her-3-Her-4 heterodimerization or some combination thereof. In a further embodiment the at least one other type of Her receptor includes Her-3, Her-1 and Her-4. In one embodiment the at least one type of ligand dimer includes a ligand dimer that causes Her-3 homodimerization, a ligand dimer that causes Her-1 homodimerization, a ligand dimer that causes Her-4 homodimerization, a ligand dimer that causes Her-3-Her-1 heterodimerization, a ligand dimer that causes Her-3-Her-4 heterodimerization, a ligand dimer that causes Her-1-Her-4 heterodimerization or some combination thereof. In another embodiment the at least one other type of Her receptor includes Her-1, and wherein the at least one type of ligand dimer causes Her-1 homodimerization. In a further embodiment the at least one other type of Her receptor includes Her-1 and Her-4. In one embodiment the at least one type of ligand dimer includes a ligand dimer that causes Her-1 homodimerization, a ligand dimer that causes Her-4 homodimerization, a ligand dimer that causes Her-1-Her-4 heterodimerization or some combination thereof. In another embodiment the at least one other type of Her receptor includes Her-4. In one embodiment the at least one type of ligand dimer causes Her-4 homodimerization.

In one embodiment the cells express Her-1, Her-2 and at least one other type of Her receptor. In another embodiment the at least one type of ligand dimer causes dimerization of the at least one other type of Her receptor but not with Her-1 or Her-2. In one embodiment the at least one other type of Her receptor is Her-3. In another embodiment the at least one type of ligand dimer causes Her-3 homodimerization. In one embodiment the at least one other type of Her receptor is Her-3 and Her-4. In another embodiment the at least one type of ligand dimer includes a ligand dimer that causes Her-3 homodimerization, a ligand dimer that causes Her-4 homodimerization, a ligand dimer that cases Her-3-Her-4 heterodimerization or some combination thereof. In one embodiment Her-1-Her-2 receptor signaling is promoted. It is not a requirement of this embodiment, however, that all of the Her-1 and/or Her-2 receptors on the cells are can dimerize with each other as a result of this method. Instead what is required is that more Her-1 and/or Her-2 receptors can dimerize with each other as compared to the number of such receptors in the absence of contact with the one or more ligand dimers. In one embodiment, enough of the Her-1 and/or Her-2 receptors can dimerize each other in order to elicit the desired biological result. In one embodiment the Her-1-Her-2 receptor signaling is promoted in an amount effective for tissue or cell regeneration.

In another embodiment the cells express at least two types of Her receptors and at least one type of integrin. In one embodiment at least one type of ligand dimer is contacted with the cells in an amount effective to cause dimerization of one of the at least two types of Her receptors and one type of integrin. In one embodiment the Her receptor is Her-1. In another embodiment the integrin is $\alpha v\beta 3$. In yet another embodiment the integrin is $\alpha 5\beta 1$. In still another embodiment the at least two types of Her receptors include Her-2 and at least one other type of Her receptor. In one embodiment at least one other type of ligand dimer is contacted with the cells in an amount effective to cause dimerization of the at least one other type of Her receptor but not with Her-2. In another embodiment Her-2 is left without another type of Her receptor with which to pair and Her-2 signaling is inhibited. It is not a requirement of this embodiment, however, that all of the Her-2 receptors on the cells are left without another receptor with which to pair. Instead what is required is that more Her-2 receptors are left without another receptor with which to pair as compared to the number of such Her-2 receptors in the absence of contact with the one or more ligand dimers. In one embodiment, enough of the Her-2 receptors are left without another receptor with which to pair to elicit the desired biological result.

In still another embodiment the at least one other type of Her receptor includes Her-3. In one embodiment at least one other type of ligand dimer is contacted with the cells at least one of which causes Her-3 homodimerization. In a further embodiment the at least one other type of Her receptor includes Her-3 and Her-1. In one embodiment at least one other type of ligand dimer is contacted with the cells and includes a ligand dimer that causes Her-3 homodimerization, a ligand dimer that causes Her-1 homodimerization, a ligand dimer that causes Her-1-Her-3 heterodimerization or some combination thereof. In still a further embodiment the at least one other type of Her receptor includes Her-3 and Her-4. In one embodiment at least one other type of ligand dimer is contacted with the cells and includes a ligand dimer that causes Her-3 homodimerization, a ligand dimer that causes Her-4 homodimerization, a ligand dimer that causes Her-3-Her-4 heterodimerization or some combination thereof. In yet another embodiment the at least one other type of Her receptor includes Her-3, Her-1 and Her-4. In one embodiment at least one other type of ligand dimer is contacted with the cells and includes a ligand dimer that causes Her-3 homodimerization, a ligand dimer that causes Her-1 homodimerization, a ligand dimer that causes Her-4 homodimerization, a ligand dimer that causes Her-3-Her-1 heterodimerization, a ligand dimer that causes Her-3-Her-4 heterodimerization, a ligand dimer that causes Her-1-Her-4 heterodimerization or some combination thereof. In another embodiment the at least one other type of Her receptor includes Her-1. In one embodiment at least one other type of ligand dimer is contacted with the cells and includes a ligand dimer that causes Her-1 homodimerization. In yet another embodiment the at least one other type of Her receptor includes Her-1 and Her-4. In one embodiment at least one other type of ligand dimer is contacted with the cells and includes a ligand dimer that causes Her-1 homodimerization, a ligand dimer that causes Her-4 homodimerization, a ligand dimer that causes Her-1-Her-4 heterodimerization or some combination thereof. In another embodiment the at least one other type of Her receptor includes Her-4. In one embodiment at least one other type of ligand dimer is contacted with the cells and causes Her-4 homodimerization.

In yet another embodiment the cells express Her-1, Her-2, at least one other type of Her receptor, and at least one type of integrin. In one embodiment one of the at least one type of ligand dimer causes dimerization of one of the at least one other type of Her receptor and one type of integrin. In one embodiment the integrin is $\alpha v \beta 3$. In another embodiment the integrin is $\alpha 5 \beta 1$. In a further embodiment at least one other type of ligand dimer is contacted with the cells in an amount effective to cause dimerization of one of the at least one type of Her receptor but not with Her-1 or Her-2. In one embodiment Her-1-Her-2 receptor signaling is promoted. It is not a requirement of this embodiment, however, that all of the Her-1 and/or Her-2 receptors on the cells can dimerize with each other as a result of this method. Instead what is required is that more Her-1 and/or Her-2 receptors can dimerize with each other as compared to the number of such receptors in the absence of contact with the one or more ligand dimers. In one embodiment, enough of the Her-1 and/or Her-2 receptors can dimerize each other in order to elicit the desired biological result. In one embodiment the Her-1-Her-2 receptor signaling is promoted in an amount effective for regeneration.

In one embodiment the at least one other type of Her receptor is Her-3. In one embodiment the at least one other type of ligand dimer causes Her-3 homodimerization. In another embodiment the at least one other type of Her receptor is Her-3 and Her-4. In one embodiment the at least one other type of ligand dimer includes a ligand dimer that causes Her-3 homodimerization, a ligand dimer that causes Her-4 homodimerization, a ligand dimer that cases Her-3-Her-4 heterodimerization or some combination thereof.

In one embodiment of the methods provided herein the method is for promoting signaling of a specific receptor pair. In another embodiment of the methods provided the method is for inhibiting the signaling of a specific receptor pair.

In one embodiment of the methods provided herein the method is for promoting cell proliferation, differentiation, migration, survival or some combination thereof. In another embodiment of the methods provided herein the method is for inhibiting cell proliferation, differentiation, migration, survival or some combination thereof. In still another embodiment of the methods provided herein the method is for promoting cell death.

In one embodiment of the methods provided the methods are for treating cancer. Such methods in another embodiment comprise the step of contacting a cancerous tissue or cells with one or more ligand dimers. In a further embodiment the cancerous tissue or cells are contacted with another anti-cancer agent. In yet another embodiment of such methods one or more ligand dimers is administered to a subject that has cancer. In another embodiment another anti-cancer agent is administered to the subject. In one embodiment of the methods provided the cells are cells of a cancer or tumor. In another embodiment the cells are lung cancer cells.

In one embodiment of the methods provided the methods are for promoting tissue or cell regeneration. Such methods in another embodiment comprise the step of contacting a tissue or cells with one or more ligand dimers. In a further embodiments the tissue or cells are contacted with another wound healing agent. In yet another embodiment of such methods one or more ligand dimers is administered to a subject in need thereof. In another embodiment another wound healing agent is administered to the subject.

In one embodiment of the methods provided the cells are of the central nervous system or a wound. In another embodiment the cells are glial cells. In yet another embodiment the cells are cells associated with angiogenesis. In one embodiment the cells are endothelial cells or fibroblasts. In still another embodiment the cells are MSCs. In yet another embodiment the cells are any of the cells described herein, including HeLa and MCF-7 cells.

In one embodiment of the methods provided the methods are for treating a neurological disorder/disease. Such methods in another embodiment comprise the step of contacting a tissue or cells with one or more ligand dimers. In a further embodiments the tissue or cells are contacted with another agent for treating the neurological disorder/disease. In yet another embodiment of such methods one or more ligand dimers is administered to a subject that has a neurological disorder/disease. In another embodiment another agent for treating the neurological disorder/disease is administered to the subject.

Compositions comprising one or more ligand dimers, and in some embodiments for use in any of the methods provided herein, are also provided.

In another aspect a ligand dimer is provided. In one embodiment the ligand dimer comprises two ligands, at least one of which is a Her ligand. In another embodiment the ligand dimer also comprises a linker. In a further embodiment the ligand dimer causes dimerization of one or more specific receptor pairs. In one embodiment at least one of the receptors of the receptor pair is a Her receptor.

In one embodiment each of the two ligands is a Her ligand. In one embodiment the ligand dimer causes dimerization of one or more specific Her receptor pairs.

In another embodiment one of the two ligands is an integrin ligand. In one embodiment the ligand dimer causes dimerization of one or more specific Her-integrin receptor pairs. In one embodiment the integrin is αvβ3. In another embodiment the integrin is α5β1.

In one embodiment the linker comprises a coiled coil domain. In another embodiment the linker further comprises peptide spacers. In yet another embodiment the peptide spacer is a 20 amino acid peptide.

In a further embodiment the linker comprises a water soluble flexible polymer that covalently links the two ligands, e.g., two Her ligands. In one embodiment the water soluble flexible polymer is polyethylene oxide (PEO), dextran, polyacrylic acid, or polyacrylamide.

In another embodiment the ligands are to the same Her receptor. In yet another embodiment the ligands are not to the same Her receptor.

In one embodiment one or both of the ligands is a Her-1 ligand. In another embodiment the Her-1 ligand is transforming growth factor-alpha (TGF-α), epidermal growth factor (EGF), epiregulin, β-cellulin, heparin-binding epidermal-like growth factor (HB-EGF) or amphiregulin.

In another embodiment one or both of the ligands is a Her-3 ligand. In one embodiment the Her-3 ligand is neuregulin-1α, neuregulin-1β, heregulin-4 or betacellulin.

In yet another embodiment one or both of the ligands is a Her-4 ligand. In one embodiment the Her-4 ligand is epiregulin, HB-EGF, neuregulin-1α, neuregulin-1β, neuregulin-3 or neuregulin-4.

In one embodiment of any of the ligand dimers provided the ligands are the same. In another embodiment of any of ligand dimers provided the ligands are not the same.

In another embodiment at least one of the ligands of the ligand dimer comprises a detectable label. In one embodiment the label can be a chromophore, fluorophore or radioisotope. In still another embodiment the at least one of the ligands of the ligand dimer comprises biotin or a biotin acceptor peptide. In yet another embodiment at least one of the ligands of the ligand dimer comprises an antibody-detectable epitope. In one embodiment the ligand dimer can be attached to a substrate via the biotin or biotin acceptor peptide or antibody-detectable epitope.

In a further aspect compositions comprising any one or more of the ligand dimers provided are provided. In yet another aspect a composition comprising any one or more of the ligand dimers provided, wherein the ligand dimers are attached to a substrate, is provided. In one embodiment the substrate is an extracellular matrix. In another embodiment the substrate is a tissue engineering scaffold.

In still another aspect a composition comprising any one or more of the ligand dimers provided, wherein the composition further comprises a pharmaceutically acceptable carrier, is provided.

In still a further aspect the compositions provided herein further comprise an additional therapeutic agent. In one embodiment the additional therapeutic agent is an anti-cancer agent. In another embodiment the additional therapeutic agent is an agent for treating a neurological disorder. In still another embodiment the additional therapeutic agent is a wound healing agent.

In another aspect a method of treating cancer in a subject is provided, wherein the method comprises administering to a subject that has cancer any one or more of the ligand dimers provided or a composition comprising the one or more ligand dimers in an amount effective to treat the cancer is provided. In one embodiment the cancer is lung cancer. In another embodiment the subject is administered another anti-cancer agent. In one embodiment the other anti-cancer agent is administered prior to, subsequent to or concomitantly with the ligand dimers or composition thereof.

In yet another aspect a method of treating neurological disorder/disease in a subject comprising administering to a subject that has a neurological disorder/disease any one or more of the ligand dimers provided or a composition comprising the one or more ligand dimers in an amount effective to treat the neurological disorder/disease is provided. In one embodiment the subject is administered another agent for treating the neurological disorder/disease. In another embodiment the other agent for treating the neurological disorder/disease is administered prior to, subsequent to or concomitantly with the ligand dimers or composition thereof.

In still another aspect a method of treating a wound in a subject, comprising administering to a subject that has a wound any one or more of the ligand dimers provided or a composition comprising the one or more ligand dimers in an amount effective to treat the wound is provided. In one embodiment the subject is administered another wound healing agent. In another embodiment the other wound healing is administered prior to, subsequent to or concomitantly with the ligand dimers or composition thereof.

In another embodiment of the methods provided the contacting takes place in vivo. In yet another embodiment of the methods provided the contacting takes place in vitro.

In a further aspect a method for assessing the ability of one or more ligand dimers to control dimerization of one or more specific receptor pairs is provided. In one embodiment the method comprises contacting cells that express at least one type of Her receptor with one or more of the ligand dimers provided, and determining whether or not dimerization of the one or more specific receptor pairs occurs is provided. In another embodiment at least one of the receptors of the specific receptor pair is a Her receptor. In yet another embodiment whether or not dimerization of the one or more specific receptor pairs occurs can be determined by determining whether or not receptor signaling is promoted or inhibited. In still another embodiment determining whether or not receptor signaling is promoted or inhibited can be determined by determining whether or not signaling through a different receptor pair occurred. In one embodiment the different receptor pair is Her-1-Her-2.

In another embodiment the specific receptor pair is Her-1-Her-1. In yet another embodiment the specific receptor pair is Her-1-Her-3. In still another embodiment the specific receptor pair is Her-1-Her-4. In a further embodiment the specific receptor pair is Her-3-Her-3. In still a further embodiment the specific receptor pair is Her-3-Her-4. In yet a further embodiment the specific receptor pair is Her-4-Her-4. In another embodiment the specific receptor pair is a Her receptor and an integrin. In one embodiment the integrin is αvβ3 or α5β1. In another embodiment the Her receptor is Her-1, Her-2, Her-3 or Her-4.

DETAILED DESCRIPTION

Figure 1:
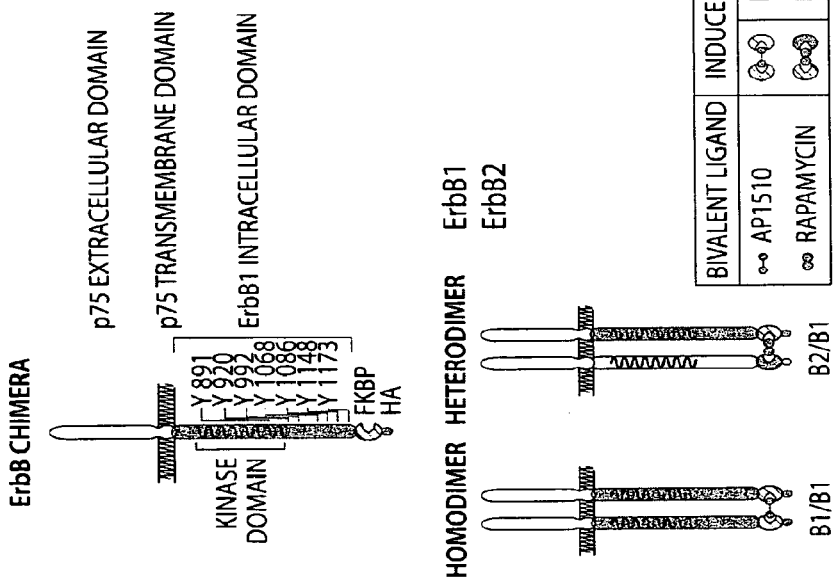
FIG. 1 illustrates some other approaches to control ErbB (Her) dimerization. As these require genetic manipulation of the cells, they are not suitable for in vivo therapies. An illustration of C-terminal chimeric Her-1 and Her-2 fusions with AP1510 or rapamycin binding domains is shown.
Figure 2:
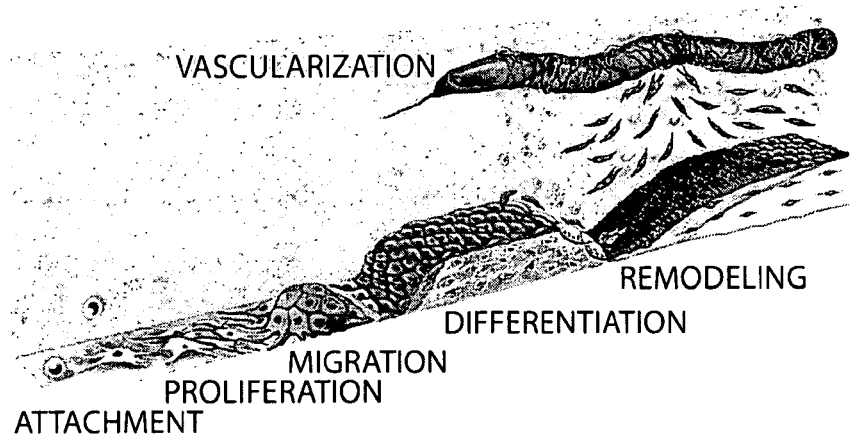
FIG. 2 shows some processes related to mesenchymal stem cell (MSC) behavior and tissue regeneration.
Figure 3:
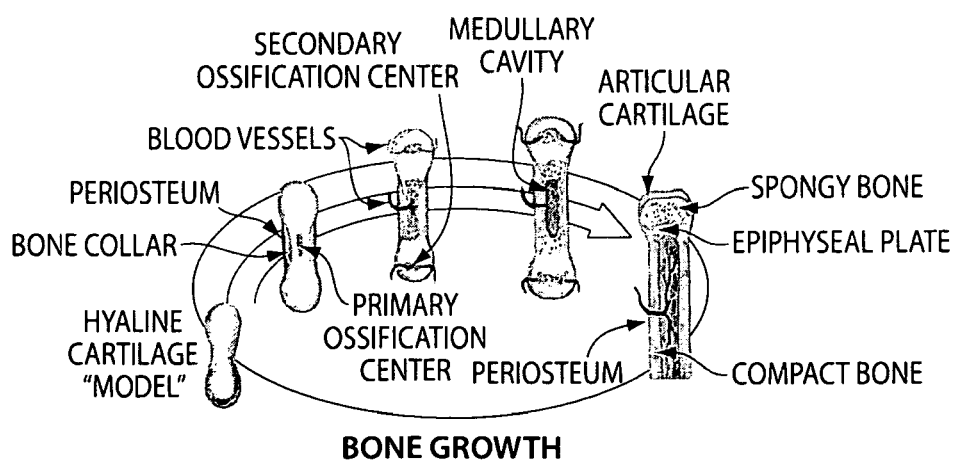
FIG. 3 shows a hyaline cartilage model of bone.

Receptors in the EGFR family require receptor dimerization induced by ligand binding in order to signal, and receptors can homodimerize or heterodimerize with other members of the family as well as with other receptors, such as the integrins. The EGF receptor family members activate multiple intracellular signaling pathways including ERK, PLCγ, and PI3kinase/Akt. These pathways influence cell survival, migration, proliferation, and differentiation. Upregulation of either the receptors or their ligands is observed in many cancers.

Known natural ligands of the EGFR are monomeric. Hence, efforts to stimulate these receptors for regeneration purposes employ monomeric soluble ligands and such ligands are commercially available from many sources. Efforts to inhibit signaling have focused on small molecule inhibitors of kinases, on antibodies that block ligand binding, or antibodies that sterically inhibit dimerization. It has not been previously appreciated that the EGFR signaling network can be tuned—up or down—by using molecularly-designed ligand dimers.

It has been surprisingly found that signaling by epidermal growth factor receptor (EGFR) family members (Her-1, Her-2, Her-3 and Her-4) can be controlled by forcing particular receptors to homo- or hetero-dimerize, allowing enhancement or diminishment of signaling by quantitative control of receptor occupancy in dimers. With monovalent ligands, each ligand-bound receptor is a "free agent" to heterodimerize with any other EGFR family member or other receptors, such as an integrin, and the absolute or relative number of each type of dimer is difficult to control. With ligand dimers, however, it has been unexpectedly found that it is possible to force receptors into a desired partnering relationship through mass action. For example, if a particular cell expresses 20,000 Her-1 and 10,000 Her-3, provision of soluble Her-1 ligand dimer would inhibit the formation of Her-1-Her-3 heterodimers or of Her-1-Her-2 heterodimers. Likewise provision of EGF-NRG-1 heterodimer ligand would drive most Her-3 receptors into dimers with Her-1 and prevent dimers with Her-2, and NRG-1 dimers would drive Her-3 into homodimers and inhibit Her-1-Her-3 dimers.

Provided herein, therefore, are compositions and methods for controlling homo- and hetero-dimerization of cell surface receptors, such as the Her (ERBb) receptors. The receptors discussed herein are intended to include the wild type versions of the receptors as well as polymorphic or mutant versions. These compositions and methods include compositions and methods for controlling the heterodimerization of a Her receptor with a receptor not in the Her family. Such other receptors include integrins. As used herein, "controlling Her (or Her receptor) dimerization" refers to the ability to force (i.e., cause) the dimerization of a Her receptor with another receptor, such as another Her receptor or an integrin. Controlling dimerization can allow for the control (e.g., promoting or inhibiting) of signaling outcomes in cells, with broad applications in regenerative medicine, cancer, neurological disorders, etc., as the receptors described herein are involved in regulating cell function in many if not virtually every tissue type. The ligand dimers provided allow quantitative control over the ratio of various activated (or silenced) receptor dimers, regardless of the total or relative expression levels of each type of receptor.

The ligand dimers provided can be contacted with cells that express Her receptors or Her receptors as well as integrins. Such cells are any cells that express at least one type of Her receptor or at least one type of Her receptor and at least one type of integrin.

Her receptor expression has been reported in virtually every known cell type. Cells that express Her receptors include cells of various tissues, bone, of the central nervous system as well as cells of a cancer or tumor or wound. Cells that express at least one type of Her receptor include mesenchymal stem cells (MSCs), which give rise to many kinds of connective tissues. In general, such cells can express at least 3 EGFR family members. Cells that express at least one type of Her receptor also include keratinocytes that use EGFR signaling in repairing skin wounds. Further, the cells include cells involved in angiogenesis, such as endothelial cells or fibroblasts. Angiogenesis, the process of forming blood vessels, involves, for example, response of EGFR and Her-2 expressed on endothelial cells and fibroblasts. EGFR family members are also prominently expressed in neurons and supporting glial cells in the brain, where they are involved in homeostasis of tissue and growth of neurons. Cells that express at least one type of Her receptor, therefore, also include neurons and supporting glial cells. When the cells are cancer cells, the cells can be, for example, bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, prostate cancer cells, testicular cancer cells or melanoma cells. In one embodiment, the cells are from a cancer that aberrantly express Her-2. In another embodiment, they are from cells that express wild-type or mutant Her receptors, such as EGFR and/or Her-3. The ligand dimers provided, therefore, can be used to force the dimerization of Her receptors on these cells.

As used herein, a "specific receptor pair" refers to one particular combination of Her receptor with another receptor. In embodiments where the specific receptor pair is a pair of Her receptors, one of the Her receptors of the pair must be a Her-1, Her-2, Her-3 or Her-4 receptor and the other must be a Her-1, Her-2, Her-3 or Her-4 receptor. It is not intended that the term refers to two specific molecules but rather refers to two receptors each of a certain type. In some embodiments, the two receptors can be the same type of receptor (e.g., both are Her-1, both are Her-2, both are Her-3, both are Her-4). The following are examples of specific receptor pairs the dimerization of which can be forced with the ligand dimers provided herein: Her-1-1, Her-1-3, Her-1-4, Her-3-3, Her-3-4 and Her-4-4 (also referred to herein as Her-1-Her-1, Her-1-Her-3, Her-1-Her-4, Her-3-Her-3, Her-3-Her-4 and Her-4-Her-4). Other examples of specific receptor pairs the dimerization of which can be forced with the ligand dimers provided include Her-1-integrin, Her-2-integrin, Her-3-integrin and Her-4 integrin. The integrin can be, for example, αvβ3 integrin (also referred to herein as αvβ3), α6β1 integrin (also referred to herein as α6β1), αIIbβ3 integrin (also referred to herein as αIIbβ3), αMβ2 integrin (also referred to herein as αMβ2) or α5β1 integrin (also referred to herein as α5β1). Other integrins are known to those of ordinary skill in the art. Therefore, the specific receptor pairs also include Her-1-αvβ3, Her-1-α6β1, Her-1-αIIbβ3, Her-1-αMβ2, Her-1-α5β1, Her-1-α2β1, Her-2-αvβ3, Her-2-α6β1, Her-2-αIIbβ3, Her-2-αMβ2, Her-2-α5β1, Her-1-α2β1, Her-3-αvβ3, Her-3-α6β1, Her-3-αIIbβ3, Her-3-αMβ2, Her-3-α5β1, Her-1-α2β1, Her-4-αvβ3, Her-4-α6β1, Her-4-αIIbβ3, Her-4-αMβ2, Her-4-α5β1 and Her-1-α2β1. The ability to control dimerization of specific receptor pairs allows for control over receptor signaling. Signaling, therefore, can be controlled with potentially different outcomes by allowing access to a range of other signaling networks.

Signaling can be controlled by forcing the dimerization of one or more specific receptor pairs that can result in the promotion or inhibition of receptor signaling. This can be accomplished by contacting cells with one or more types of ligand dimers where each type of ligand dimer can force the dimerization of one or more specific receptor pairs. For example, forced dimerization of Her-1-1, Her-1-2, Her-1-3, Her-1-4 and/or Her-4-4 can result in receptor signaling as well as the promotion of cell proliferation. Survival of cells can be promoted with forced Her-1-1 and/or Her-1-3 dimerization. The ligand dimers provided herein, therefore, include ligand dimers that force the dimerization of Her-1-1, Her-1-3, Her-1-4 or Her-4-4 or some combination thereof. Migration and/or differentiation of cells can be controlled (e.g., promoted) with forced Her-1-1, Her-1-3 or Her-3-3 dimerization and/or Her-integrin dimerization. Therefore, the ligand dimer can also be one that forces the dimerization of Her-integrin, such as Her-1-integrin, and such a ligand dimer can be used alone or in some combination of the ligand dimers provided herein. The ligands of the ligand dimer that can force the receptor dimerization of Her-1 with an integrin can be, for example, EGF and RGD. In one embodiment where cell migration inhibition is desired the ligand dimers force Her-1-1, Her-1-3 and/or Her-3-3 dimerization. Ligand dimers that can inhibit cell migration include EGF-NRG ligand dimers as well as NRG-NRG ligand dimers. In some embodiments such ligand dimers are used to inhibit cell migration. In other embodiment where cell migration inhibition is desired a ligand dimer that decreases Her-2 signaling can be used. Such ligand dimers are described further elsewhere herein and can include ERG-NRG ligand dimers.

Signaling can also be controlled by forcing dimerization of one or more types of receptor pairs in order to inhibit the receptors of these pairs from interfering with the dimerization of another specific receptor pair. For example, signaling through the Her-1-2 receptor pair can be promoted by forcing the dimerization of the other types of receptors present on the cell surface such that they do not dimerize with Her-1 or Her-2 thus allowing for "natural" Her-1-2 dimerization. As used herein, "natural dimerization" is intended to refer to any dimerization that is not the result of forced dimerization from an applied ligand dimer as provided herein. Forcing the dimerization of the other types of receptors to each other but not to Her-1 or Her-2 would allow for Her-1 and Her-2 to be free to dimerize to each other and promote signaling in some embodiments.

Similarly, signaling can be controlled by forcing dimerization of one or more types of receptor pairs so that the receptors are not available for dimerization with a specific receptor, the dimerization of which would be undesirable. For example, there are instances where Her-2 dimerization with other receptors is not desired. Therefore, ligand dimers can be used to force the dimerization of the other receptors to each other such that Her-2 dimerization with the other receptors is inhibited. This can be beneficial for the treatment of cancer, such as lung cancer, or pulmonary fibrosis. Ligand dimers that can inhibit Her-2 signaling and/or promote dimerization of receptors with receptors other than Her-2 include EGF-NRG and EGF-EGF ligand dimers (which can be used to promote EGFR homodimers).

EGF-EGF ligand dimers have also been found to increase cell apoptosis and/or decrease cell viability, while EGF-NRG have also been found to increase cell survival. EGF-NRG ligand dimers have also been found to increase Her-1-3 or Her-1-4 dimerization as well as Her-1 and Her-3 signaling. Additionally, EGF-NRG ligand dimers have been found to reduce mitogenic signaling as well as decrease Her-2-3 dimerization. NRG-NRG ligand dimers have been found to increase cell viability. These ligand dimers as well as methods of using these ligand dimers for these purposes are also provided herein.

As another example, there are circumstances where signaling through a specific receptor pair is not desirable. Therefore, forcing dimerization of at least one of the receptors of this specific receptor pair to another type of receptor can result in inhibiting the signaling that occurs through the receptor pair. For example, Her-2-3 receptor signaling may not be desirable in some embodiments; therefore, forced Her-3 homodimerization (or Her-3-3 or Her-3-Her-3) or dimerization with Her-1, Her-4 or an integrin can result in the inhibition of Her-2-3 dimerization and signaling. In some embodiments, the benefit of this inhibition is cell death. Again, this can be beneficial for the treatment of cancer, such as lung cancer, or pulmonary fibrosis.

The following table provides some examples of specific receptor pairs, the behaviors that are controlled as well ligands for the receptors. Ligand dimers are provided herein which force the dimerization of these receptor pairs and which comprise the ligands provided. In addition, methods for attaining the below outcomes using the ligand dimers are also provided.

Table 1 lists the subset of signaling axes involved in the control of cell behaviors critical for tissue regeneration. These are organized into a hierarchy of cell behaviors, axes, ligands and phenotypes.

| Behavior | Axis | Ligand | Phenotypes |
|---|---|---|---|
| Proliferation | Her-1, Her-2 | EGF, NRG1 | Synthesis |
| Migration | Her-1,-2,-3; integrins | EGF, NRG1, RGD | Speed/Persistence/Invasion |
| Differentiation | Her-3,-4; integrins small molecule | NRG1, RGD, small molecules | Osteo- and Chondro-Markers (Mineralization, Alkaline Phosphatase, Osteryx) |
| Homeostasis | Her-1,-2,-3,-4; Integrins | EGF, NRG1, RGD | Viability and Lineage Commitment |

EGF (epidermal growth factor);
NRG1 (neuregulin-1β);
RGD (tripeptide integrin ligand);
small molecules include dexamethasone, ascorbic acid, β-glycerophosphate In the methods provided, signaling can be promoted or inhibited by the forced dimerization of specific receptor pairs. All of the ligand dimers that are contacted with one or more cells may not all cause the dimerization of the desired specific receptor pair. However, it is intended that enough of the ligand dimers force the desired dimerization and such dimerization has the desired result. Therefore, to accomplish any of the desired results described herein it is not required that all of the specific receptor pairs on the one or more cells are forced to dimerize as a result of the ligand dimers they are intended to be targeted by.

The ligands for use in the dimers provided herein can be any ligand which binds a receptor provided that its use in a ligand dimer results in forced dimerization of at least one type of specific receptor pair. In some instances, the ligand can bind more than one receptor and such ligand may be used provided that its use in a ligand dimer results in a desirable level of forced dimerization and not an undesirable level of other dimerization (i.e., dimerization of other receptor pairs that would interfere with the desired signaling). In some embodiments, the ligands are chosen for their level of affinity to the receptors they bind. For example, EGF binds Her-1 specifically and with high affinity. EGF has approximately 1000 times greater affinity for Her-1 than for Her-3 or Her-4. Neuregulin-1β binds Her-3 and Her-4 receptors with approximately 5000-fold greater affinity than Her-1. In some embodiments, the ligands have an affinity as defined by a $k_d$ of 50 nM or less for the receptor or receptors it is to bind as part of a ligand dimer that forces receptor dimerization. In other embodiments, the ligands of the ligand dimer each have an affinity of 40 nM, 30 nM, 25 nM, 20 nM, 15 nM, 10 nM, 5 nM, 2 nM, 1 nM or less. Depending on the circumstances, the types of receptors expressed on the cells, the desired signaling, etc., one of ordinary skill in the art based on the teachings provided would be able to determine the appropriate ligands for use in the ligand dimers. Some examples of ligand dimers include EGF-EGF, EGF-NRG1, EGF-RGD, NRG-NRG, NRG1-NRG1 and NRG1-RGD. The reference to the ligands in a particular order is not meant to imply a specific order. Rather it implies that the ligand dimer comprises the two recited ligands. For example, "EGF-NRG1" refers to a ligand dimer with EGF and NRG1 as the two ligands in any order.

TABLE 2

Kinetic rates of the interactions of NDF with soluble ErbB receptor/bodies

| | $k_{on}$ (mol$^{-1}$ s$^{-1}$) × 10$^4$ | $k_{off}$ (s$^{-1}$) × 10$^{-4}$ | $K_D$ (nM) |
|---|---|---|---|
| ErbB-1 | 0.9 ± 0.2 | 500 ± 200 | 5550 |
| ErbB-2 | 1.9 ± 0.8 | 161 ± 33 | 850 |
| ErbB-3 | 49 ± 4 | 6.5 ± 0.9 | 1.3 |
| ErbB-4 | 120 ± 21 | 7.6 ± 2.2 | 0.7 |

Ligands include the natural ligands for the receptors (i.e., ligands for the receptors that control signaling, as found in nature, without human intervention), polypeptides derived therefrom as well as synthetic mimics. For example, the ligands for Her-1 include epidermal growth factor (EGF), transforming growth factor-alpha (TGF-α), epiregulin, heparin-binding epidermal-like growth factor (HB-EGF) and amphiregulin. Ligands for Her-3 include neuregulin-1α, neuregulin-1β, heregulin-4 and β-cellulin. Ligands for Her-4 include epiregulin, heparin-binding epidermal-like growth factor (HB-EGF), neuregulin-1α, neuregulin 1β, neuregulin-3 and neuregulin-4. Her-2 has no known ligand, but it has a tyrosine kinase domain that is activated upon heterodimerization with ligand-bound Her-1, Her-3 or Her-4. Her-2 among all receptors in the family reportedly has the broadest range of interactions with intracellular signaling molecules. Ligand for integrins include RGD, LDV, laminin, collagen, ADAM family members, COMP, connective tissue growth factor, Cyr61, E-cadherin, ESM-1, fibrillin, fibrinogen, fibronectin, ICAM-4, LAP-TGFβ, MMP-2, nephronectin, L1, plasminogen, POEM, tenascin, thrombospondin, VEGF-C, VEGF-D and vitronectin. Integrin ligands also include any of the various peptide ligands well known in the art. Integrin peptide ligands include those that comprise the sequence KVGFFKR (SEQ ID NO: 1), (GRGDSP)³ (SEQ ID NO: 2) or SVVYGLR (SEQ ID NO: 3), etc. In some embodiments, the ligand dimer is any of the ligand dimers described herein including those illustrated below in the Examples and Figures. In some embodiments, the ligands of the ligand dimers provided are each not an antibody. In other embodiments, the ligands of the ligand dimers provided are each not an antibody or antigen-binding fragment thereof.

In one embodiment when Her-3 homodimerization is desired, the ligand dimer can be a NRG-NRG ligand dimer. In another embodiment when Her-3 homodimerization is desired, the ligand dimer is NRG1-NRG1. NRG-NRG ligand dimers, such as NRG1-NRG1 ligand dimers, can be used to attenuate Her-3 or Her-4 signaling. Such ligands and methods of using such ligands, for example for the aforementioned purpose or for increasing cell apoptosis or decreasing cell survival, are provided herein. In some embodiments, the cells are cells that express Her-3 with EGFR or cells that express Her-2 but not Her-4. In other embodiments the cells are cancer cells. In still other embodiments a method whereby the NRG-NRG ligand dimer is administered to a subject with cancer is provided.

In some embodiments, a therapeutic advantage of the ligand dimers compared to monoclonal antibodies, such as Herceptin, is their relatively small size and ability, therefore, to penetrate tissue more deeply. In some embodiments, therefore, the ligand dimer is one that is able to more deeply penetrate a tissue as compared with a monoclonal antibody. In other embodiments, the ligand dimer is able to penetrate a tissue more deeply than a monoclonal antibody or an antigen-binding fragment thereof.

Figure 30:
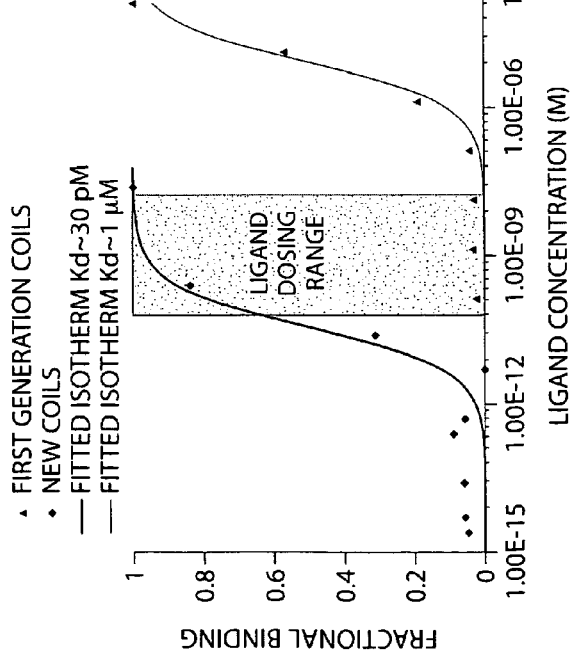
FIG. 30 demonstrates the enhanced affinity of altered coiled coil regions.
Figure 31:
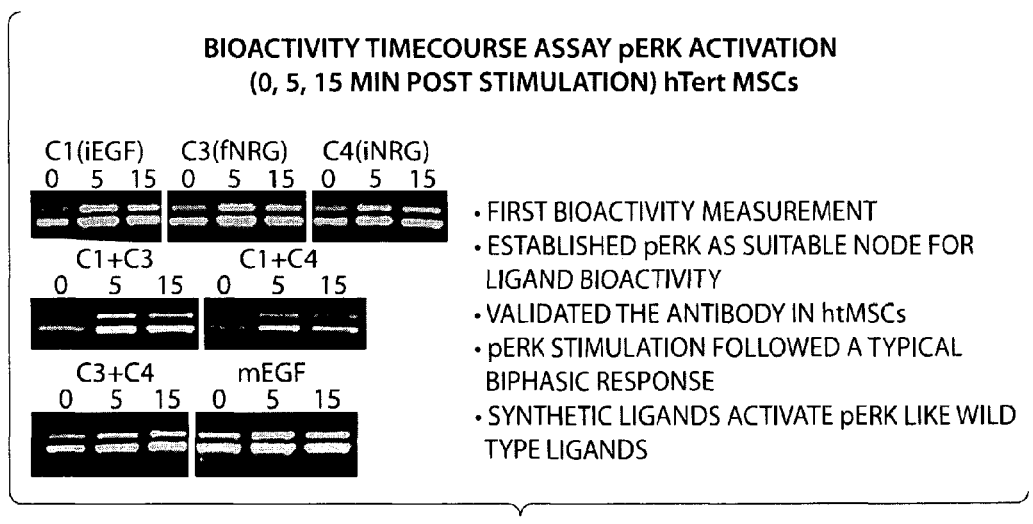
FIG. 31 illustrates a bioactivity timecourse assay.
Figure 32:
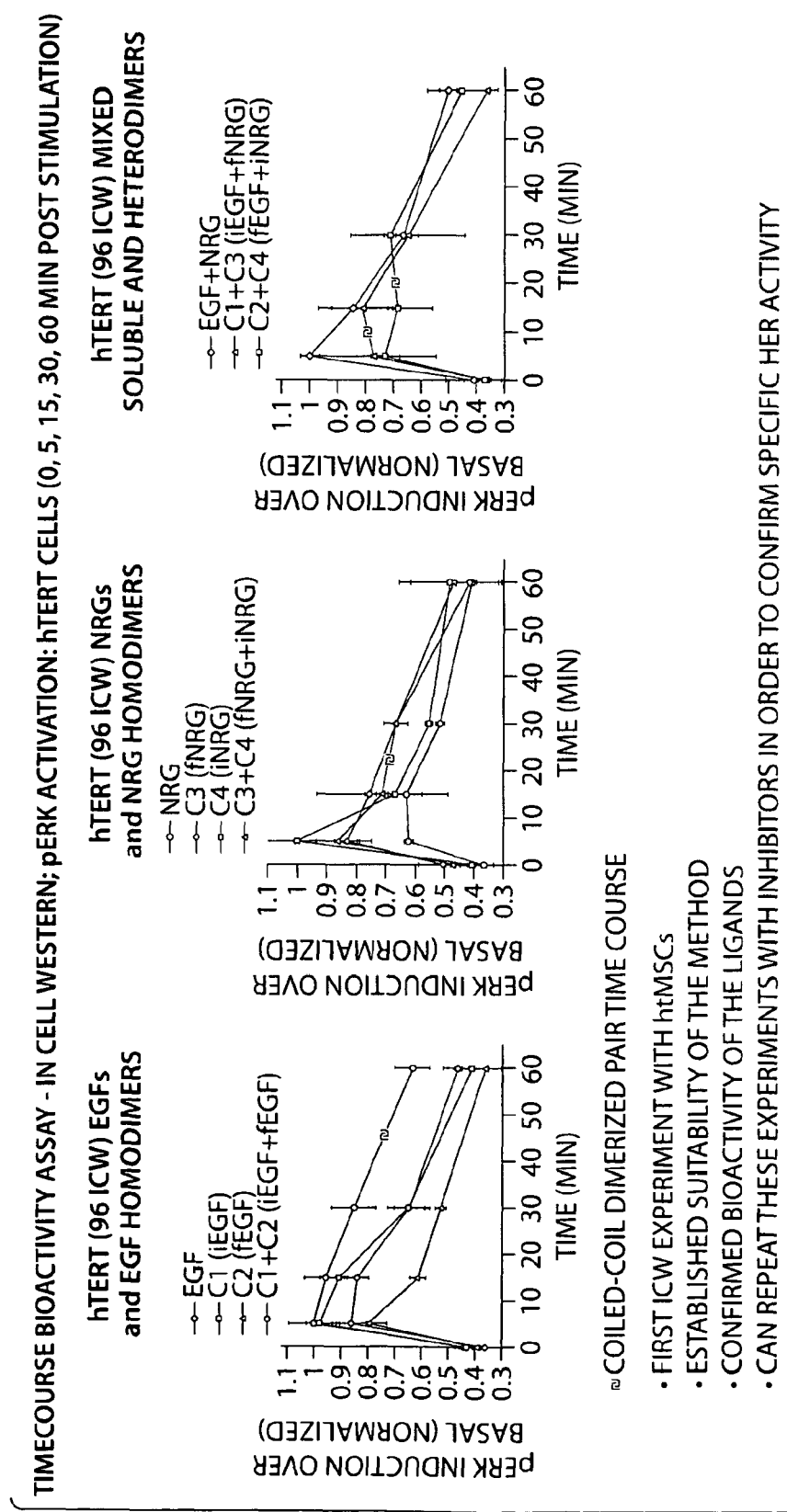
FIG. 32 provides results from a timecourse bioactivity assay in cell Western.
Figure 33:
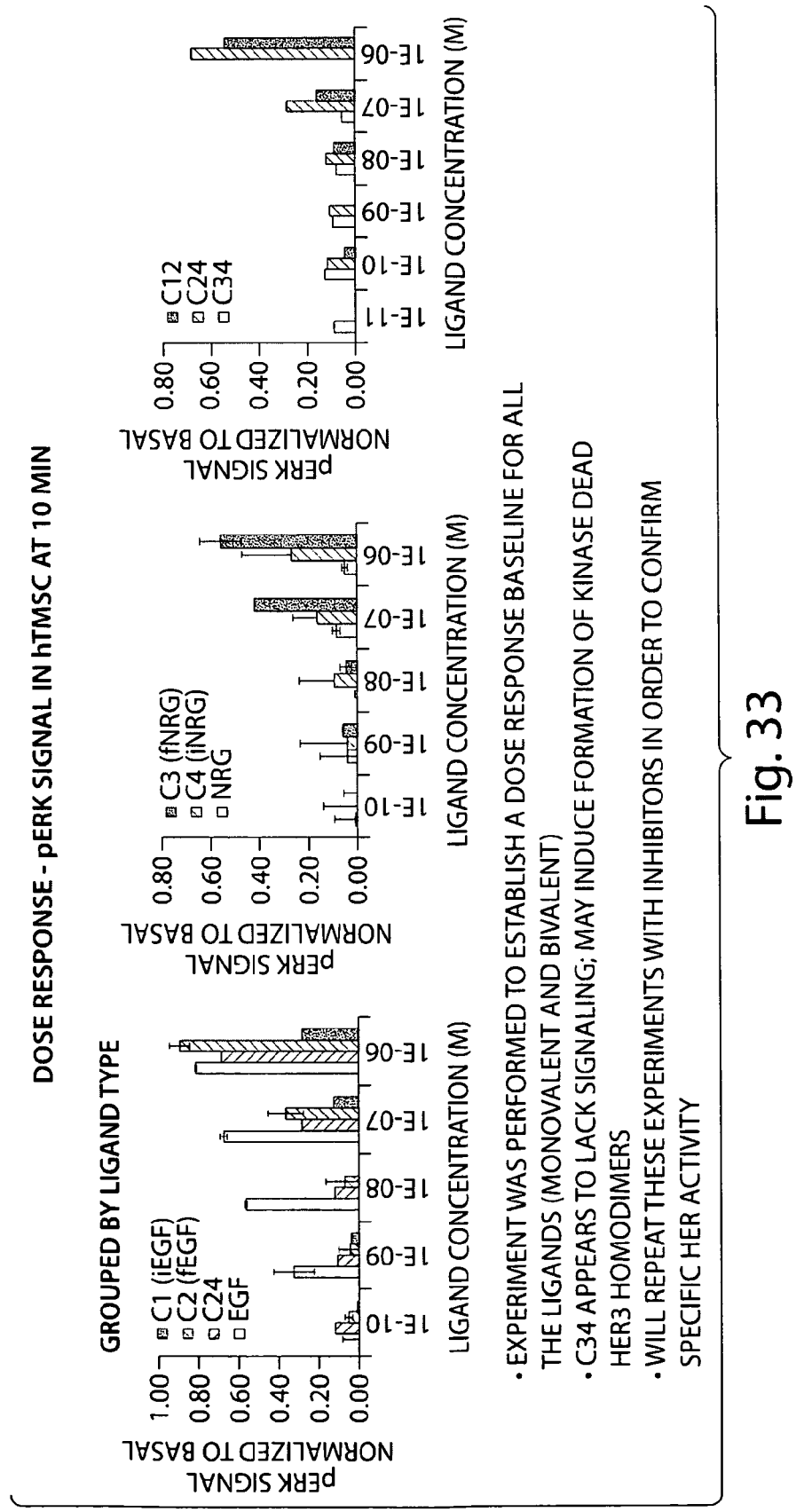
FIG. 33 provides results from an experiment performed to establish a dose response baseline (monovalent and bivalent). C34 appears to lack signaling, and formation of kinase dead Her-3 homodimers appears to have been induced. This experiment can be repeated with inhibitors to confirm specific Her activity.
Figure 34:
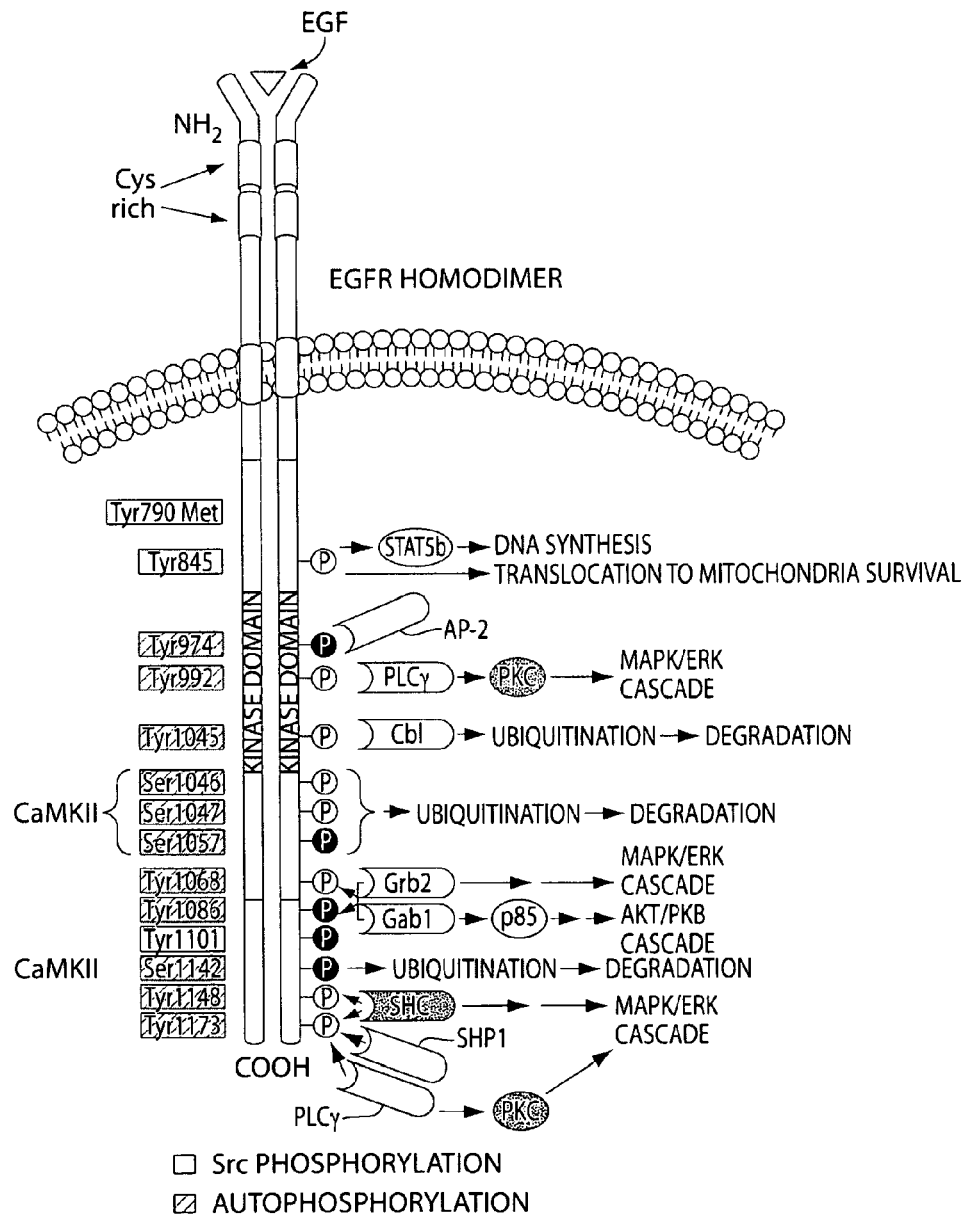
FIG. 34 illustrates that the pERK signaling methods can be extended to measure pHer-1, -2, -3, -4 under various ligand conditions. Evidence of tyrosine phosphorylation differences may be found due to the various ligand conditions. If ICW is used, each antibody in each cell type can be validated. Mass spectrometric determination of pY profile would be quantitative and of high throughput.
Figure 34:
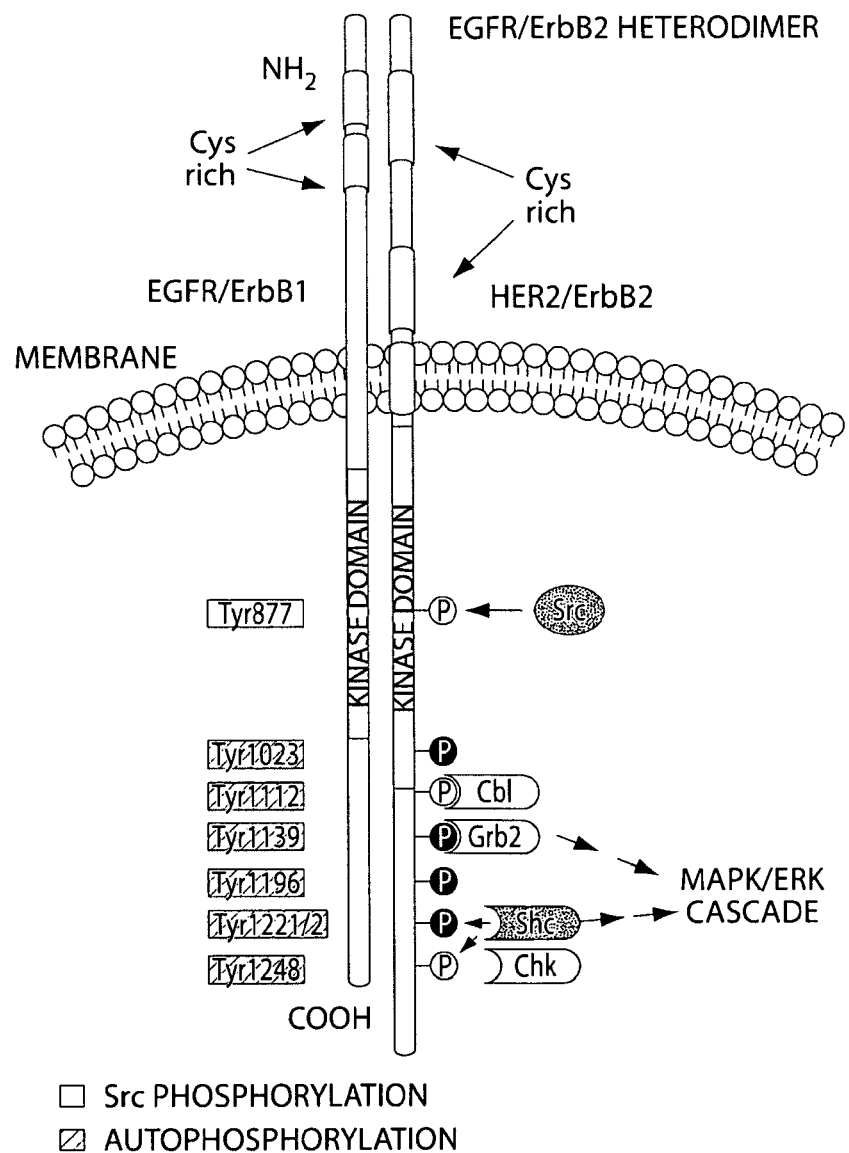
Figure 35:
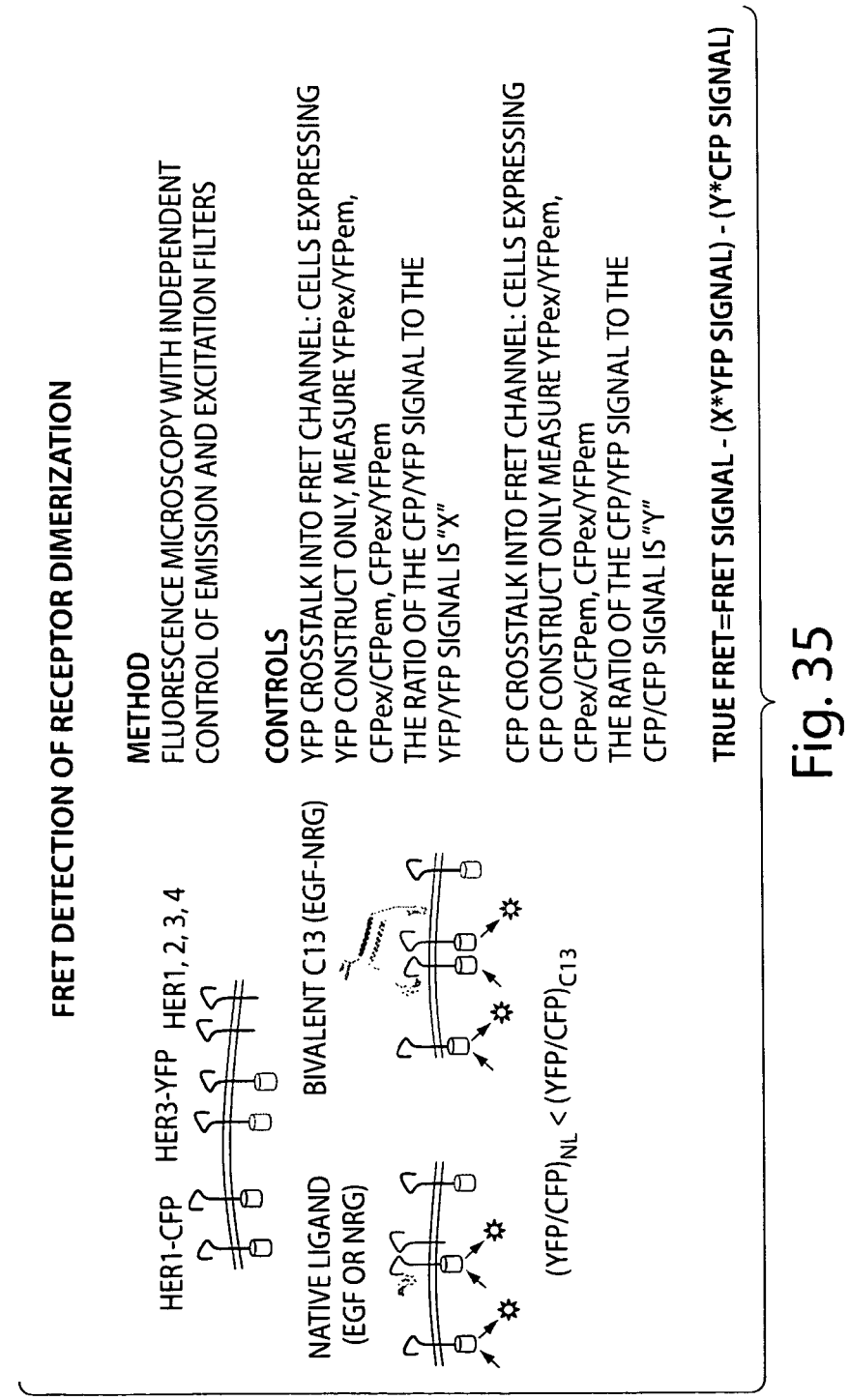
FIG. 35 illustrates an example of FRET detection of receptor dimerization.
Figure 36:
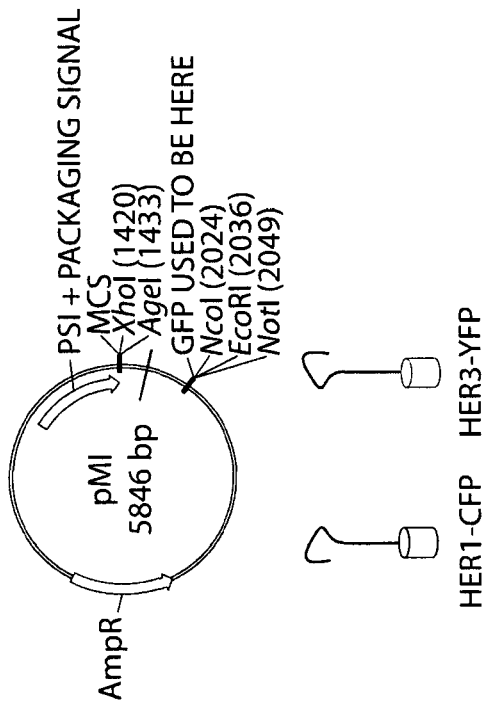
FIG. 36 illustrates an example of FRET detection of receptor dimerization.
Figure 37:
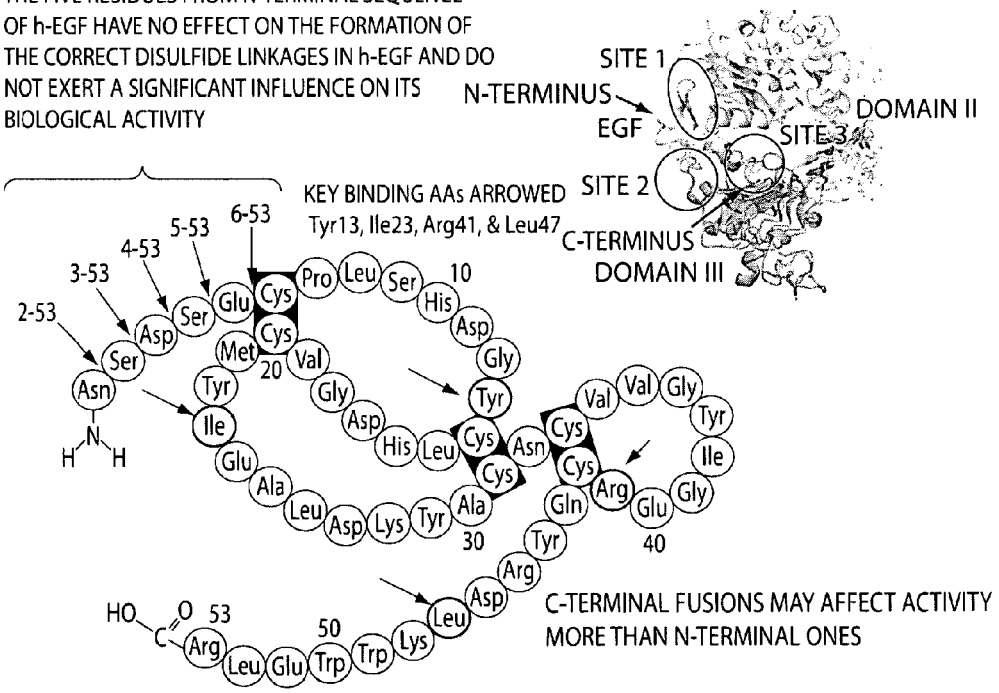
FIG. 37 shows an illustration of EGF binding residues. The five residues from the N-terminal sequence of h-EGF have no effect on the formation of the correct disulfide linkages in h-EGF and do not exert a significant influence on its biological activity. C-terminal fusions may affect activity more than N-terminal ones.
Figure 38A:
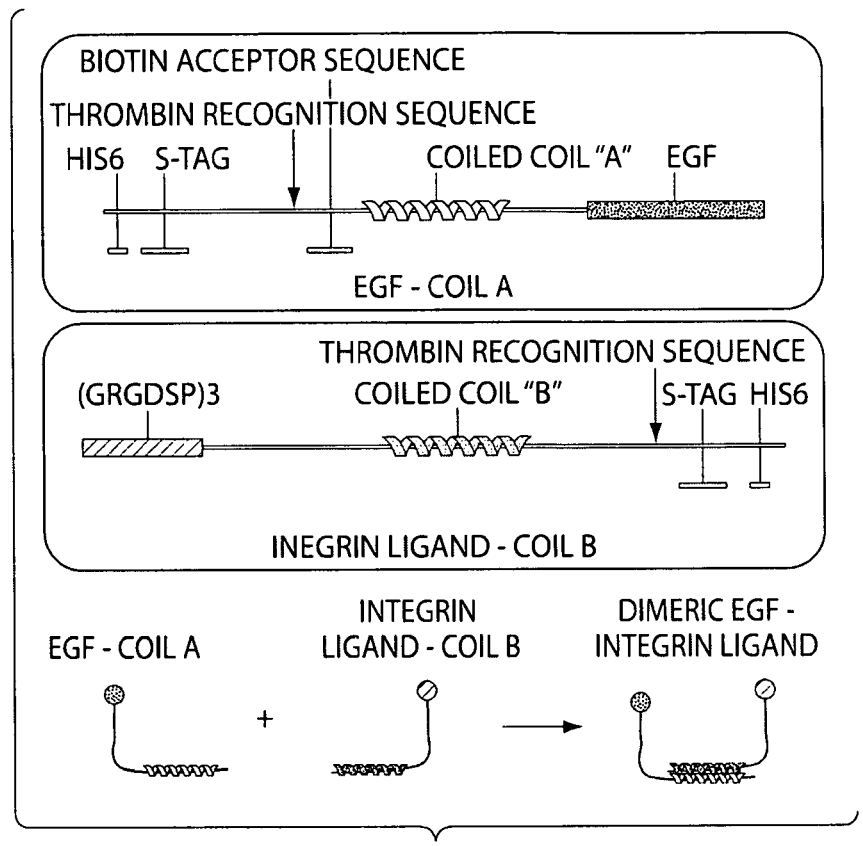
FIG. 38 illustrates one approach to produce dimeric EGF and integrin ligands (FIG. 38A). Any Her ligand can be substituted for EGF.
FIG. 38B illustrates the expected effect of dimeric ligand presentation on cell signaling.
Figure 38B:
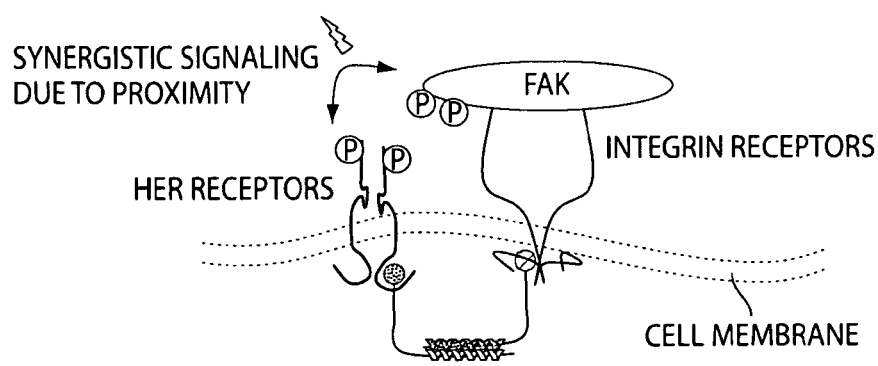
Figure 39A:
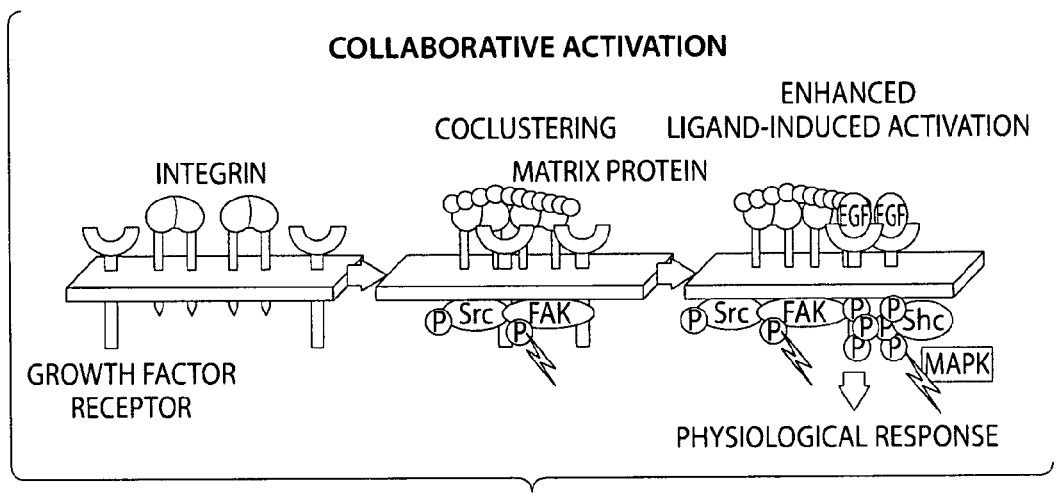
FIG. 39 illustrates that bringing Her and integrin receptors into close proximity can have synergistic signaling effects.
Figure 39B:
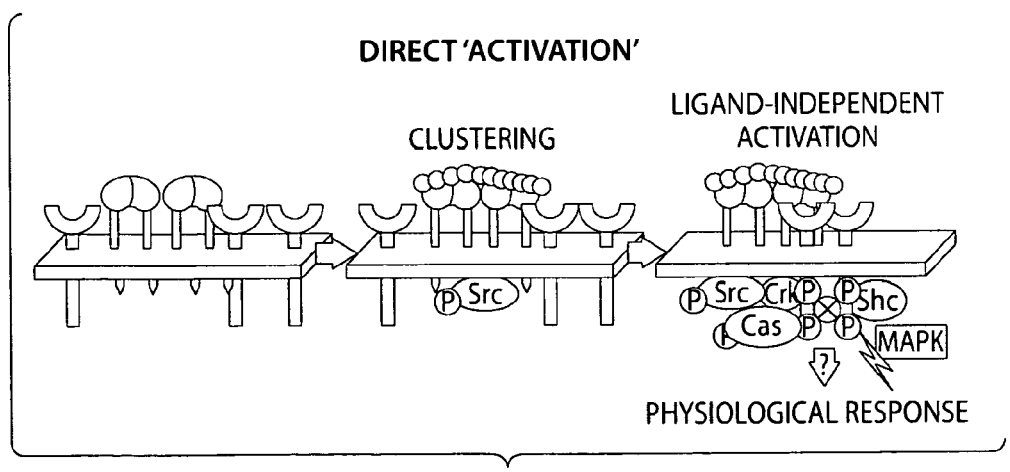

Receptor dimer features can guide the design of ligand dimers (spacing, orientation, binding residues, termini accessibility, etc.). In the ligand dimers provided, the two ligands are linked with a linker such that the ligand dimer can force the dimerization of a specific receptor pair. The linker, for example, can comprise a coiled coil. A coiled coil is a structural motif in proteins, in which, in general, two to seven alpha-helices are coiled together like the strands of a rope. In some embodiments, the coiled coil of the ligand dimer is one with two alpha-helices coiled together. Such a ligand dimer can be formed by first attaching a ligand to one single alpha helix coiled coil domain (i.e., one ligand monomer) separately from another ligand attached to a single alpha helix coiled coil domain (i.e., another ligand monomer) and contacting the two ligand monomers such that the ligand dimer is formed through an interaction with the two alpha helix coiled coil domains, for example, at concentrations of approximately 1 nM. In some embodiments the coils comprise a peptide with the amino acid sequence as set forth in SEQ ID NO: 4 or 5 or any of the sequences provided in FIG. 30. In some embodiments the interaction of the coils of a coiled coil exhibits a Kd of no more than $1 \times 10^{-10}$, $1 \times 10^{-11}$, $1 \times 10^{-12}$, $1 \times 10^{-13}$, $1 \times 10^{-14}$ or $1 \times 10^{-15}$ M. The linker can also comprise a peptide spacer. For example, the peptide spacer can be on either or both ends of the coiled coil. Each of the peptide spacers can be attached to a single alpha helix coiled coil domain of the coiled coil. The peptide spacer can be, for example, a peptide of 5, 6, 7, 8, 9, 10, 15, 20, 25, 30, 35, 40, 45 or 50 amino acids or more. The number of amino acids in the peptide spacer may be, in some embodiments, 20 amino acids or up to 10 amino acids greater or fewer, depending on the particular ligand and length of coil. The ligand spacing can influence avidity through its control of binding/dissociation kinetics and can be used to tune avidity.

The linker can also comprise a water soluble flexible polymer with or without spacers on either or both ends. Examples of spacers are as provided immediately above. The water soluble flexible polymer is one that can covalently link the two ligands together, is biocompatible, does not interfere with the desired signaling effects and allows for the forced dimerization of a specific receptor pair. Water soluble flexible polymers include polyethylene oxide (PEO), dextran, polyacrylic acid and polyacrylamide.

The length of the linker required can be determined with methods known to those of ordinary skill in the art. In general, the length of the linker is dependent on the distance between receptor ligand sites. For example, the length of the linker can be determined based on a calculus using the radius of gyration. Generally, for the linkers specifically provided herein the radius of gyration is calculated according to the following:

$$\text{Radius of gyration} = c*n^{3/5}, \text{ where } c \text{ is a constant that depends on the type of polymer}$$

For example, when PEO is the polymer, c is 0.3 nM. In some embodiments, the length of the linker is within 50% of the radius of gyration. As an example, the length of the linker may be equal to the radius of gyration. The length of the linker, in some embodiments, is in the range of 20 nm to 10,000 nm. In other embodiments, the length of the linker is in the range of 80 nm to 10,000 nm. In still other embodiments, the length of the linker is in the range of 100 nm to 10,000 nm. In still other embodiments, the length of the linker is in the range of 20 nm to 1,000 nm. In other embodiments, the length of the linker is in the range of 80 nm to 1,000 nm. In still other embodiments, the length of the linker is in the range of 100 nm to 1,000 nm. In a further embodiment, the length of the linker is about 200 nm.

The ligand dimers provided can be produced with the methods provided herein or that are otherwise known in the art. Their binding to receptors can be assessed by binding assays which include, for example, far Western spot blot, immunofluorescence binding assay (ELISA-based), surface plasmon resonance (SPR-Biacore), isothermal titration calorimetry (ITC), cross-linking and SDS-PAGE, high resolution size exclusion chromatography (HRSEC) and native gels.

Bioactivity of the receptors can be assessed with probes. Such probes include antibodies, such as antibodies to a pan Her downstream marker (e.g., pERK (T202/Y204)) as well as antibodies that are receptor specific (e.g., pHer-1(Y1068), pHer-2(Y1221), pHer-3(Y1289) and pHer-4(Y1284)). Inhibitors of Her bioactivity can also be used in assays to assess bioactivity. Such inhibitors include small molecules (e.g., Her-1/AG1478, pan Her "CFAB") and RNAi. For example, validated siRNAs are available for all Her receptors. Alternatively, RNAis are available in lentiviral packaging vectors to facilitate transduction of recalcitrant cell types, such as MSCs. Bioactivity can also be assessed with dose response assays (e.g., that measure pERK activation, such as at 10 minutes) and time course assays (e.g., that measure pERK activation over time). The conditions under which such assays can be conducted include, for example, under serum starvation at about 12 hours with 0.1% FBS medium and a ligand concentration of 10 pM-100 nM. The assays can be, for example, in cell Western or a Western blot and can also include the use of a LI-COR ODYSSEY IR dye scanner.

Binding and internalization of ligands can be measured with, for example, radio-labeling experiments that can quantitatively measure binding affinity and internalization of ligand/receptor complexes. The differences in binding affinity would be expected to be due to the bivalent interaction with receptor dimers (avidity effect). Differences in receptor trafficking between native and bivalent ligands would also suggest biased receptor pairings (e.g., Her-1 homodimers are trafficked at higher rates than other dimers).

Bivalent ligand induced receptor dimerization bias can be confirmed with biochemical assays and phenotypic assays. Biochemical assays include Her receptor FRET fusions (e.g., Her-1-CFP, Her-3-YFP), Her-receptor complementation fusion (e.g., luciferase or DHFR); receptor crosslinking (e.g., blot for all Her receptors), coimmunoprecipitation (e.g., pull down Her-1, blot for Her-x) and mass spectrometry of Y/pY. Phenotypic assays include assays for proliferation, cell death migration and differentiation.

A phenotypic assay can be performed to assess proliferation and/or cell death. As an example, proliferation of HeLa, MCF-7 and hTMSCs under various ligand conditions can be measured at 48 and 96 hours using a CYQUANT assay. The experiment can be performed with low serum (1%). The ligands (e.g., EGF; NRG; C1, 2, 3, 4 (monovalent forms); C12 (EGF-EGF); C13 (EGF-NRG) and C34 (NRG-NRG) are all at a concentration of 50 nM as one example. Bivalent ligand forms may signal less potently than monovalent or native forms and may lead to less proliferation due to exclusion of Her-2 signaling complexes. MCF-7 proliferation may suffer under the C34 condition due to formation of silent complexes. Other studies can be performed with, for example, other Her-3-overexpressing cancer cells.

Another phenotypic assay can be one that assesses migration. Migration on 2D surfaces using any type of biotinylated substrate (e.g., PMMA/PEG-biotin gels, commercial biotin-substituted 96-well plates, etc.) can be used to assess the effects of tethered ligands on migration of MSCs. Time lapse microscopy can be used to measure speed and persistence of MSCs under various ligand conditions. Characterization of surface biotinylation can also be performed with functionalization with biotinylated C1(EGF).

As described above, the ligand dimers provided can enhance or inhibit receptor signaling. The promotion or inhibition of the receptor signaling can be accomplished by contacting cells with ligand dimers that can force specific receptor pairings. Methods of accomplishing this are, therefore, provided. The cells that can be contacted with the ligand dimers can be any cells that express the receptors of which forced dimerization is desired. The ligand dimers can be used to control development, wound healing, migration, and tissue homeostasis. Methods, therefore, for attaining these outcomes with the ligand dimers are also provided. As an example, the ligand dimers can be used to promote cell proliferation. Therefore, the ligand dimers can be used to harness the regenerative potential of, for example, mesenchymal stromal cells (MSCs), endothelial cells, and neurons, which all express Her family members. HeLa cells express Her-1 and Her-2 and are responsive to EGF and have low responsiveness to NRG. MCF-7 cells express Her-3 and are responsive to NRG. htMSC cells express Her-1 and Her-2 and are responsive to EGF and NRG.

The ligand dimers can be used to regenerate tissue and, furthermore, can be used in wound healing. MSCs express Her family receptors and are responsive to EGF and NRG stimulation and are involved in wound healing of many tissue types. The cells can be cultured on synthetic matrices. Mesenchymal tissues include bone, cartilage, muscle, tendon, and fat. The lineage commitment from MSCs is governed by a variety of growth factors (e.g., EGF, FGF, BMPs) and cytokines and follows a path that is similar to hematopoiesis in diversity and intermediate cellular states. MSC behavior is affected by growth factors (e.g., EGF, FGF, BMPs), proximal cell types, ECM/synthetic scaffolds and hypoxia. Injury and disease in any one of the terminally differentiated mesenchymal tissues requires the recruitment of MSCs to bring about regeneration and wound healing. This is of particular importance in orthopedics which constitutes the largest clinical segment of mesenchymally related tissue treatments. The methods provided can be used to control MSC behavior using engineered growth factors and scaffolds, for example, those that have one or more of the ligand dimers provided attached thereto.

Exogenous materials are widely used clinically for bone regeneration. Surgical techniques incorporating materials in mandibular bone were pioneered by Bränemark in the 1950s. Today, auto- and allo-grafts as well as synthetic β-tricalcium phosphate (BTCP) and hydroxylapatite (HA) are common materials in bone regeneration procedures, particularly for non-load bearing small or medium bone defects. These approaches all rely on the recipient's own MSC population to bring about tissue regeneration and often involve impregnation of the matrix with extracted bone marrow to seed an appropriate number of MSCs. In current clinical practice autologous bone marrow aspirate containing MSCs has been used as a source of progenitors in both ceramic and demineralized bone grafts. Further, the success of bone grafts in canine models of spinal fusion and segmental defect can be increased by using methods which selectively retain MSCs and exclude non-progenitor cells. These methods have shown significant improvement in outcomes over less invasive interventions, presumably due to the role of MSC delivery to the site of injury. The treatment of implants with bioactive components such as growth factors represents a growing area of study and is likely to extend the benefits achieved thus far with MSC enrichment.

Bone morphogenetic proteins (BMPs) and many other growth factors have gained clinical acceptance in orthopedic medicine and are in various stages of pre-clinical development. BMPs, like most growth factors, are typically delivered soluble or adsorbed to a matrix, which creates great variability in local retention and release. Further, BMPs act on bone-forming cells to foster differentiation toward the osteogenic phenotype, hence they are arguably less effective in large defects that have a clinical deficiency of MSC. Members of the EGFR family act on stem cells and early progenitor cells, hence interventions targeted to this family can increase survival and proliferation of cells at a stage that feeds into the steps influenced by BMPs.

During early stages of development bone begins to nucleate at ossification centers within a cartilage "model". The origin of these early osteogenic cells is the embryonic mesenchyme. Ossification extends outward from primary nodes guided by gradients in differentiation stimuli which include numerous cytokines, growth factors, small molecules, and juxtacrine interactions. Later in development (postnatal) secondary nodes of ossification emerge at the ends of long bones and likewise extend outward. Eventually the primary and secondary ossification fronts meet at the epiphysial plate, a cartilaginous remnant that is eventually ossified. Many aspects of later developmental processes leading to mature bone and cartilage remain uncharacterized. Details such as the vascularization of trabecular bone have yet to be elucidated. However, early bone development from cartilaginous tissue is reasonably well characterized and can be used to inform approaches to the early regeneration of these tissues in a wound healing context. Presentation of the correct cues early in the wound healing process is important for proper tissue regeneration. The cues arising from Her receptor stimulation are particularly important in this regard. Therefore, the ligand dimers can be used to regenerate bone and cartilage. Methods of doing so are also provided. The ligand dimers can be applied to bone or cartilage or can be on a tissue scaffold placed in contact with the bone or cartilage.

Many studies have characterized the varied effects of EGF on tissues in vitro and in vivo. EGF is the canonical ligand for Her-1 and can bring about proliferation, migration, homeostasis, and synergistic effects leading to differentiation, for example, when dosed with other ligands. The broad effects of this ligand are due to the large number of tissues in which Her-1 is expressed and the diversity of the downstream signaling network, thus making EGF an important stimulus in wound healing contexts.

In MSCs, EGF has been shown to affect a number of cell behaviors in a context specific manner. EGF can promote proliferation, osteogenic differentiation, and survival. EGF has been shown to exert different effects on human telomerase immortalized MSCs (hTMSCs) and primary rat MSCs. It has also been found that survival enhancement can be achieved with the surface tethering of EGF. In a wound healing context EGF can serve as an important cue leading to bone development and homeostasis following surgery. EGF has also been shown to play a role as a regulator of CTP behavior and can also give rise to expansion of MSCs without inducing differentiation. In addition to its potential in wound healing applications, EGF has a high degree of receptor specificity for Her-1 and offers a mechanism for control over Her-1 receptor dimerization.

The effects of neuregulin-1β (NRG1) which is the canonical ligand for Her-3 are well characterized in neurogenesis and neurological development. Most notably NRG1 can induce neural differentiation of rat pheochromocytoma (PC12) cells. Its role in neuromuscular junction (NMJ) formation is also well characterized where it serves to stimulate acetylcholine receptor (AChR) expression at the NMJ synapse. NRG1 has also been shown to enhance the ability of MSCs to repair damaged muscle tissues, thus implicating NRG1 as a potential myogenic stimulus.

It has also been indicated that NRG1 has a protective effect on MSCs exposed to hypoxic or serum deprived conditions. Protection of MSCs in hypoxic environments is of importance following surgical intervention where seeding of MSCs into large defects will necessarily lead to hypoxic conditions in a large segment of the wound before vascularization occurs. In addition to its being a differentiation and hypoxia protective ligand, NRG1 has a high degree of receptor specificity for Her-3 and like EGF offers a mechanism for control over Her-3 receptor dimerization.

The ligand dimers can be used in soluble form or can be tethered to a substrate, such as a matrix or tissue scaffold. These ligand dimers may be attached to the substrates using a linker. The substrate may be spherical, as in a bead, or cylindrical, as in a test tube or rod. Alternatively, the substrate may be flat such as a sheet, test strip, a microplate, etc. Therefore, also provided herein are compositions comprising the ligand dimers tethered to a substrate, such as a matrix or scaffold, as are methods for contacting cells with the ligand dimers tethered to such substrates.

The compositions provided have diverse applications in therapeutics involving tissue engineering, regenerative medicine, anti-cancer compounds, etc. and hence offer improvements in several ways. Methods for treating the various indications provided herein are also provided. The major advantage is quantitative control of receptor dimerization and activation—or inhibition of such. The ligand dimers can be highly specific for the intended targets as they can be based on the natural high-affinity ligands that exist physiologically. Further, the ligand dimers can have advantages over small molecule kinase inhibitors, in part due to specificity, but also due to the ability to target receptors that have mutations and do not respond appropriately to small molecule inhibitors. Regarding the use of the ligand dimers to stimulate regenerative behaviors in cells and tissues, the ligand dimers can have advantages in quantitative control of signaling interactions that can foster pro-survival signaling in inflammatory environments, or foster differentiation.

The compositions as described herein can be used to prevent or treat a "neurological disorder/disease" defined herein as a disorder or disease in which damages or loss, e.g., progressive loss, of neurons occurs either in the peripheral nervous system or in the central nervous system. Examples of neurological disorders include familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS dementia, age related dementia, age associated memory impairment, amyloidosis-related neurological diseases such as those caused by the prion protein (PrP) which is associated with transmissible spongiform encephalopathy (Creutzfeldt-Jakob disease, Gerstmann-Straussler-Scheinker syndrome, scrapie, bovine spongiform encephalopathy and kuru), and those caused by excess cystatin C accumulation (hereditary cystatin C angiopathy), traumatic brain injury (e.g., surgery-related brain injury), cerebral edema, peripheral nerve damage, spinal cord injury, Wernicke-Korsakoff's related dementia (alcohol induced dementia), and presenile dementia. The foregoing examples are not meant to be comprehensive but serve merely as an illustration of the term "neurological disorder/disease".

Provided herein, therefore, are also methods of treatment or prevention of a neurological disorder/disease comprising the administration of one or more ligand dimers possibly in conjunction with other therapeutic agents for the particular condition being treated.

The administration of other therapeutics may be performed concomitantly, sequentially or at different time points.

For example, when treating Alzheimer's Disease, the therapeutic agents which can be combined with the ligand dimers provided include, but are not limited to, estrogen, vitamin E (alpha-tocopherol), Tacrine (tetrahydroacridinamine), selegiline (deprenyl), and Aracept (donepezil). One of ordinary skill in the art will be familiar with additional therapeutic agents useful for the treatment of neurological disorders/diseases.

The compositions provided herein can also be used in methods of repairing tissues or wound healing. Regulation of proliferation and/or apoptosis with the compositions provided can be beneficial in the treatment of a variety of disorders/diseases whereby an increase or decrease in cell proliferation and/or cell death is warranted. The ligand dimers provided can be used to regenerate tissue rather than scar after injury, or recover from chronic injury, through inhibitory effects on TGFβ and other chronic inflammatory mediators. Examples include pulmonary fibrosis, liver fibrosis, epithelial (skin scarring). The EGFR is prominently expressed in intestine and the GI tract lining cells, hence, the ligand dimers provided can be used in the healing of chronic inflammation, such as Crohn's disease. Provided herein, therefore, are methods of treating these disorders/diseases or effecting the aforementioned therapeutic outcomes by administering one or more ligand dimers to a subject in need thereof. Further, methods are provided whereby any of the aforementioned cells or cells associated with these disorders/diseases are contacted with one or more of the ligand dimers provided herein.

The compositions provided can further comprise another wound healing agent. Such agents are known to those of ordinary skill in the art and include cytokines, growth factors, etc. Methods are provided whereby a wound or tissue in which regeneration is desired is contacted with one or more of the ligand dimers provided herein. In some embodiments, the wound or tissue is also contacted with another wound healing agent.

The compositions and methods provided can further comprise another anti-inflammatory agent or the administration of another anti-inflammatory agent. Such agents are known to those of ordinary skill in the art and include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; and Zomepirac Sodium.

Methods are also provided whereby a subject with an inflammatory disease is administered one or more of the ligand dimers provided herein in order to treat the disease. In some embodiments, the subject is also administered another anti-inflammatory agent. In some embodiments, the inflammatory disease is non-autoimmune inflammatory bowel disease, post-surgical adhesions, coronary artery disease, hepatic fibrosis, acute respiratory distress syndrome, acute inflammatory pancreatitis, endoscopic retrograde cholangiopancreatography-induced pancreatitis, burns, atherogenesis of coronary, cerebral and peripheral arteries, appendicitis, cholecystitis, diverticulitis, visceral fibrotic disorders, wound healing, skin scarring disorders (keloids, hidradenitis suppurativa), granulomatous disorders (sarcoidosis, primary biliary cirrhosis), asthma, pyoderma gandrenosum, Sweet's syndrome, Behcet's disease, primary sclerosing cholangitis or an abscess. In still another embodiment the inflammatory disease is an autoimmune condition. The autoimmune condition in some embodiments is rheumatoid arthritis, rheumatic fever, ulcerative colitis, Crohn's disease, autoimmune inflammatory bowel disease, insulin-dependent diabetes mellitus, diabetes mellitus, juvenile diabetes, spontaneous autoimmune diabetes, gastritis, autoimmune atrophic gastritis, autoimmune hepatitis, thyroiditis, Hashimoto's thyroiditis, insulitis, oophoritis, orchitis, uveitis, phacogenic uveitis, multiple sclerosis, myasthenia gravis, primary myxoedema, thyrotoxicosis, pernicious anemia, autoimmune haemolytic anemia, Addison's disease, scleroderma, Goodpasture's syndrome, Guillain-Barre syndrome, Graves' disease, glomerulonephritis, psoriasis, pemphigus vulgaris, pemphigoid, sympathetic opthalmia, idiopathic thrombocytopenic purpura, idiopathic feucopenia, Sjogren's syndrome, Wegener's granulomatosis, poly/dermatomyositis or systemic lupus erythematosus.

Apoptosis is known to play a role in numerous physiologic and pathologic events such as embryogenesis and metamorphosis, hormone-dependent involution in the adult, cell death in tumors, atrophy of some organs and tissues, etc.

The compositions provided herein can also be used to promote cell death, such as cancer cell death, and, therefore, can be used to treat cancer. They can also be used to treat other cancer-like diseases characterized by inappropriate cell proliferation, such as endometriosis. Methods of treating cancer-like diseases, such as endometriosis, by administering one or more ligand dimers to a subject that has the cancer-like disease are also provided herein. In some embodiments, the compositions provided herein can be used to inhibit cell death.

The compositions provided are useful for treating and preventing cancer cell proliferation and metastasis. Thus, methods are provided for treating subjects having cancer. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

Screening assays are also provided for identifying ligand dimers that enhance or inhibit signaling e.g., for the treatment of a tumor and/or for preventing metastasis. The assays are accomplished, for example, by contacting cells that express at least one type of Her receptor and determining whether or not the desired homo- or hetero-dimerization occurs and/or signaling is enhanced or inhibited. In the case of treatment of a disorder/disease, such as cancer, the assays may also be accomplished by treating a tumor or isolated tumor cells with one or more ligand dimers and determining the effects (e.g., determining whether or not cell proliferation, metastasis, differentiation, etc. occurs). It follows, that similar assays can be performed to assess the ability of one or more ligand dimers to regenerate tissue, treat a wound, etc.

The ligand dimers can have therapeutic activity in the inhibition of tumor cell proliferation and metastasis. The invasion and metastasis of cancer is a complex process which involves changes in cell adhesion properties which allow a transformed cell to invade and migrate through the extracellular matrix (ECM) and acquire anchorage-independent growth properties (Liotta, L. A., et al., Cell 64:327-336, 1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus the ligand dimers can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer, 1992, 52:378-383. Matrigel is a reconstituted basement membrane containing type IV collagen, laminin, heparan sulfate proteoglycans such as perlecan, which bind to and localize bFGF, vitronectin as well as transforming growth factor-$\beta$ (TGF-$\beta$), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

When administered to a patient undergoing cancer treatment, the ligand dimers may be administered in cocktails containing one or more other types of ligand dimers and/or other anti-cancer agents. The compounds may also be administered in cocktails containing agents that treat the side-effects of radiation therapy, such as anti-emetics, radiation protectants, etc.

Other anti-cancer drugs that can be administered with the ligand dimers of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Effective amounts of the ligand dimers provided are administered to a subject in need of such treatment. Effective amounts are those amounts which will result in a desired improvement in the condition or symptoms of the condition, e.g., for cancer this is a reduction in cellular proliferation or metastasis, without causing other medically unacceptable side effects. Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

The terms "treat" and "treating" as used herein refers to reversing or blocking the progression of the disorder/disease in the subject. Treating a disorder/disease also includes exacting a desired improvement in the disorder/disease or symptoms of the disorder/disease. For example, to treat a subject with tumor cell proliferation refers to inhibiting completely or partially the proliferation or metastasis of a cancer or tumor cell, as well as inhibiting or preventing any increase in the proliferation or metastasis of a cancer or tumor cell.

A "subject having a disorder/disease" is a subject that can be diagnosed as having the disorder/disease, e.g., a person having cancer is identified by the presence of cancerous cells.

In general, when administered for therapeutic purposes, the formulations provided are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions provided may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the subject matter provided herein. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); and parabens (0.01-0.25% W/V).

Provided herein are pharmaceutical compositions, for medical use, which comprise a ligand dimer together with one or more pharmaceutically acceptable carriers and optionally other therapeutic ingredients. The term "pharmaceutically-acceptable carrier" as used herein, and described more fully below, means one or more compatible solid or liquid filler, diluents or encapsulating substances which are suitable for administration to a human or other animal. As used herein, the term "carrier" denotes an organic or inorganic ingredient, natural or synthetic, with which the active ingredient is combined to facilitate the application. The components of the pharmaceutical compositions also are capable of being commingled with a ligand dimer or other composition, and with each other, in a manner such that there is no interaction which would substantially impair the desired pharmaceutical efficiency.

A variety of administration routes are available. The particular mode selected will depend, of course, upon the particular active agent selected, the particular condition being treated and the dosage required for therapeutic efficacy. The methods provided, generally speaking, may be practiced using any mode of administration that is medically acceptable, meaning any mode that produces effective levels of a desired response without causing clinically unacceptable adverse effects. A preferred mode of administration is a parenteral route. The term "parenteral" includes subcutaneous injections, intravenous, intramuscular, intraperitoneal, intra sternal injection or infusion techniques. Other modes of administration include oral, mucosal, rectal, vaginal, sublingual, intranasal, intratracheal, inhalation, ocular, transdermal, etc.

For oral administration, the compounds can be formulated readily by combining the active compound(s) with pharmaceutically acceptable carriers well known in the art. Such carriers enable the compounds to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described elsewhere herein, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The compositions may conveniently be presented in unit dosage form and may be prepared by any of the methods well known in the art of pharmacy. All methods include the step of bringing the ligand dimers into association with a carrier which constitutes one or more accessory ingredients. In general, the compositions are prepared by uniformly and intimately bringing the ligand dimers into association with a liquid carrier, a finely divided solid carrier, or both, and then, if necessary, shaping the product. The compositions may be stored lyophilized.

Other delivery systems can include time-release, delayed release or sustained release delivery systems. Such systems can avoid repeated administrations of the ligand dimers provided, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

The ligand dimers provided herein may also be linked to a targeting molecule. A targeting molecule is any molecule or compound which is specific for a particular cell or tissue and which can be used to direct the ligand dimer to the cell or tissue. For example, the targeting molecule can be a molecule which specifically interacts with a cancer cell or a tumor. For instance, the targeting molecule may be a protein or other type of molecule that recognizes and specifically interacts with a tumor antigen.

Tumor-antigens include Melan-A/MART-1, Dipeptidyl peptidase IV (DPPIV), adenosine deaminase-binding protein (ADAbp), cyclophilin b, Colorectal associated antigen (CRC)—0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, Imp-1, EBV-encoded nuclear antigen (EBNA)-1, and c-erbB-2.

A subject can be any human or non-human vertebrate, e.g., mouse, rat, dog, cat, horse, cow, pig.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Protein Design and Characterization

The design of ligands was guided by the dimerization geometry of Her receptors when bound to ligand. This geometry is illustrated by the 2 Å crystal structure of EGF-bound homodimerized extracellular domain of Her-1 (PDB:1IVO).

It was shown that the ligands assume an anti-parallel orientation with respect to their termini and the distance between ligands is ~10 nm.

As an example, a modular protein design can facilitate the investigation of homo- as well as heterodimers in both Her-1 and Her-3 without requiring exhaustive and repetitive cloning, expression, and purification. The bivalent design with modularity can be realized by using a tight binding region that brings ligands together with the correct orientation and spacing to permit simultaneous receptor dimer binding.

A coiled coil domain allowed for a cognate coil containing ligand to form a bivalent construct. The coil sequences have been reported by several investigators to exhibit a Kd as low as $10^{-15}$ M. The coils are separated from the ligand by a protease resistant spacer designed by Sauer et al. that confers flexibility, solubility, and together with the coils a sufficient extension to bridge a gap 20 nm long. This distance is twice the distance between the most extreme termini in EGFs bound to dimeric Her-1. A schematic of the bivalent ligand is shown in figures, which also depicts additional functional moieties, including antibody detection epitopes, and a biotin acceptor peptide (BAP) sequence to permit biotinylation and subsequent immobilization on neutravidin coated matrices.

A number of peptides have been expressed, purified, and shown to exhibit the expected pM dissociation constants. Obtaining high yield following refolding of bioactive EGF and NRG1 has been challenging. In particular, the expression of EGF and NRG1 in the pET28(a) expression system (C1 and C4, respectively) has proven difficult due to the large fraction of protein that remains in inclusion bodies. Various protocols to recover this fraction have been tried with limited success. This has resulted in small amounts of C1 and C4 being available for experiments. In contrast C2 and C3 (EGF and NRG1, respectively) are expressed in the pMAL system and this results in much higher recovery of ligand.

Bioactivity of Soluble Monovalent Forms of the Ligands and the Formation of Ligand Dimers and Characterization of Stability Under Culture Conditions Ligand bioactivity has been confirmed by phospho-protein assays which measured the phosphorylation of ERK or of Her receptors. The pERK node is a convenient indicator of bioactivity because it is downstream of both EGF and NRG signaling and the extent of activation is dose dependent. Changes in the levels of pERK have been measured by immunoblot, in cell Western (ICW) and BIOPLEX assay. The dose response of monovalent ligands has been compared to that of commercially available EGF and NRG1 to determine relative bioactivity. Apart from dose response, time course assays of pERK signaling have been used as an indicator of bioactivity.

Cell lines used to assay pERK activation include HeLa, MCF-7 and hTMSC. HeLa cells are well established as a suitable line in which to measure EGF activity. Likewise, hTMSCs express Her-1 and show a characteristic dose response to EGF.

Both MCF-7s and HeLa cells exhibit pERK activation following NRG stimulation. In HeLa cells the extent of pERK activation is lower when compared with EGF stimulation. This is expected since Her-3 and Her-4 are normally not detectable by immunoblot in HeLa cells. Although HeLa cells do exhibit a detectable dose response to NRG1 stimulation, MCF-7s may be a more suitable cell line for this assay. MCF-7s exhibit strong activation of pERK and pHer-3 following NRG stimulation.

Results from monovalent ligand bioactivity characterizations in HeLa cells are shown in the figures. Following the confirmation of bioactivity of monovalent ligands, bivalent ligand dimers have been produced by incubating equimolar amounts of cognate ligands in physiological buffers and allowing coiled coil interactions to form stable dimers. These are then purified by chromatographic methods. The purity and stability of ligand dimers can be confirmed with high resolution analytical size exclusion chromatography (HR-SEC). This characterization can confirm that no residual monovalent ligand is present in bivalent ligand formulations. In addition to the absence of monovalent ligand peaks measured by absorbance at 280 nm, each HRSEC fraction can be assayed by immunoblot to confirm the absence of residual monovalent ligand at the expected elution volumes. Residual monovalent ligand could confound signaling results if present in concentrations greater than 1 pM. Other studies to confirm the binding affinity of cognate ligands can include SPR and ELISA methods.

Ligand Dimers can Exert Control Over the Formation of Her Hetero- and Homodimers To determine that the ligand dimers control dimerization, one or more of the following methods can be used:
1. FRET measurements using e.g., Her-1-CFP: Her-3-YFP fusions
2. Receptor crosslinking and immunoblotting following ligand dosing
3. Immunoprecipitation and immunoblotting following ligand dosing
4. Reporter complementation assay (luciferase or dihydrofolate reductase)

The four methods above represent examples of approaches that can be used to assess the ability of the ligand dimers to force dimerization. As an example, the FRET method is detailed below.

To build the FRET sensor, CFY and YFP as C-terminal fusions to Her-1 and Her-3, respectively, can be subcloned. These two receptors are chosen as examples because the proposed ligand system can putatively stimulate Her-1-Her-3 heterodimers and because detection of heterodimers is more straightforward than homodimers when using a FRET system. The construction of the FRET reporter is accomplished through PCR mutagenesis of plasmids containing Her-1 and Her-3 to introduce the C-terminal fluorescent protein fusions CFP and YFP, respectively. The cloning can also introduce flanking restriction sites to permit subcloning into an expression plasmid. These fused constructs can subsequently be cloned into pMI with a retroviral ψ packaging sequence and an MCSV promoter to permit use in either transient transfection or as a packaging vector in retroviral production. MSCs can then be transiently cotransfected with both reporter fusions. Selection of double positives (CFP+YFP) by FACS may be required to produce an enriched cell population suitable for subsequent FRET microscopy measurements.

The plasmid pMI also permits production of retrovirus for each FRET reporter. MSCs can be coinfected with each receptor-reporter pair to produce stable CFP/YFP expressing cell lines which are enriched by FACS and subjected to FRET measurement under a variety of ligand conditions. Demonstration of ligand dimer control over Her dimerization would come from a statistically significant increase in YFP signal when dosing bivalent EGF-NRG ligand (with appropriate controls). Other cell types which have low or null Her-1 (CHO cells) or Her-3 backgrounds may be required to reduce the amount of endogenous untagged receptor which could deplete signal generating receptor dimer pairs.

Characterization of Proliferation, Migration, and Signaling of Her-dimer Controlling Ligands on Cells in Culture Phenotypic responses to bivalent ligands can depend on the expression level of each receptor in a given cell type. Cell lines with well-characterized expression profiles (e.g., Her and/or integrin expression) and responses to ligands (e.g., Her and/or integrin ligands) are the preferred cell types in which to carry out initial phenotypic characterizations. Although cancer cell lines are generally poor physiological models, these lines can be used to obtain data on a well-defined background (e.g., Her background) which are comparable with extensive prior work studying the receptors (e.g., Her receptors). Two such cell lines are HeLa and MCF-7. HeLa cells have high Her-1 expression with robust response to EGF treatment and low Her-3 and Her-4 expression with weak response to NRG treatment. HeLa cells are routinely used to characterize EGF bioactivity and extensive data are available on the signaling and phenotypes of EGF stimulated HeLa cells. Thus HeLa cells are well-suited to characterize bivalent ligands which contain EGF. In contrast, MCF-7s have high Her-3 and low Her-1 expression levels, exhibit a robust response to NRG stimulation, and have well characterized Her-3 signaling pathways. Thus, MCF-7 cells are well-suited to characterize bivalent ligands which contain NRG. Well-defined Her backgrounds for each cell type can also facilitate comparisons of the effects of the mixed EGF-NRG bivalent ligand.

Activation of the Her-1 homodimer is expected to produce increases in pERK leading to proliferative signaling. This homodimer produces weaker mitogenic signaling than its Her-2 heterodimer and is trafficked via endocytosis at a higher rate than its heterodimers. HeLa cells would likely respond to EGF-EGF (C12) ligand dimers by exhibiting a level of proliferation that is between monomeric EGF stimulated and completely unstimulated HeLa cells. MCF-7 and other Her-3-dependent cancer cell lines are expected to respond to NRG-NRG (C34) ligand dimers by forming Her-3 homodimers thus becoming quiescent or apoptotic due to the kinase deficiency of Her-3 and sequestration of Her-3 receptors into silent complexes.

Bivalent dimers of EGF-NRG can bring together Her-1-Her-3 or Her-1-Her-4 heterodimers and would likely give rise to canonical Her-1 signaling through STAT3 as well as Her-3 mediated PI3K signaling. The phenotypic outcomes resulting from this type of stimulation may also depend on the relative expression levels of the various receptors with respect to each other. The EGF-NRG bivalent ligand can reduce the mitogenic signaling that arises from the free association between Her-2 and Her-3 that normally occurs in cells expressing high amounts of these receptors. The Her-2-3 heterodimer is the most potent mitogenic pair among the Her receptors and modulating this outcome with ligand dimers has importance.

Proliferation can be measured using an end point assay for cell number. Cells stimulated with various ligand conditions for 24, 48 and 72 hours can be counted using the CYQUANT assay. Standard curves can be generated by plating a serial dilution of a known number of cells supplemented with mitomycin-c to prevent proliferation during the overnight incubation required.

Signaling assays have been conducted to measure the dose and temporal response of signaling nodes to ligand stimulation. A principal node common to both EGF and NRG signaling is pERK. Measuring pERK levels following stimulation is a well-characterized signaling metric and has been used to quantify differences resulting from ligand dimer stimulation versus wild-type ligands. Other nodes of interest include phosphorylation of the receptors. For example, measuring phosphorylation levels of all four Her receptors under monomeric and bivalent ligand conditions can provide information regarding the effect of ligand type on receptor dimerization and transactivation. These assays can be accomplished by immuno-blot or in cell Western.

Trafficking of receptors (e.g., Her receptors) is an important component of their regulation. Various receptors have been found to have differential trafficking rates. Unstimulated Her-1 is constitutively internalized at a lower rate than the other Her receptors; however, following stimulation Her-1 homodimers and Her-1-2 heterodimers are internalized at the highest rate of any other Her pair (tchar~4 min vs 30 min). Her-1-1 and Her-1-2 continue to signal as far as the late endosome, and the eventual fate of Her-1 receptors is determined at least in part by the persistence of ligand binding in the endosomal lumen. As compared with other receptors the majority of signaling by Her-1 is accomplished during transit between the cell membrane and the late endosome. The internalization rate of other stimulated receptor dimers (Her-1-3, -2-3, -1-4, -3-4) is much lower and signaling by these is generally localized to the cell membrane. These differences can influence cell signaling as much by localization and persistence as by the particular phosphotyrosine profile arising from specific dimer parings. Thus, the composition of a dimer can influence the trafficking rate; a feature that can be exploited to exert control over signaling. A consequence of biased receptor dimerization by bivalent ligands would be altered trafficking of receptors versus the monovalently stimulated condition. This can be analyzed by tracking the cellular distribution of radiolabeled ligand as a function of time.

Cell migration under the various ligand conditions can be measured by transwell, wound healing, and time-lapse microscopy. Results from some transwell migration experiments are shown in the Figures. A reduction in migration under ligand dimer stimulation is expected given what is known about the signaling potency of Her-1-1, Her-1-3 and Her-3-3 dimers versus other pairings which would result from monomeric ligand stimulation. Further, blockade of Her-2-3 dimer formation has been shown to significantly reduce PI3K mediated migration. Other measures of migration such as wound healing and time-lapse microscopy experiments can be conducted.

Ligand Dimer Design and Characterization

Design, expression, and purification of Her ligand dimers has been performed. Two T7 promoter based expression systems are used to produce the ligands: one is a His-tagged system: pET28(a) (C1EGF, C4NRG1) and the other is a maltose binding protein (MBP) tagged system: pMAL-c2X (C2EGF, C3NRG1). MBP is cleaved from the fusion by factor Xa. Proteins are purified by affinity resins (Ni-NTA for His and amylose resin for MBP) followed by size exclusion chromatography. The pET28a vector tends to produce inclusion bodies which require solubilization in 6 M urea+100 mM dithiothreitol followed by dialysis against a refolding buffer of reduced and oxidized glutathione. The resultant proteins from each of these systems contain cognate coils that bind proteins produced in the other system.

Figure 4:
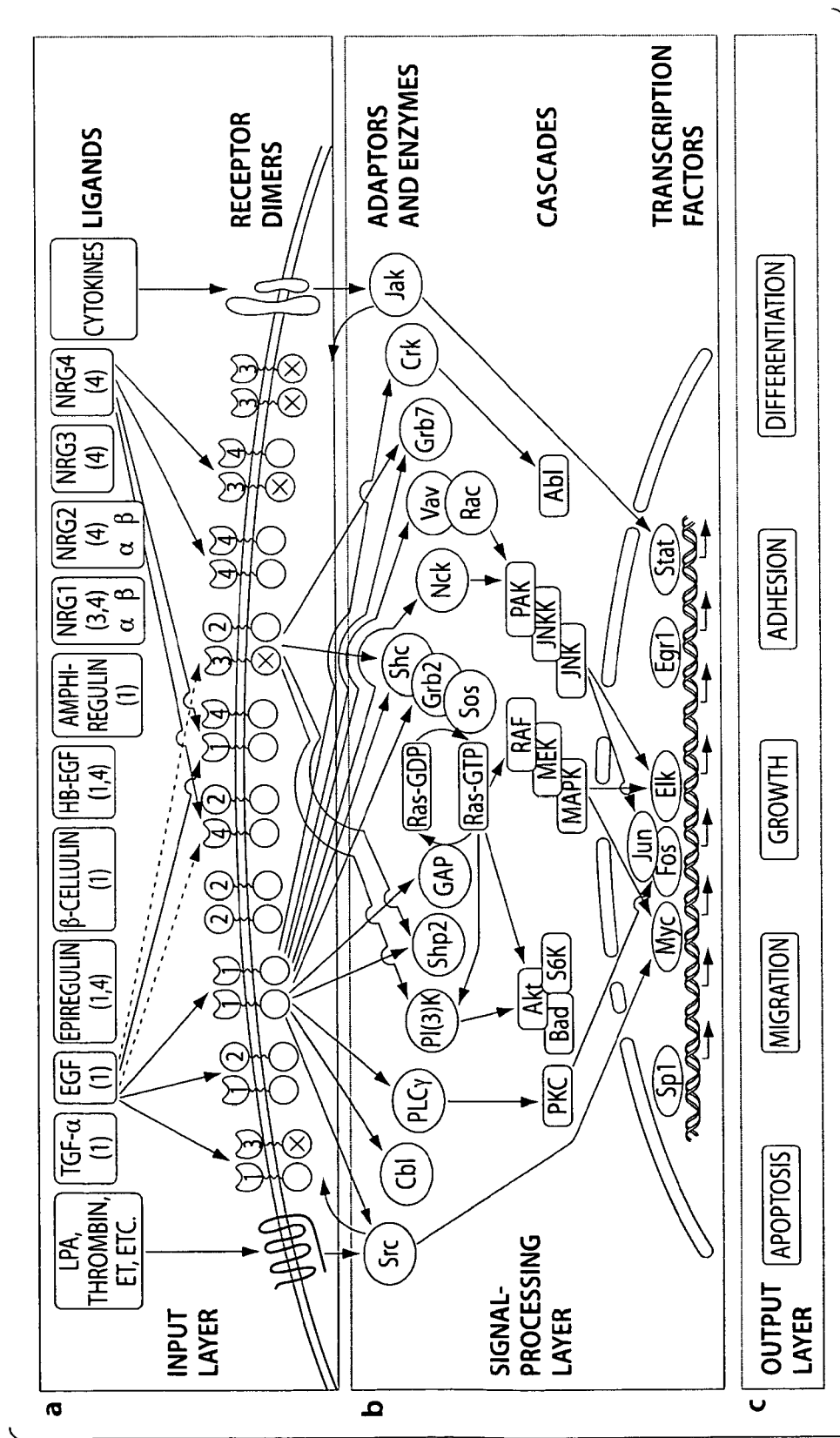
FIG. 4 shows the Her receptor signaling network.
Figure 5A:
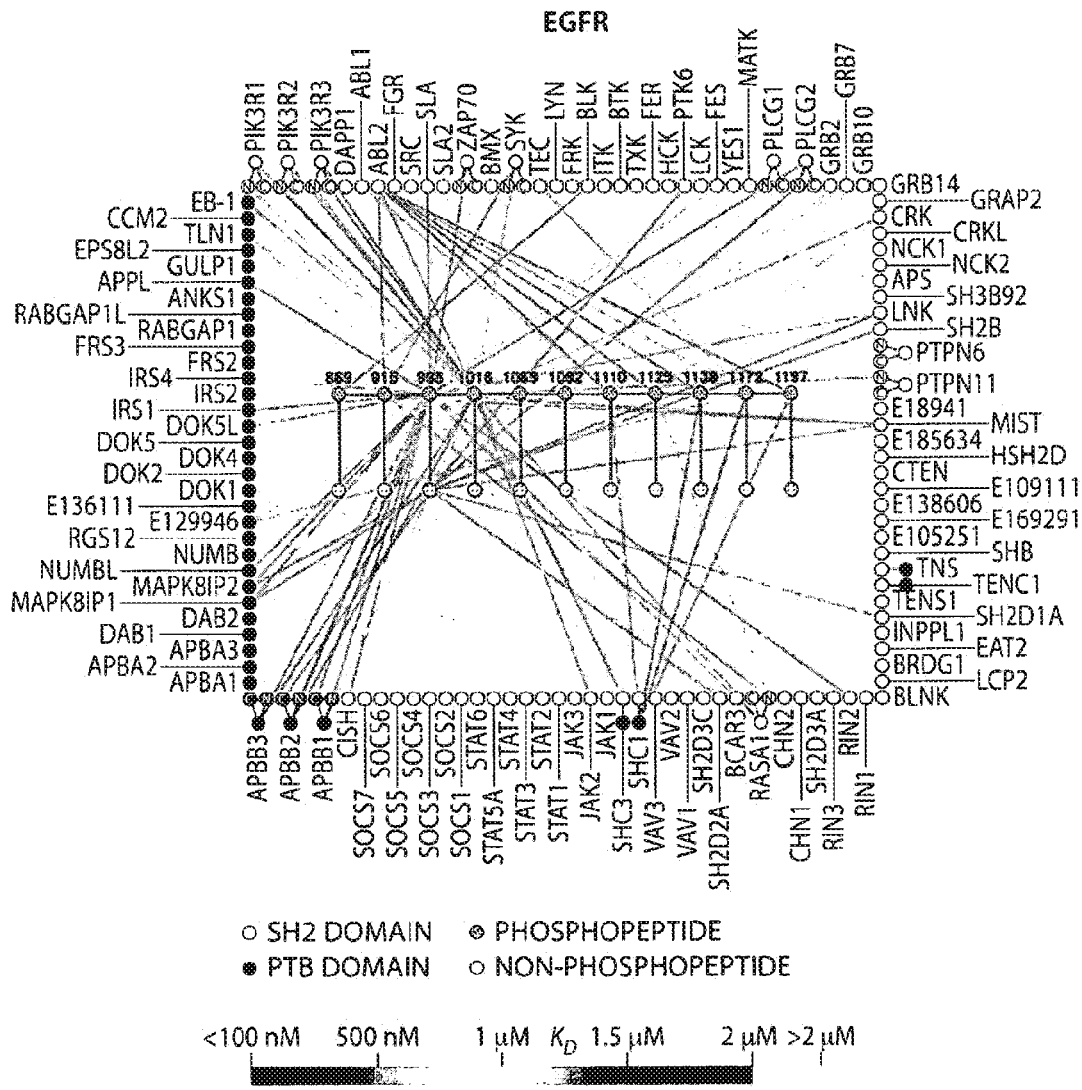
FIG. 5 shows the Her Y/pY interactome for (A) EGFR, (B) ErbB2, (C) ErbB3, and (D) ErbB4.
Figure 5B:
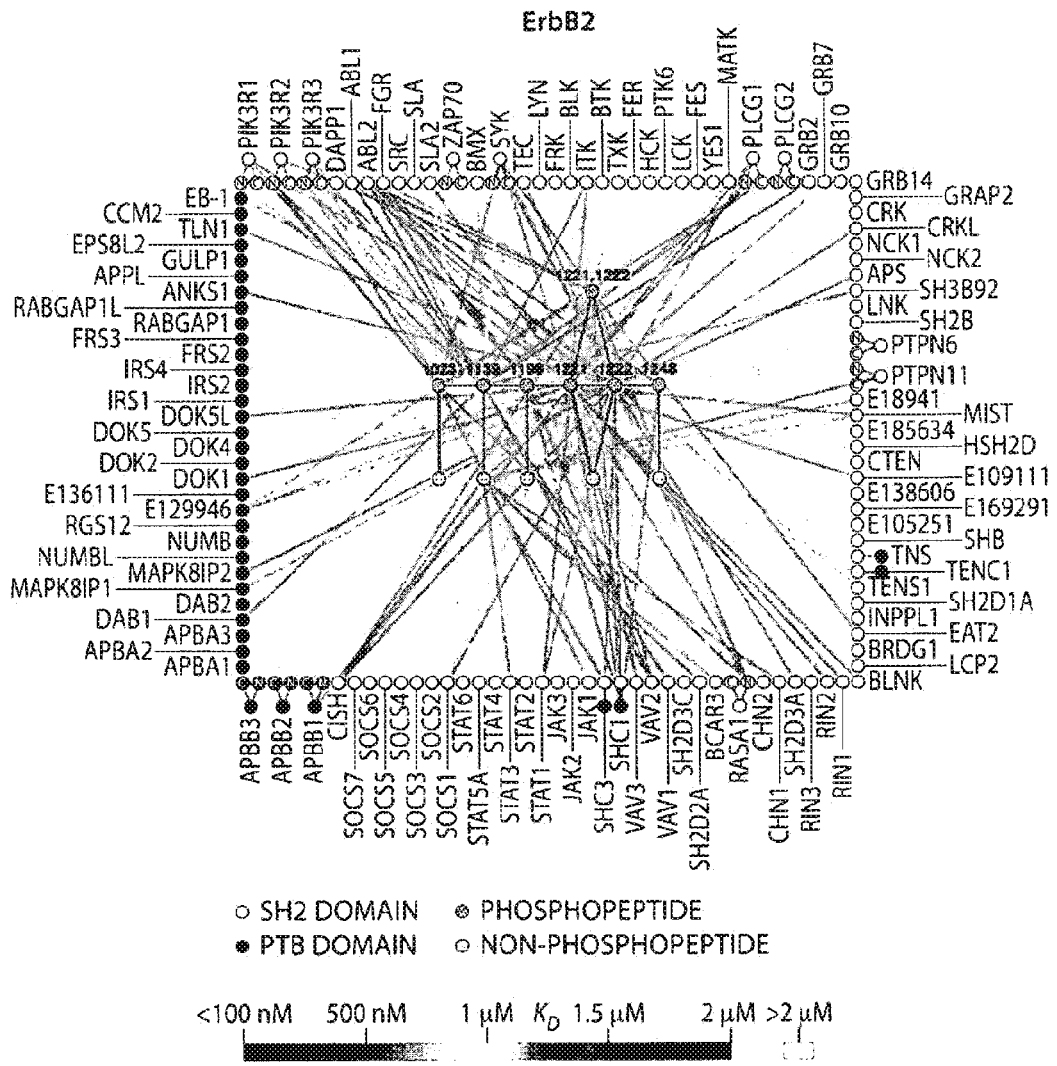
Figure 5C:
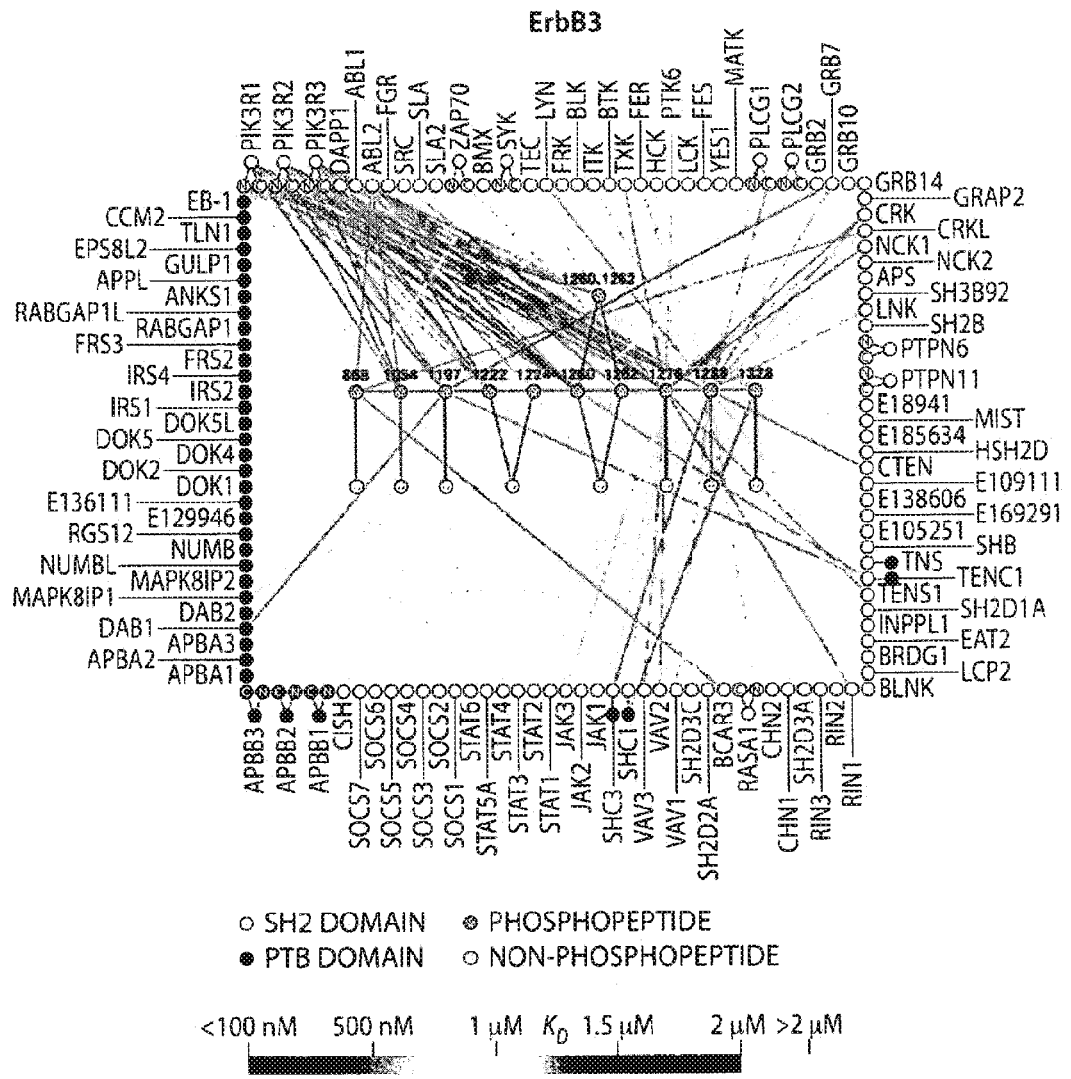
Figure 5D:
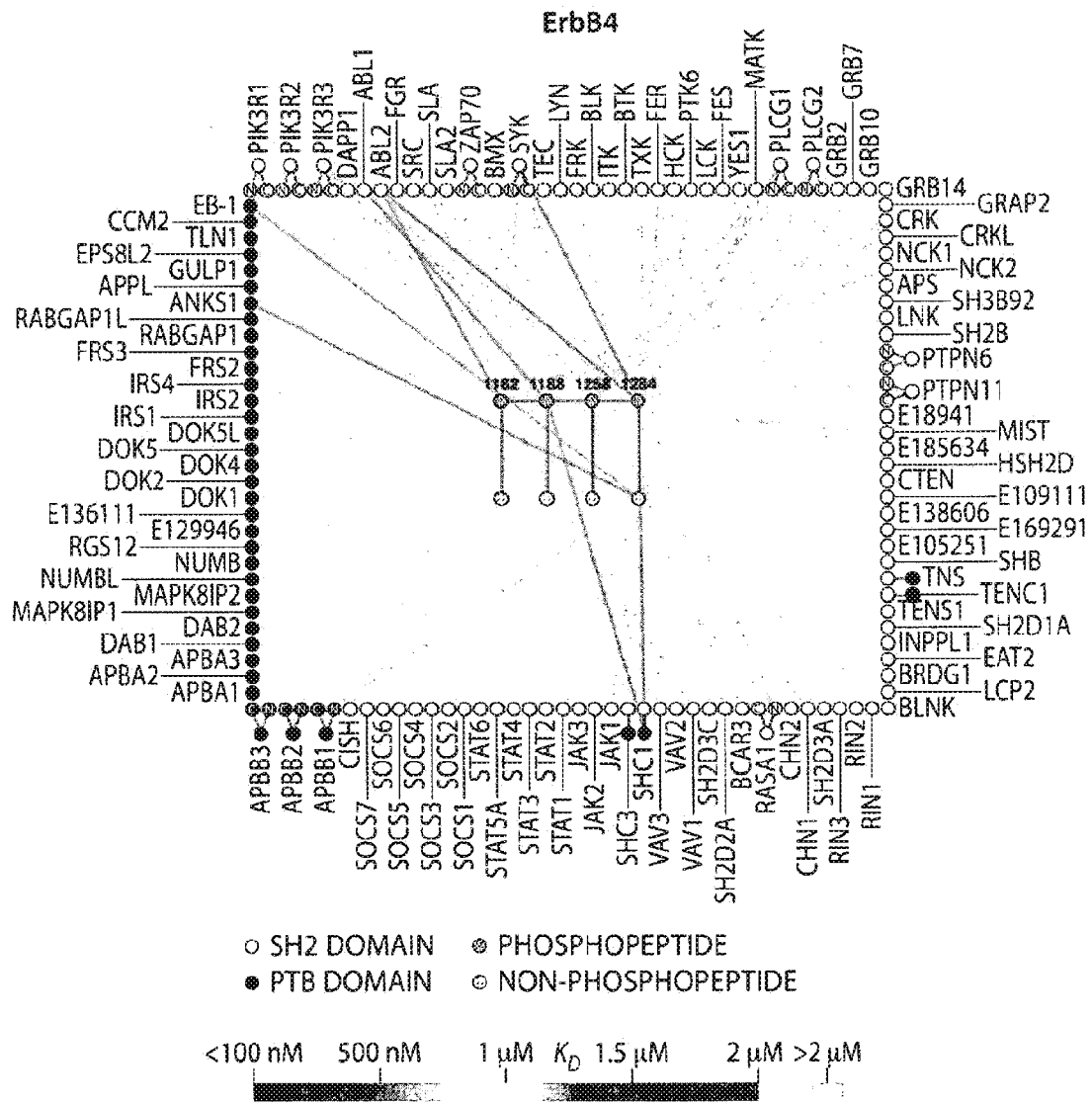
Figure 6:
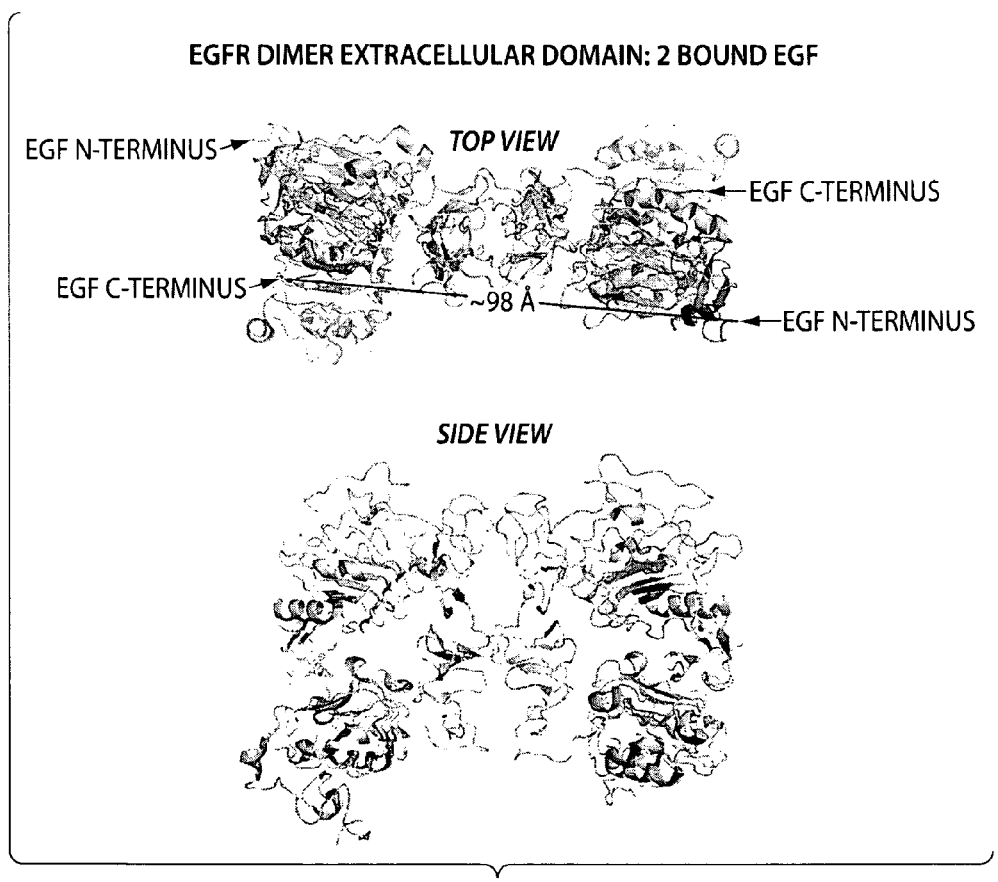
FIG. 6 shows the crystal structure of the Her-1 extracellular domain dimer with two EGF ligands bound and sideview.
Figure 7:
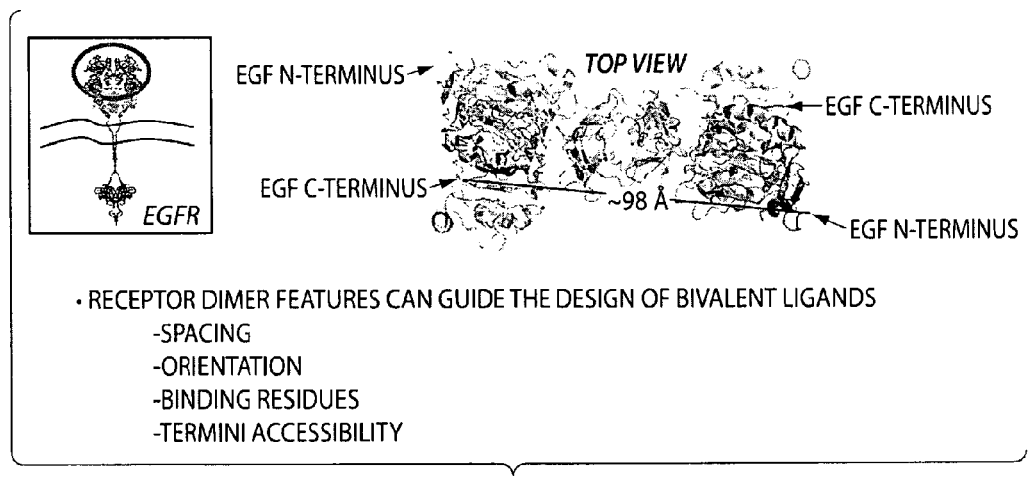
FIG. 7 shows an example of how receptor dimer features can guide the design of ligand dimers.

The first generation of coils selected were as published by Arndt and did not produce acceptable results when assayed. This set of coils was replaced with a modified set of coils by site directed mutagenesis of the original construct. When assayed the new coils yielded a Kd of ~30 pM. This value is ~ two orders of magnitude below the lowest relevant dose of EGF or NRG used in vitro. The modified coils are based on the sequences of the first two peptides described in FIG. 4 (SEQ ID NO: 4 and 5 herein) of Moll, J. R., et al. Protein Science 10, 649 (2001), said peptides are incorporated by reference herein.

The characterization of the coiled coil interaction was performed by immuno-fluorescent binding assay on streptavidin-coated wells. Biotinylated ligand is incubated on the well surface and a titration of cognate coil concentrations is used to generate a binding curve. Controls include non-biotinylated ligand to measure non-specific adsorption and staining of biotinylated ligand with 2° antibody to control for variations in bound ligand. Some results gave a Kd of 30 pM. These results can be confirmed by surface plasmon resonance experiments using a BIACORE2000 instrument. Additional experiments to isolate ligand dimers by high resolution size exclusion chromatography can also be conducted to confirm stability in solution over time courses and buffer conditions relevant to tissue culture experiments.

Results of ligand bioactivity versus commercially available EGF and NRG are shown in the Figures. The singly-dosed ligands produce pERK activation which is indistinguishable from their native counterparts in both duration and magnitude. This assay is indicative of the effectiveness of the refolding and purification methods and validates the use of these ligands for use in dimer experiments.

Putative Her-3-Her-3 Homodimer Effects

Characterization work with the various ligand combinations resulted in consistently low activation of htMSCs by NRG1-NRG1 (designated 'C34') bivalent ligands at doses through 1 μM. This effect was confirmed in subsequent replicates of this experiment. This effect is thought to be a result of the formation of Her-3-Her-3 homodimers which is expected to not produce any signal given the mutual kinase deficiency of this dimer. Two possible models of signal quenching are also shown in the Figures.

Example 2

Design and Synthesis of Bivalent Ligands

Introduction

The approach taken to exert control over Her receptor dimerization was to design a panel of ligands that can recruit specific receptors into dimer complexes based on the affinity and specificity of natural ligand-receptor interactions within the Her receptor family. Such bivalent dimer ligands are expected to bias dimerization.

Protein Design and Characterization

Figure 40:
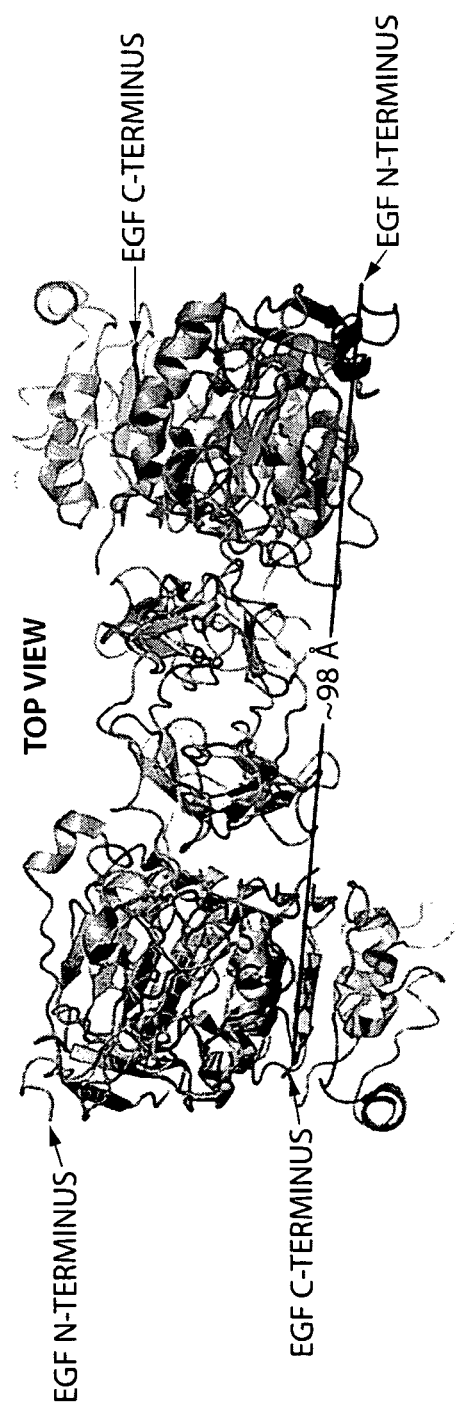
FIG. 40 shows the crystal structure of the Her-1 extracellular domain dimer with two EGF ligands bound.

The design of ligands is first guided by the dimerization geometry of Her receptors when bound to ligand. This geometry is most precisely described by the 2 Å crystal structure of the EGF-bound homodimerized extracellular domain of EGFR (FIG. 40).[71] This figure shows that wild-type ligands assume an anti-parallel orientation with respect to their termini when bound to dimerized receptor and that the distance between ligands is approximately 10 nm.

These features inform the initial design of the bivalent ligand system by imposing constraints on the minimum length between ligand domains and on the relative orientation of ligands once bound to dimerized receptor. Further, the five terminal amino acid residues on both termini of EGF are not captured in the crystal structure, indicating that these residues are unstructured and do not participate in receptor binding. Taken together these features describe the geometric parameters required for bivalent ligand binding. The overall design can accommodate these features.

Modular Bivalent Ligand Design

Figure 8:
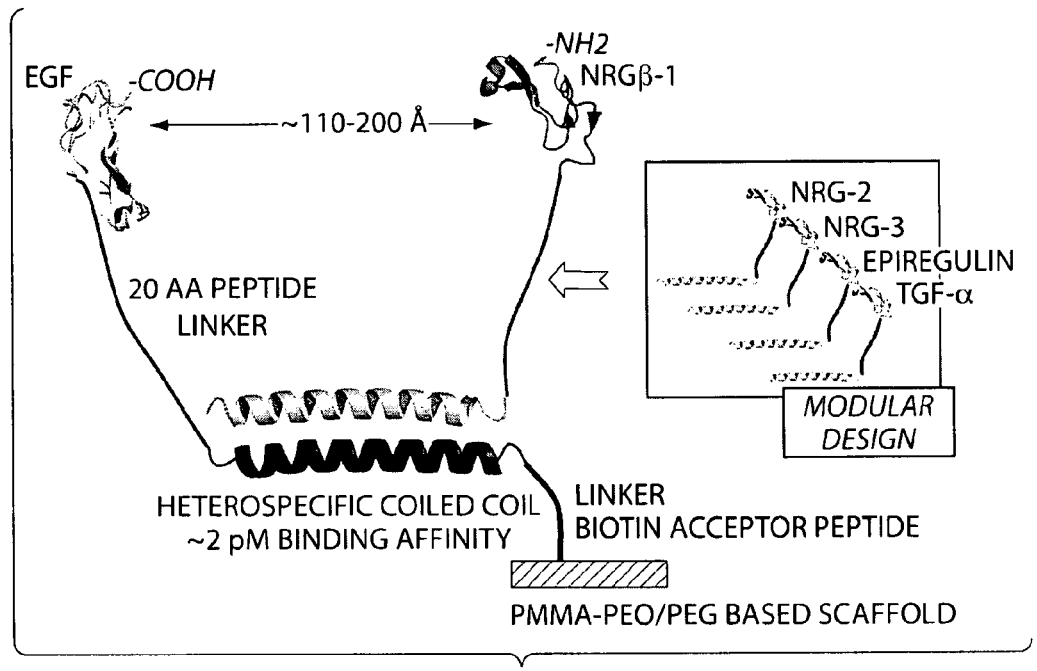
FIG. 8 provides a schematic of a modular peptide system for creating homo-dimers and hetero-dimers of EGFR family ligands. EGF-neuregulin dimer is shown as an example to illustrate possible components and length scales of domains in this engineered dimer peptide and illustrate the ability to create heterodimeric ligand structures. The ligands can be attached to extracellular matrix or to a tissue engineering scaffold via, for example, a linker.
Figure 9:
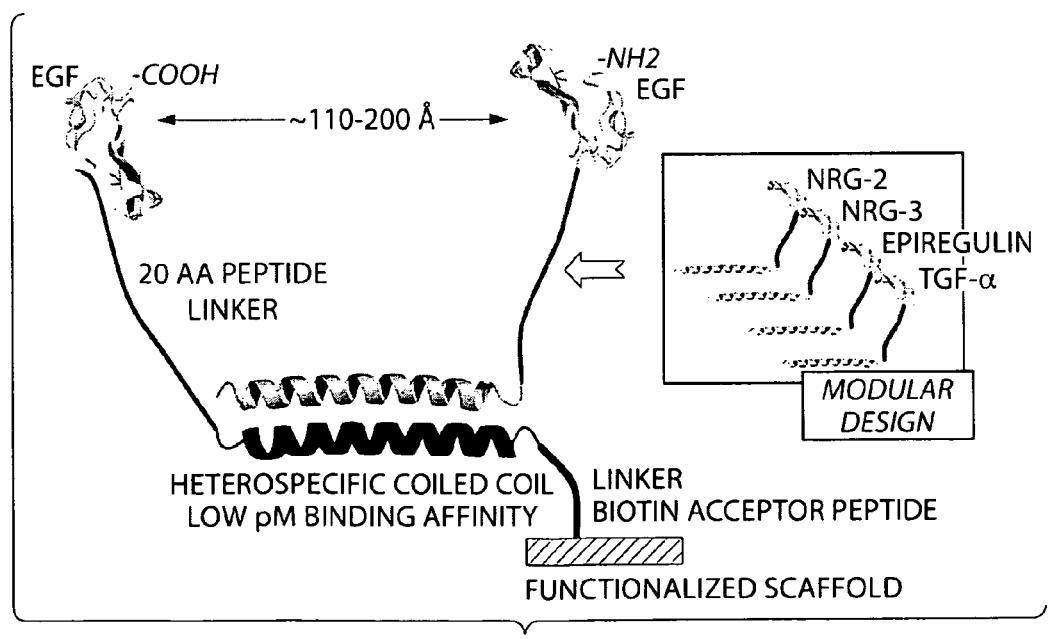
FIG. 9 shows examples of bivalent Her ligand dimer design.
Figure 10:
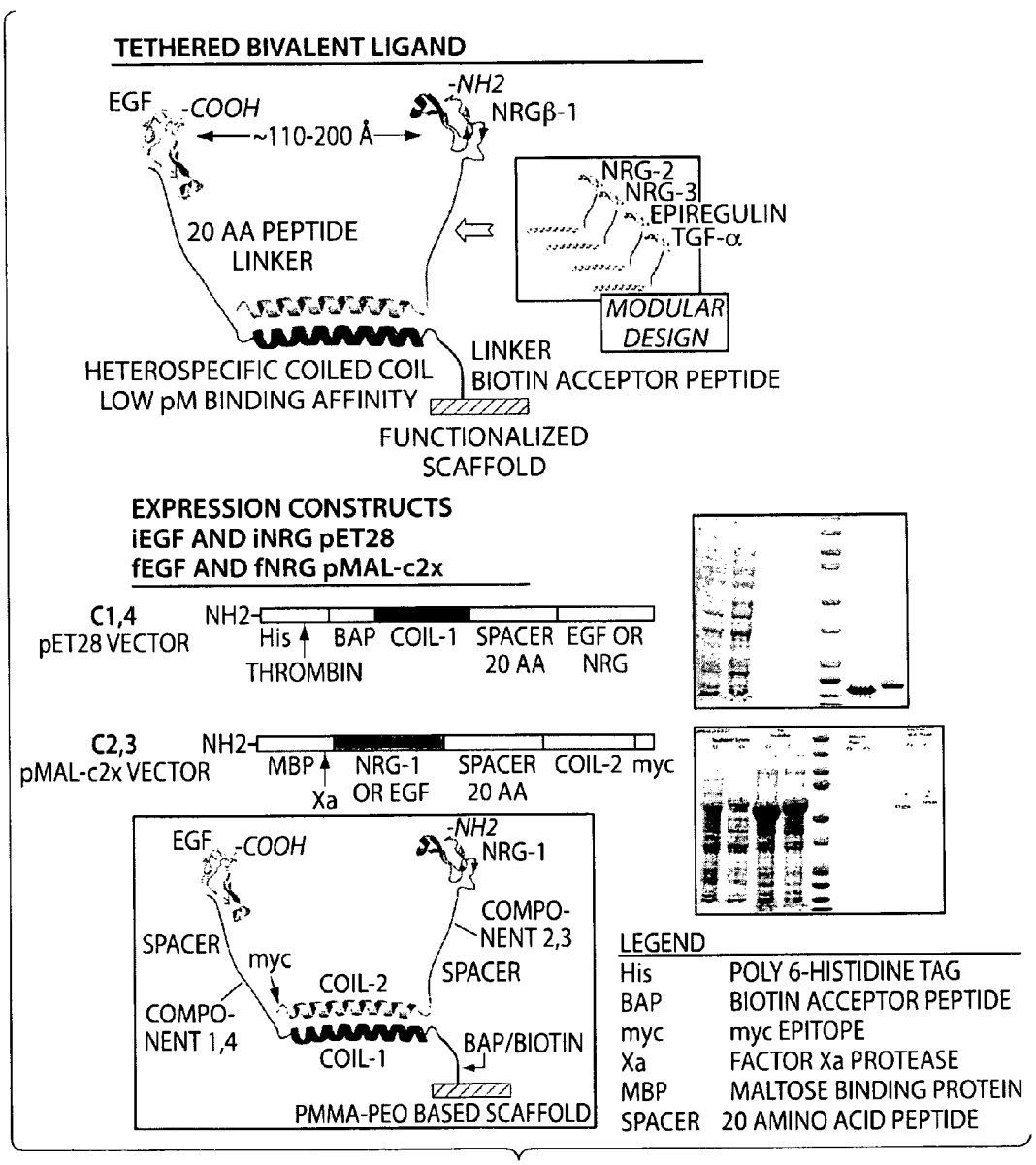
FIG. 10 shows bivalent ligand design and examples of expression constructs used to produce them.
Figure 11:
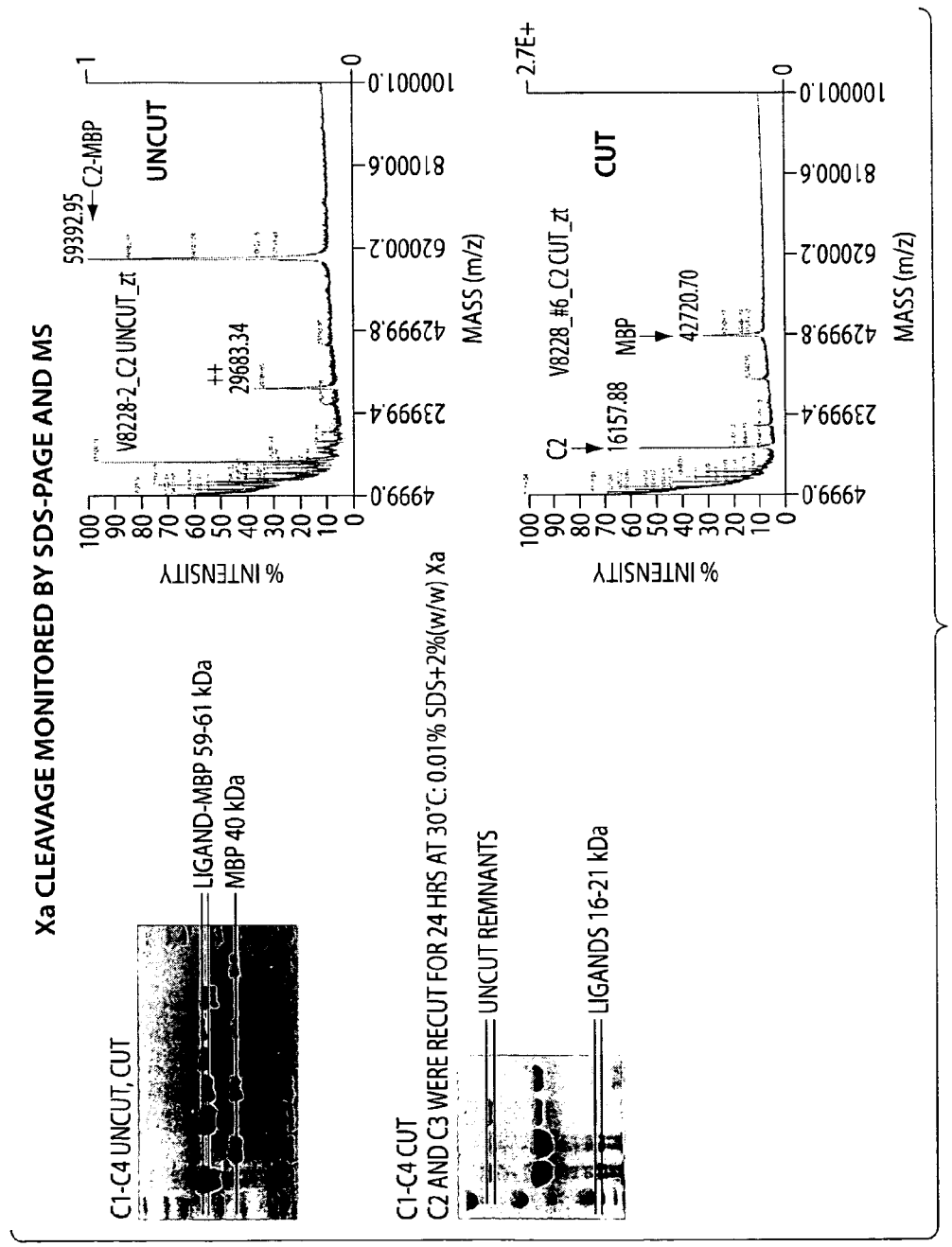
FIG. 11 shows the results of Xa cleavage monitored by SDS-PAGE and mass spectrometry.
Figure 12:
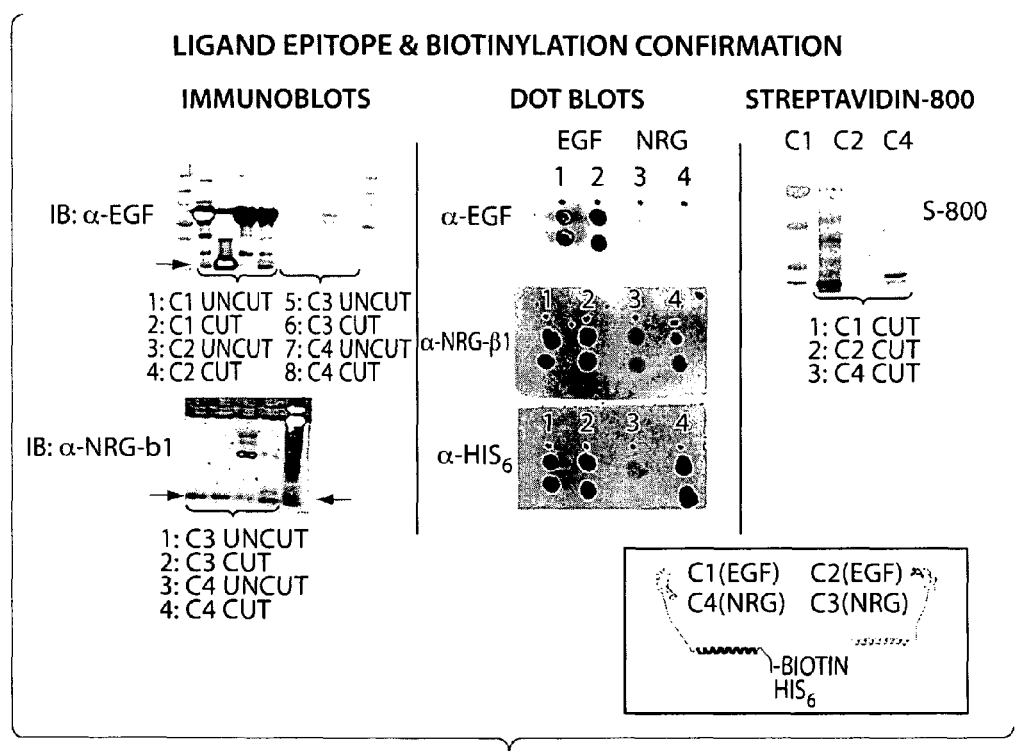
FIG. 12 illustrates ligand epitope and biotinylation confirmation.
Figure 13:
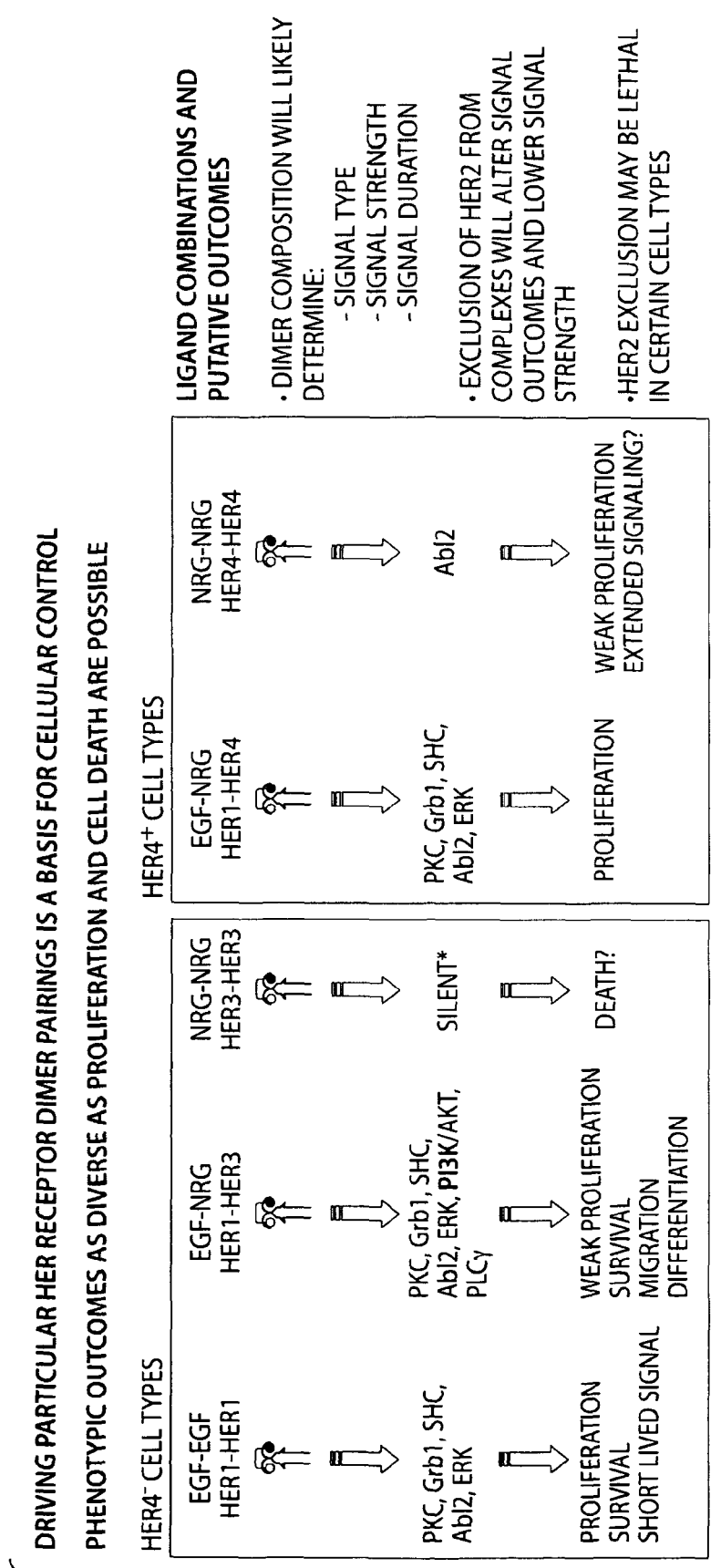
FIG. 13 provides examples of dimer pairs and their expected outcomes.
Figure 14:
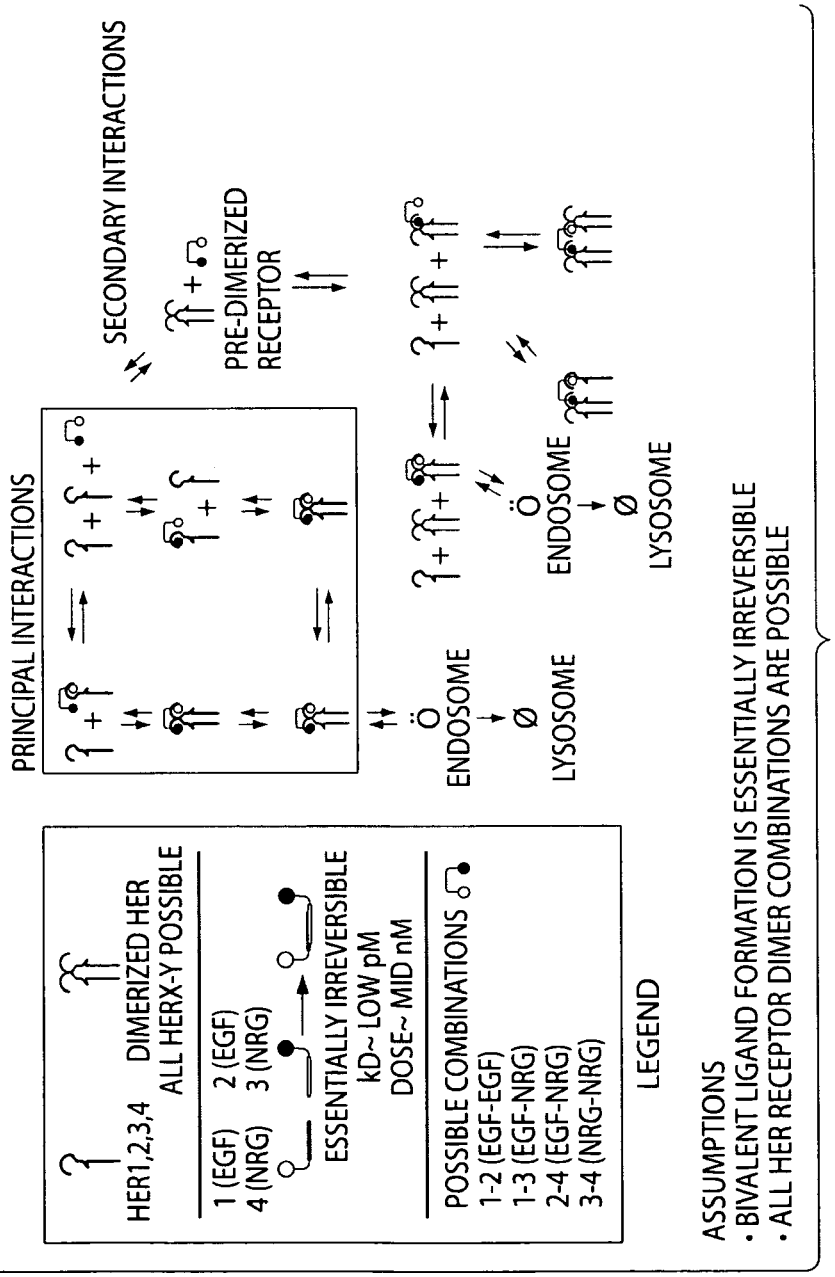
FIG. 14 shows a Her receptor interaction diagram.
Figure 15:
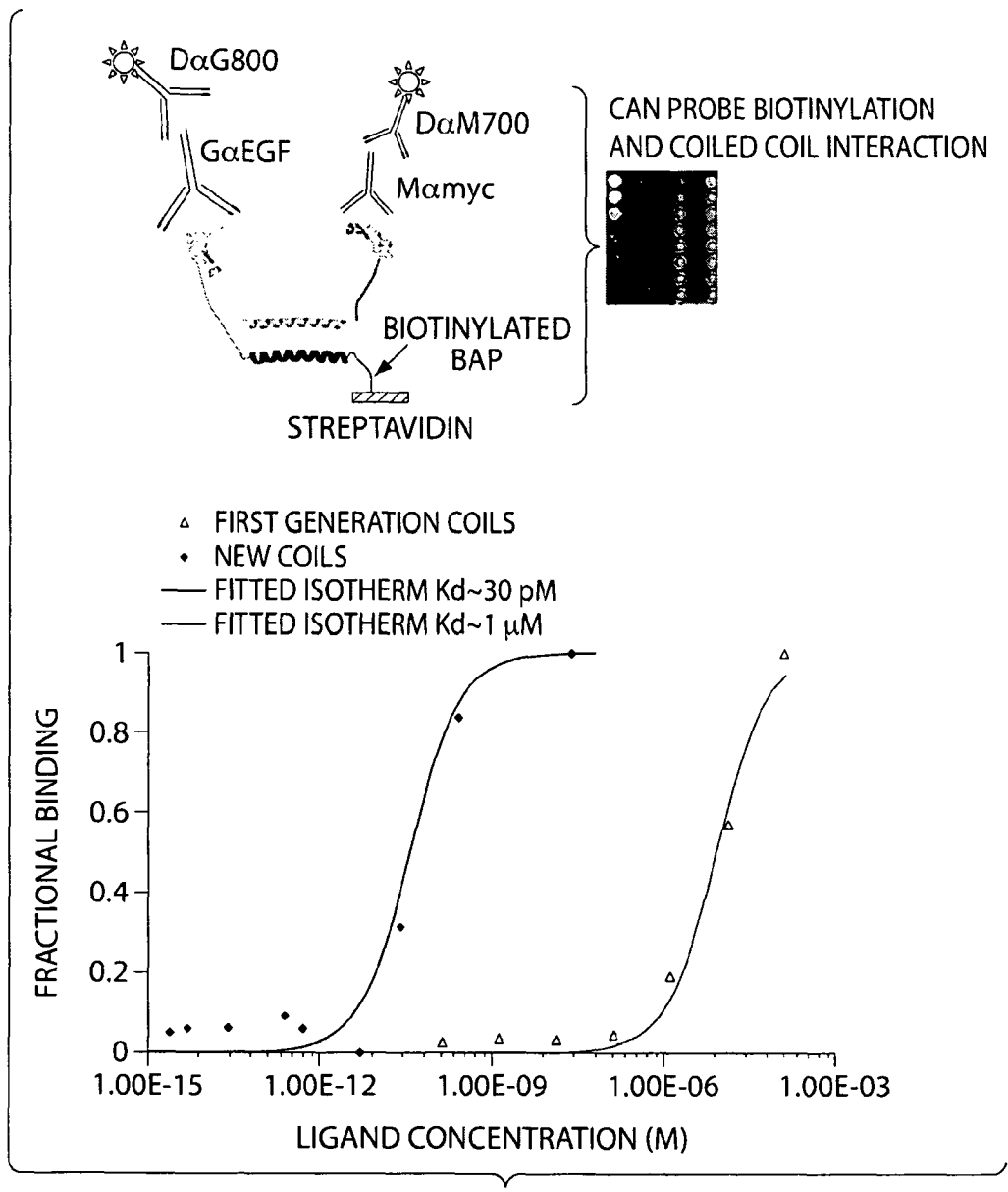
FIG. 15 shows results of a coiled coil interaction binding assay and binding isotherms for the first and second generation coiled coil domains. The first set of coils produced a weak binding pair (µM Kd), while the second set produced a pM binding pair.
Figure 16:
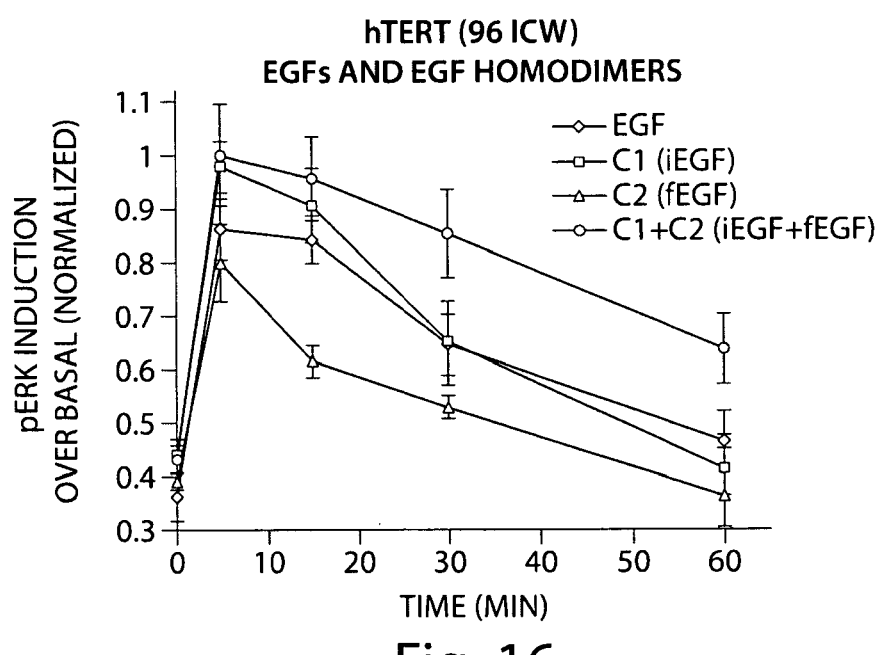
FIG. 16 shows the activation of ERK by EGF or by coiled coil ligands for EGFR in MSC cells over time.
Figure 17:
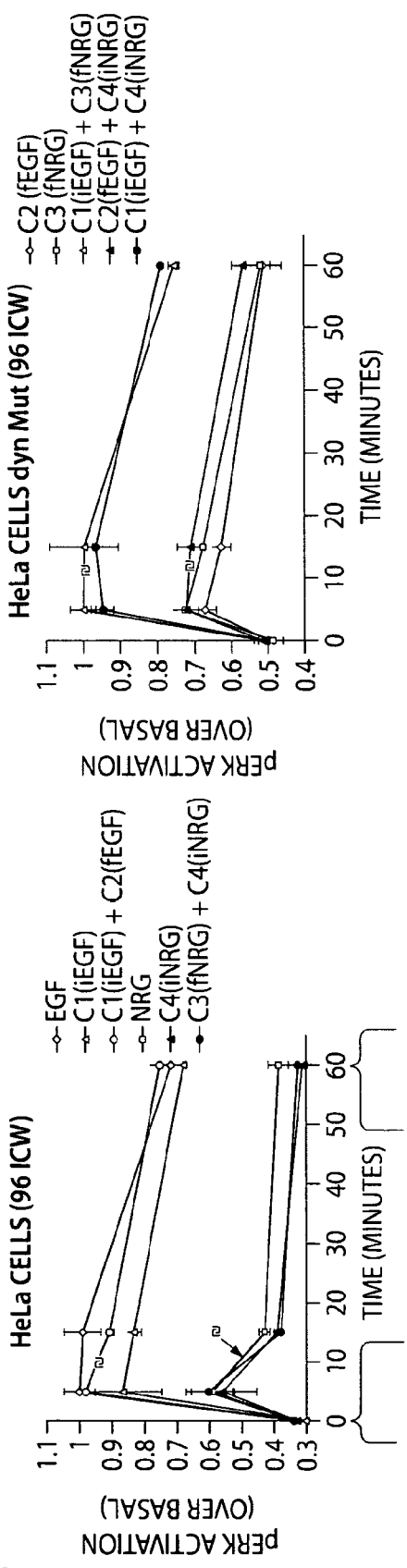
FIG. 17 provides a bioactivity characterization of ligands using a pERK activation in cell Western assay.
Figure 18:
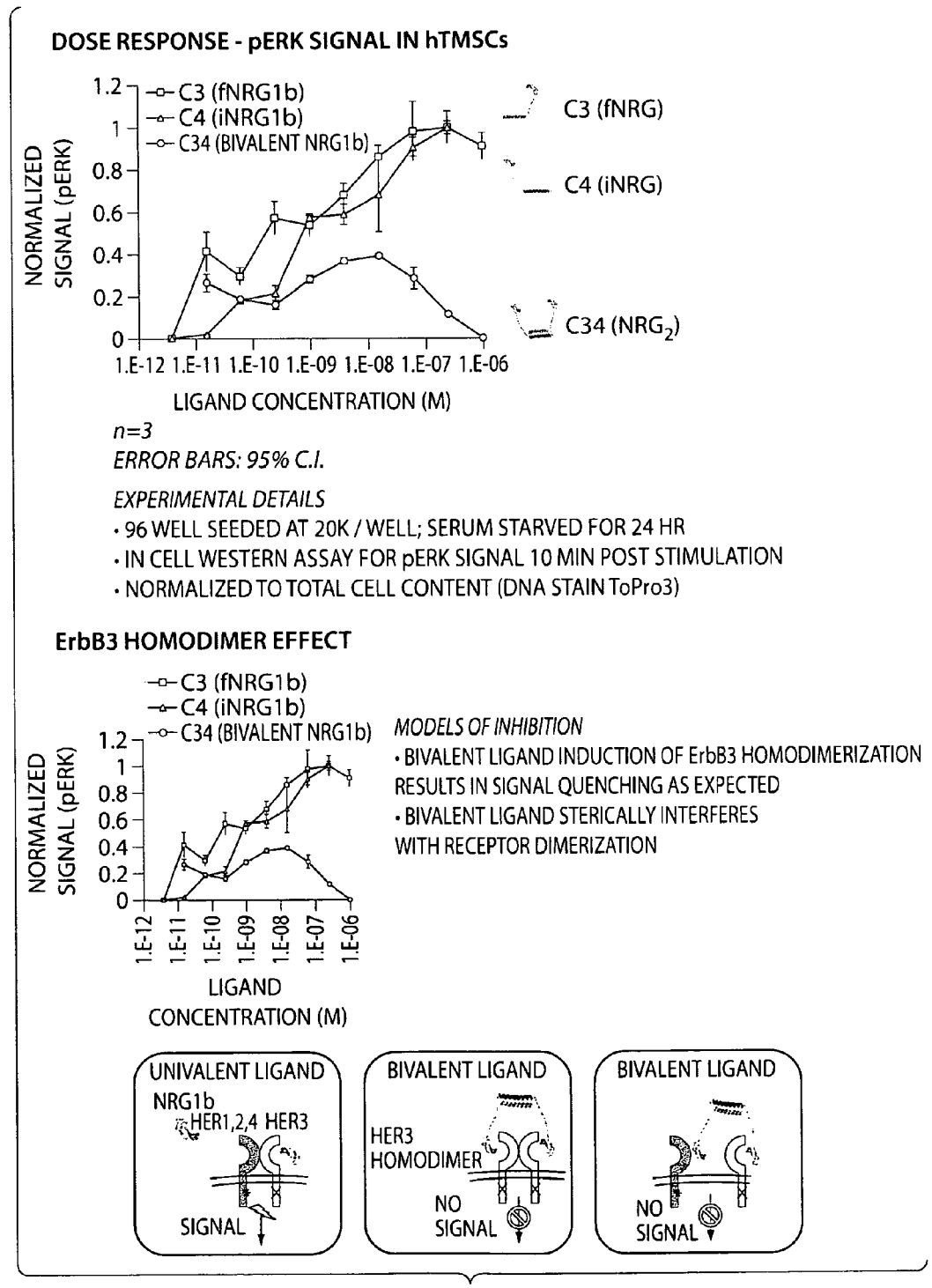
FIG. 18 evidences Her-3 homodimer formation leading to signal silencing brought on by NRG1-NRG1 bivalent ligands (i.e., ligand dimers). NRG1 monomers stimulate the ERK pathway in MSCs, but dimers inhibit signaling.
Figure 19:
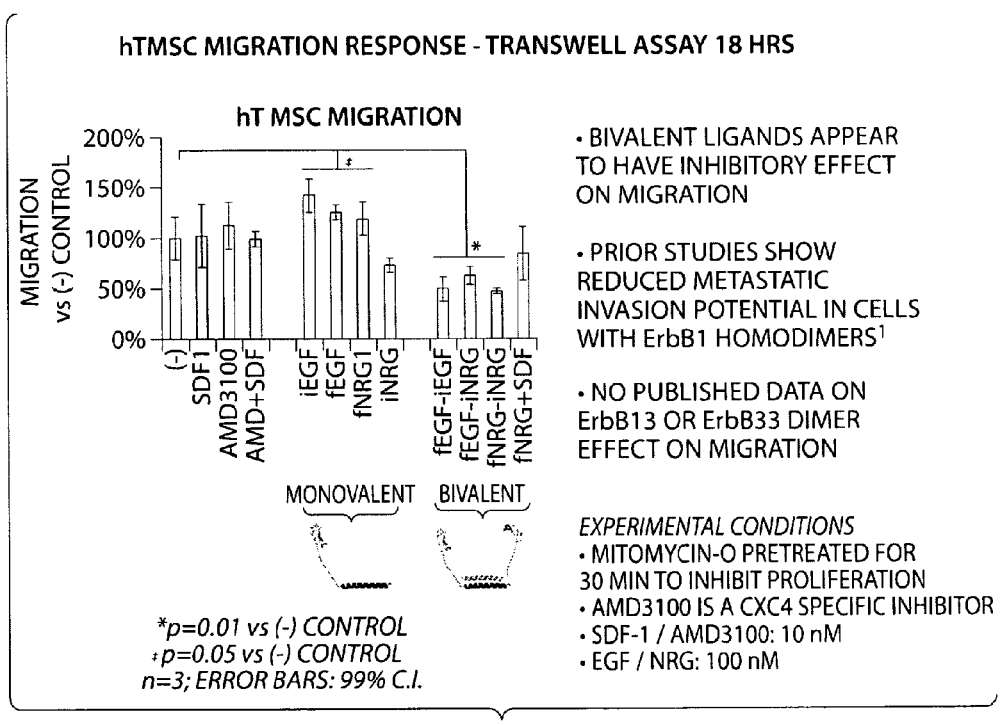
FIG. 19 illustrates differential migration of MSCs in a transwell assay treated with soluble monomeric and bivalent Her ligands. Stromal derived factor 1 (SDF1) and CXCR4 inhibitor AMD3100 are included for reference.
Figure 20:
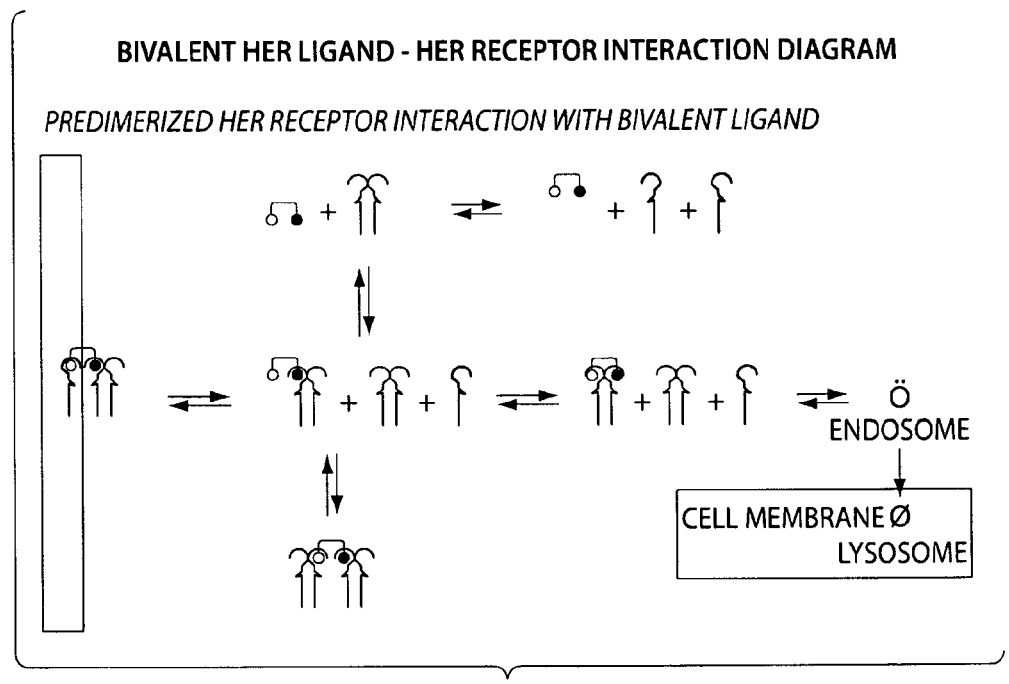
FIG. 20 provides a generic interaction diagram for bivalent Her ligands and Her receptors.
Figure 21:
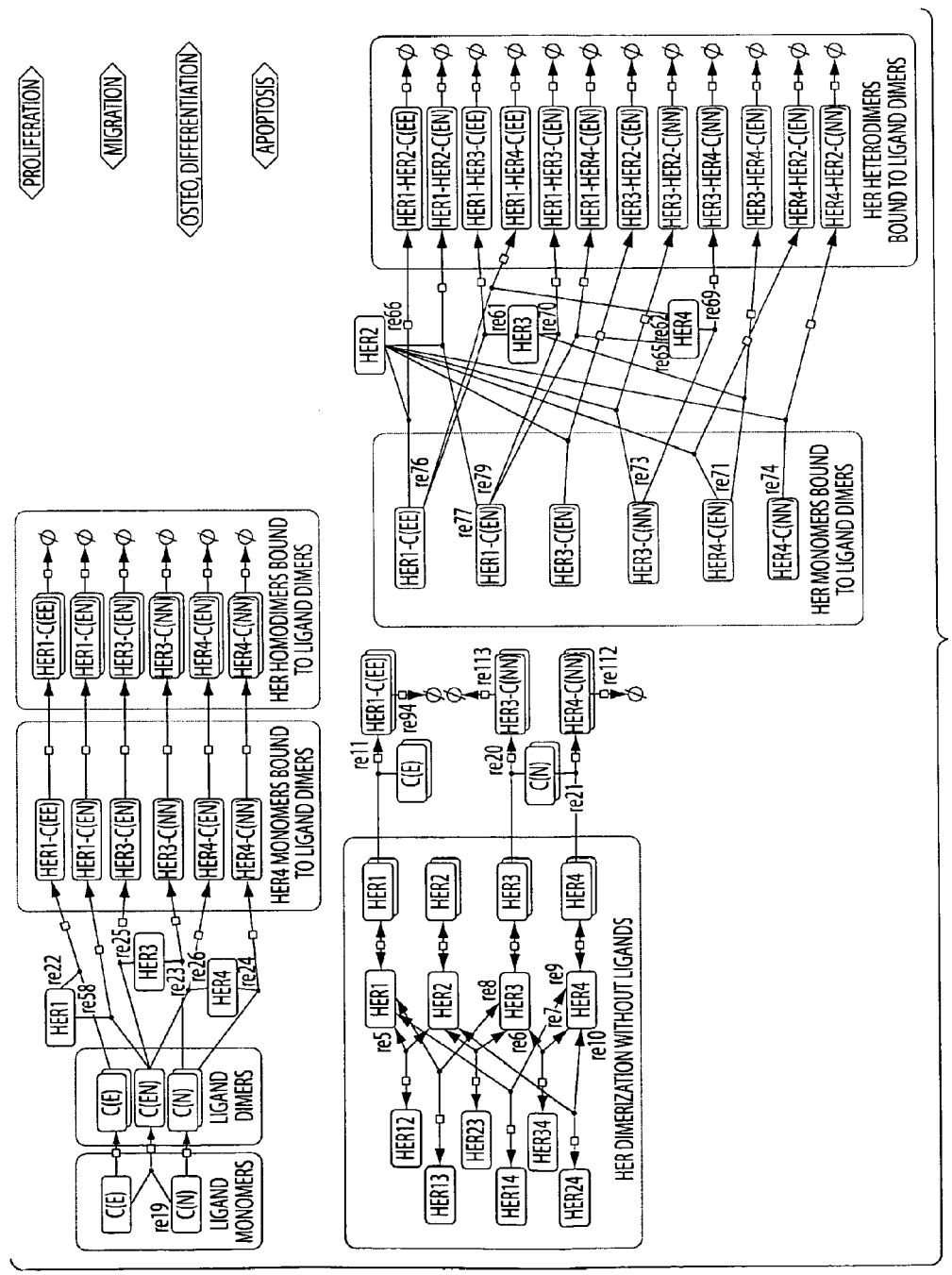
FIG. 21 provides a Cell Designer 4.0 diagram of the bivalent ligand Her receptor interaction network.
Figure 22:
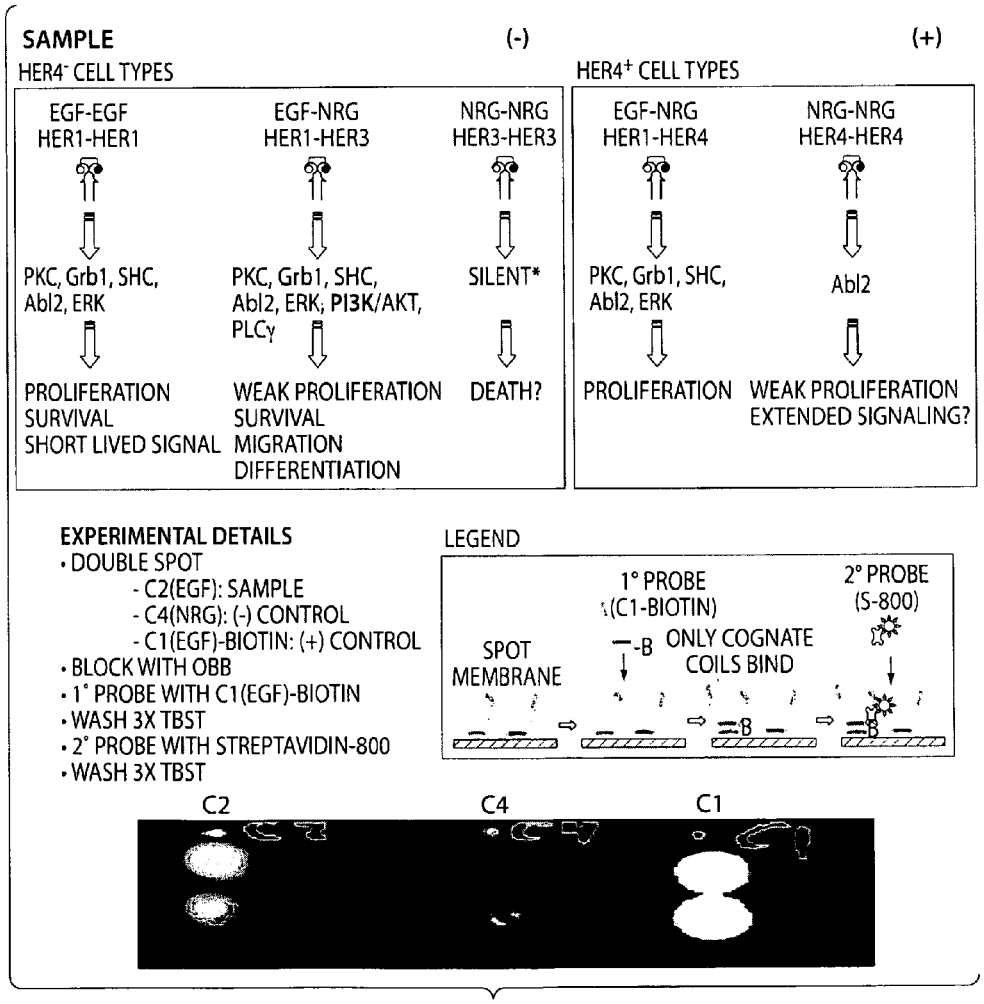
FIG. 22 illustrates a far Western spot blot performed to assess binding.
Figure 23:
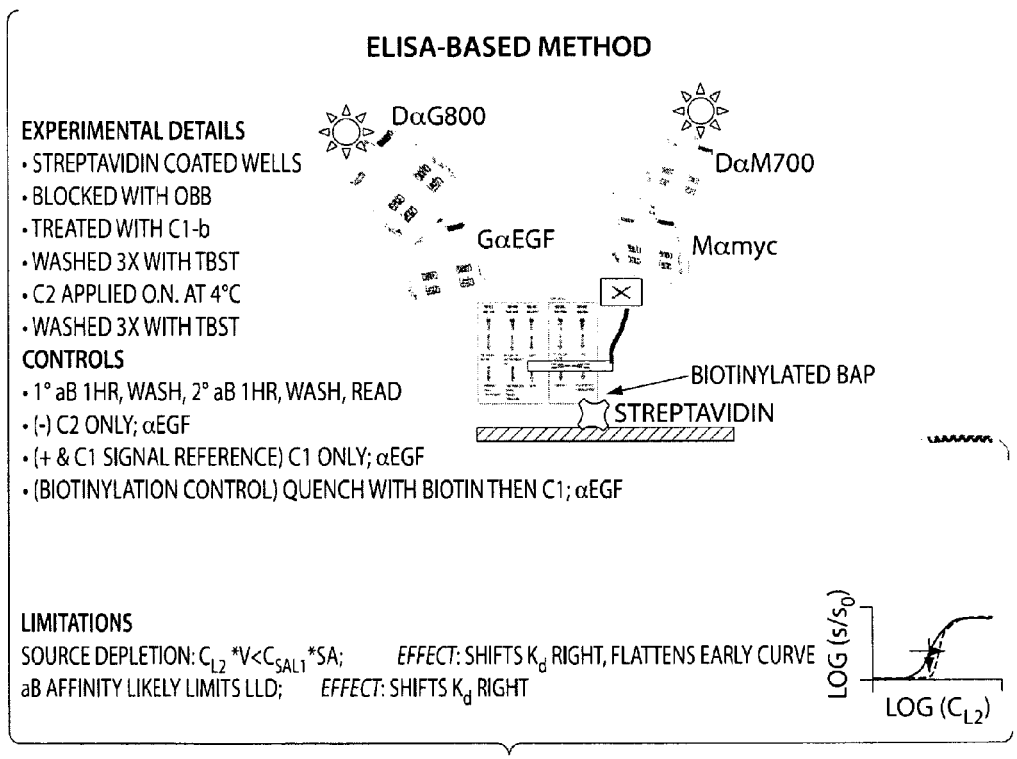
FIG. 23 illustrates an ELISA-based method to assess binding.
Figure 24:
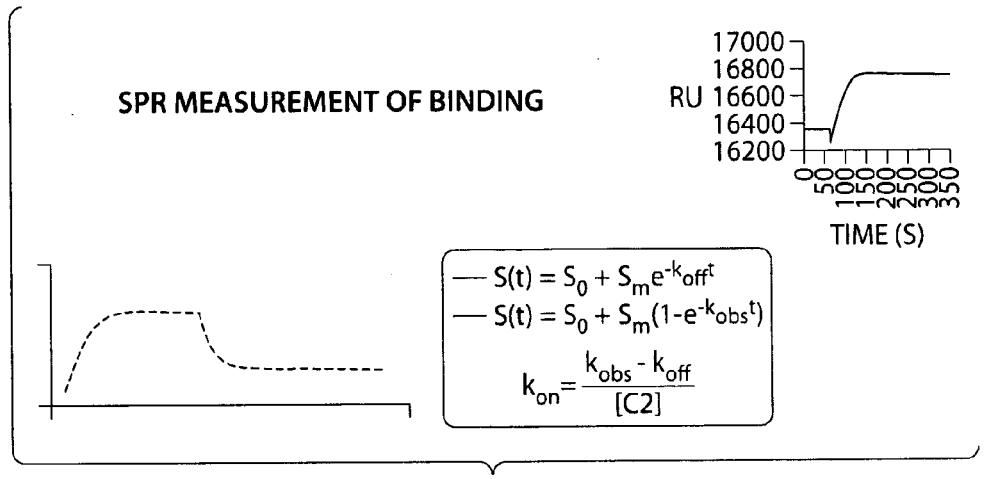
FIG. 24 illustrates a SPR measurement of binding.
Figure 25:
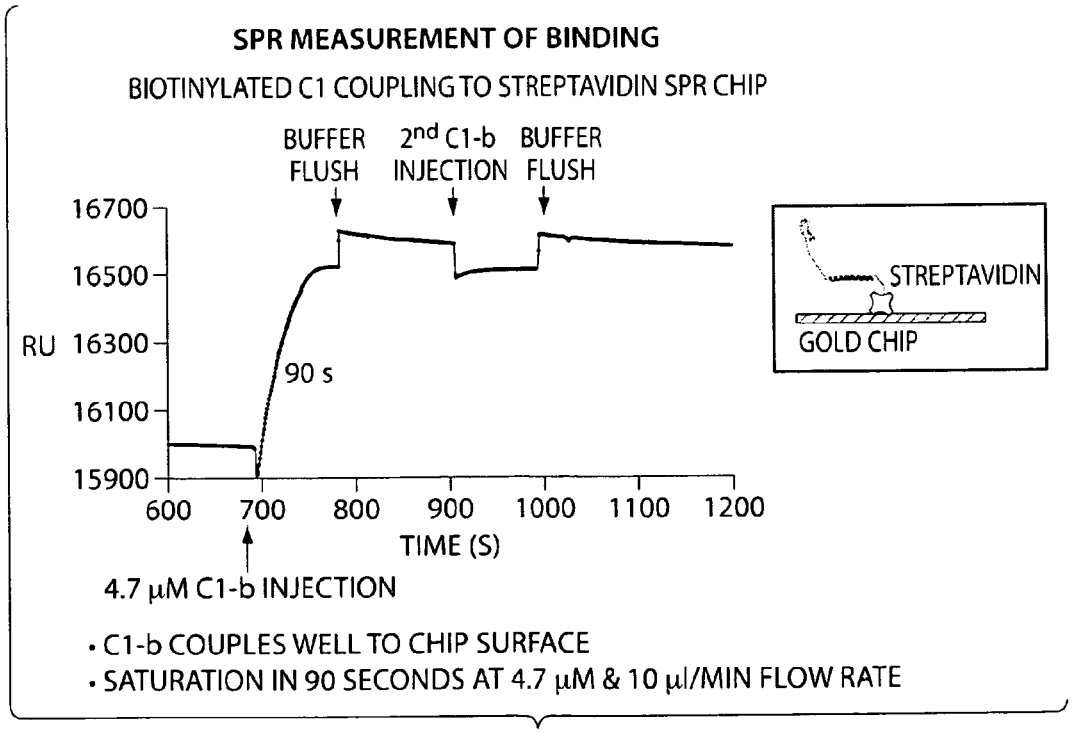
FIG. 25 shows results of a SPR measurement of binding (biotinylated C1 coupling to streptavidin SPR chip).
Figure 26:
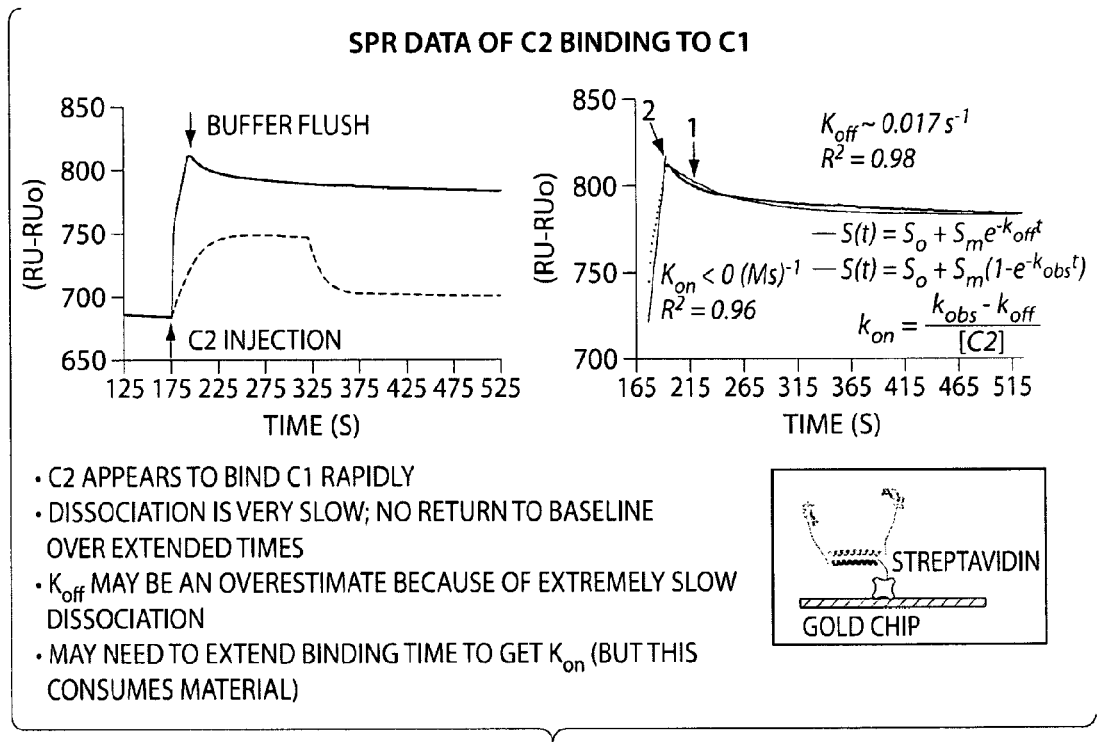
FIG. 26 shows results of a SPR measurement of binding of C2 to C1.
Figure 27:
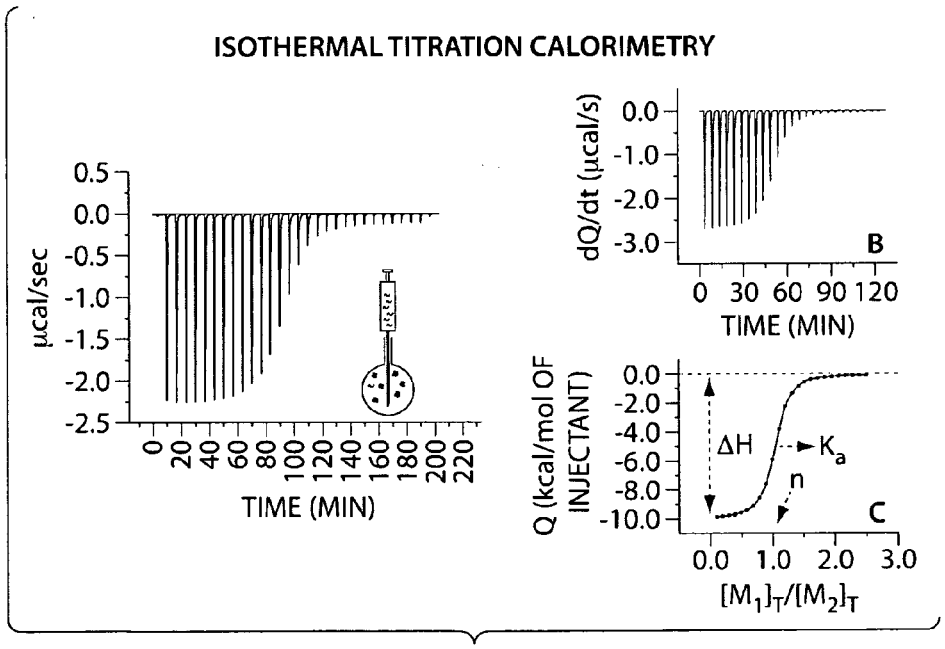
FIG. 27 illustrates isothermal titration calorimetry to assess binding.
Figure 28:
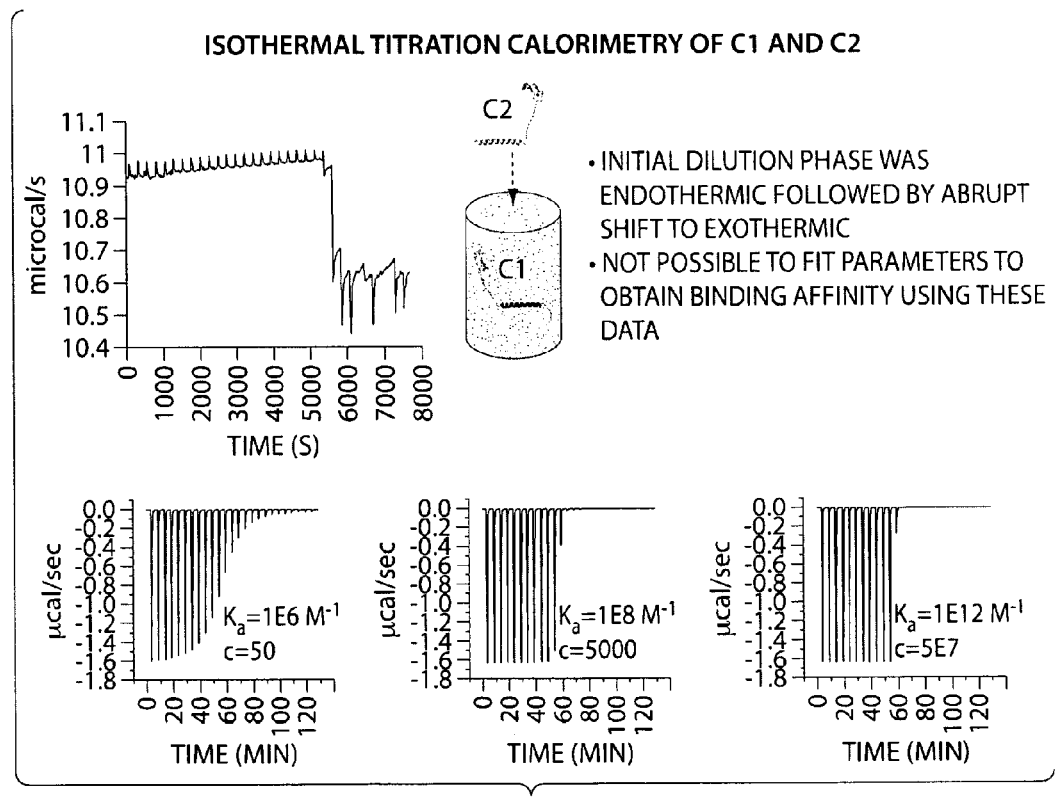
FIG. 28 shows results of isothermal titration calorimetry of C1 and C2.
Figure 29:
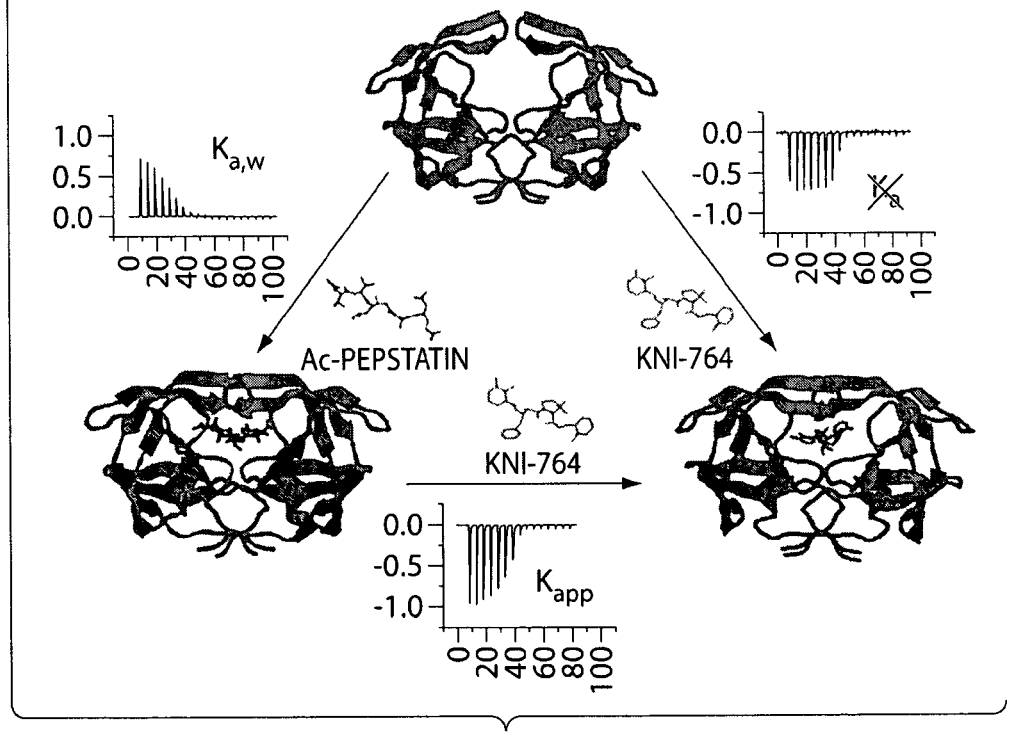
FIG. 29 provides an example procedure to characterize coiled coil binding.

A modular protein design can facilitate the investigation of homo- as well as heterodimers in both EGFR and Her-3 without requiring repetitive cloning, expression, and purification. The bivalent design with modularity can be realized by using a tight binding region that brings ligands together with the correct orientation and spacing to permit simultaneous receptor dimer binding. One implementation of this design is shown in FIG. 8. As illustrated, a coiled coil domain allows for cognate coil containing ligands to form a bivalent structure. The coil sequences were selected from previously published work and have been reported by several investigators to exhibit a $K_d$ as low as $10^{-15}$ M.[72-74]

The coils are separated from the ligand by a protease resistant spacer designed by Sauer et al. that confers flexibility, solubility, and together with the coils a sufficient extension to bridge a gap 20 nm long.[75] This is twice the distance between the most extreme termini in EGFs bound to dimeric EGFR. A schematic of the bivalent ligand is shown in FIG. 8, which also depicts additional functional moieties, including antibody detection epitopes, and a biotin acceptor peptide (BAP) sequence to permit biotinylation and subsequent immobilization on neutravidin coated matrices.

Examples of components of this system are shown in Table 3. A modular design allows the formation of bivalent EGF "EE", bivalent EGF-NRG "EN" (a mixed ligand), or bivalent NRG "NN". The monomeric ligands that serve as the components of this system are denoted C1 and C2 (the EGF containing ligands), and C3 and C4 (the NRG containing ligands). Based on the coiled heterospecificities the following bivalent ligands can be formed: C12 ("EE"), C13 ("EN), C24 ("EN"), C34 ("NN"). The panel exhibits a degeneracy of one in the mixed ligand combination "EN". The C13 combination was used for all studies of the EN bivalent ligand, unless otherwise noted.

TABLE 3

List of ligand components by type, bivalent binding partner, and presence of a biotin acceptor peptide sequence

| Name | Ligand Type | Can Pair | Biotin Acceptor |
|------|-------------|----------|-----------------|
| C1 | EGF | C2 or C3 | Yes |
| C2 | EGF | C1 or C4 | No |
| C3 | NRG | C1 or C4 | No |
| C4 | NRG | C3 or C2 | Yes |

Cloning and Protein Expression

Coding DNA for fusion proteins consisting of the human sequences of EGF or NRG-1β domains fused to protease resistant hydrophilic spacer arms fused to coiled coil domains followed by biotinylation sequences and epitope tags (as per Table 3) were designed in silico (using VECTORNTI) then ordered as a whole gene product with an E. coli codon bias from GeneArt (Regensburg, Germany). Coding sequences were amplified by PCR mutagenesis with flanking restriction sites to permit cloning into expression vectors.

Initially two T7 promoter based expression systems were used to produce the ligand components: a pET28(a) His-tagged system (Novagen, Madison, Wis.) for C1 and C4; and a maltose binding protein (MBP) tagged system: pMAL-c2X (New England Biolabs, Beverly, Mass.) for C2 and C3. The pET28a vector tended to produce inclusion bodies which require solubilization in 6 M urea+100 mM dithiothreitol followed by dialysis against a refolding buffer of reduced and oxidized glutathione.

Evaluation of both expression systems revealed that the pMAL system was superior in that it could produce large quantities of properly folded soluble protein and did not require the difficult isolation of inclusion bodies, denaturation, extensive refolding, and subsequent separation of misfolded isomers by reverse phase chromatography. This advantage represented a ten-fold improvement in performance over the pET expression system in terms of time and materials required. As a result, C1 and C4 were removed from the pET backbone and cloned into pMALc2x expression vectors (NEB) and used as such for all experiments.

All expression constructs were sequenced prior to transformation into the expression strain BL21(DE3)pLysS (Stratagene, Cedar Creek, Tex.). Transformed strains were grown to OD~0.6 with agitation at 37° C. Cultures were then brought to 25° C. and protein expression was induced with a single pulse of 100 nM IPTG for 4 hours. Protein was harvested following cell lysis with BUG BUSTER Master Mix reagent (Novagen) supplemented with PMSF and protease inhibitor cocktail (Sigma, St. Louis, Mo.).

Lysates were clarified by centrifugation at 3500 g for 1 hour at 4° C. Clear lysate was subjected to purification on amylose resin in accordance with the pMAL System protocol (New England Biolabs). Eluted protein was concentrated using an ultracentrifugation cassette (10 kDa MWCO, Pierce, Rockford, Ill.). Purification tags were cleaved by factor Xa digestion overnight at 30° C. in 20 mM tris, pH 7.4.

Validating Protein Identity

Figure 41:
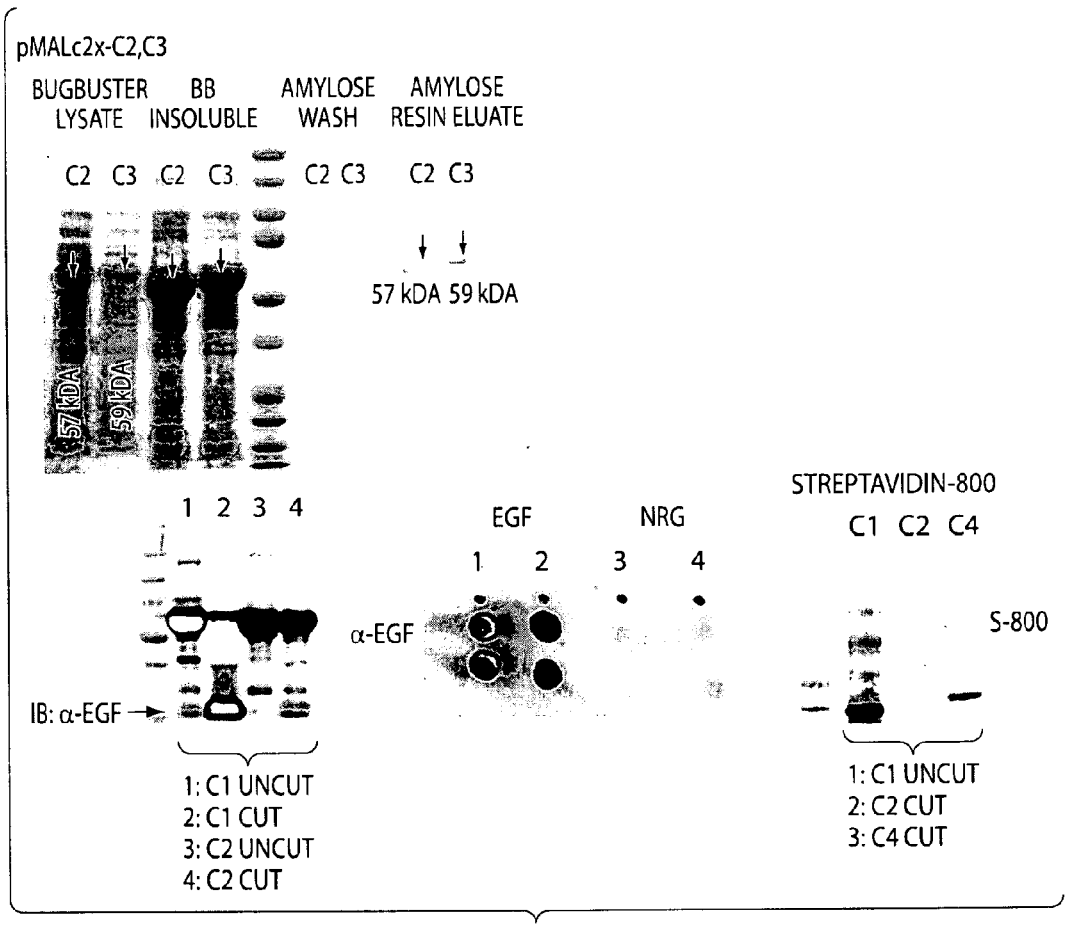
FIG. 41 shows characterization of expressed proteins. (Top) Coomassie stained SDS-PAGE gel of purified C2 and C3. The purity and estimated molecular weights of the purified proteins are evident from the rightmost two lanes. (Bottom) Immunoblots of ligands (cut indicates cleaved with factor Xa); spot blots confirm absence of EGF from NRG containing C3 and C4. Probing blots with streptavidin-800IRDYE confirms the presence of biotin on C1 and C4 (the BAP is a C-terminal sequence on each protein).

Purified proteins were analyzed by Coomassie staining of sodiumdodecylsulphate polyacrylamide gels (SDS-PAGE), immunoblot, mass spectrometry, absorbance at 280 nm (A280), and in vitro cell response versus wild type ligands EGF and NRG-1β (Peprotech, Rocky Hill, N.J.). A representative set of Coomassie and immunoblot analyses is shown in FIG. 41. Coomassie staining gives estimated molecular weight and relative purity. Typical purities ranged from 80-95%. Immunoblots confirmed the presence of full length protein when probed for terminal epitopes.

Confirming Ligand Bioactivity

Figure 42:
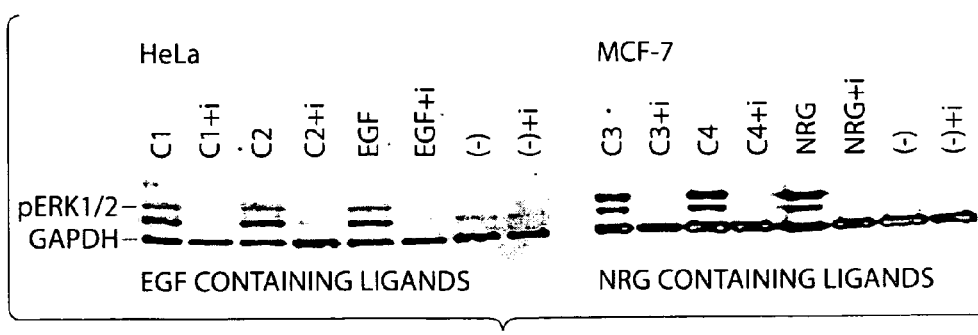
FIG. 42 shows a ligand bioactivity assay. EGF containing ligands (C1 and C2) were used to stimulate HeLa cells and compared with wtEGF stimulation. NRG containing ligands were likewise evaluated in MCF-7 cells.

Bioactivity of purified fractions was confirmed by in vitro cell response versus wild type ligands EGF and NRG-1β (Peprotech). Specificity for Her receptor activation was further assessed by including inhibitor controls using the pan-Her kinase inhibitor N-(4-((3-Chloro-4-fluorophenyl)amino) pyrido[3,4-d]pyrimidin-6-yl)-2-butynamide (Calbiochem #324840, San Diego, Calif.). Bioactivity and Her specificity were validated in HeLa and MCF-7 cells (for EGF and NRG containing ligands, respectively). HeLa cells express EGFR and Her-2 and are responsive to EGF while MCF-7 cells express Her-3 and Her-4 and are responsive to NRG. FIG. 42 is an immunoblot of pERK1/2 stimulation following ligand dosing.

The singly-dosed ligands produce pERK activation which is indistinguishable from their native analogues, and which is capable of being specifically inhibited by a pan-Her kinase inhibitor. This assay illustrates the effectiveness of the purification methods and validates the use of these ligands for use in bivalent experiments.

Biotinylation of Ligands

Incorporation of a tethering motif into the ligand design allows for greater flexibility in surface immobilization on tissue engineering scaffolds and for purposes of detection. The biotin-streptavidin interaction is one of the tightest non-covalent interactions known ($k_D$~$10^{-15}$ M) and is essentially irreversible over a broad range of conditions. The incorporation of a biotin acceptor peptide (BAP) sequence as a terminal fusion to C1 and C4 permits the biotinylation of these ligands and subsequent immobilization via interaction with immobilized streptavidin. The BAP is a 15 amino acid sequence that acts as a substrate for biotin ligase (BirA).

During expression in *E. coli* some fraction of the ligand is biotinylated by endogenous BirA. To achieve a higher level of biotinylation (>80%) exogenous BirA can be used following ligand purification. The degree of biotinylation can be measured by the degree of change in absorbance of 4'-hydroxyazobenzene-2-carboxylic acid (HABA) at 500 nm. Assays based on this sensor report the percentage of ligand that is biotinylated. In addition to quantitative assays the biotinylation of ligand can be detected by spotting on a nitrocellulose membrane and probing with IR-fluorescently labeled streptavidin and by SPR analysis with a streptavidin-coated gold chip. Biotinylated ligands can be used in a variety of experimental schemes which incorporate a streptavidin (neutravidin or captavidin) tethering surface.

Characterizing the Coiled Coil Interaction

Figure 43:
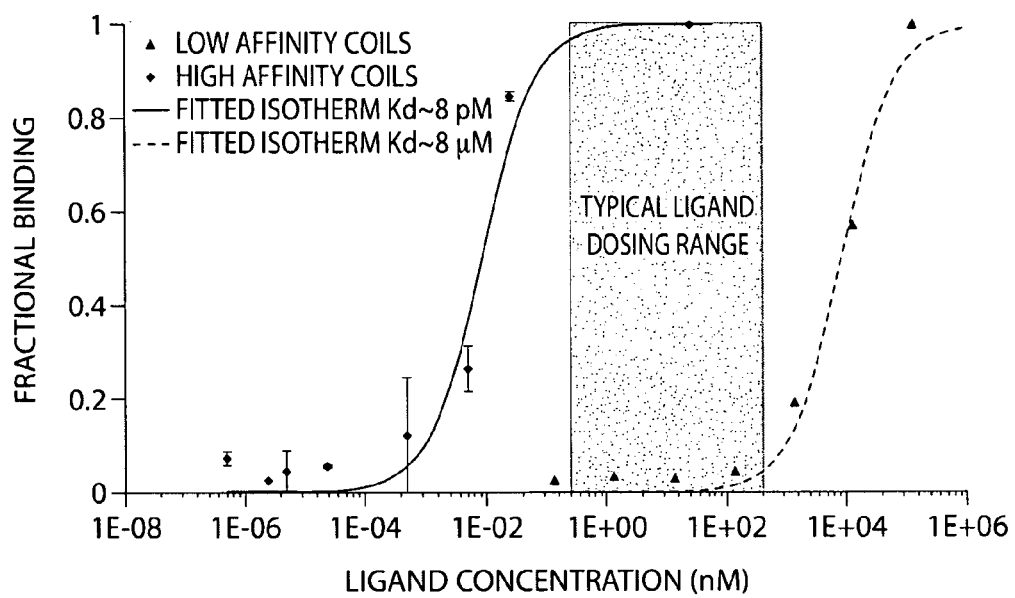
FIG. 43 shows an immunofluorescent binding assay. An ELISA-based method using streptavidin coated EIA plates was used to achieve very sensitive detection of bound ligand. n=3, +/−s.d.

The first generation of coils produced an interaction which exhibited micro-molar affinity as shown in FIG. 43.[92, 93] This set of coils was replaced with a modified set of coils by site directed mutagenesis of the original construct.

When assayed by an enhanced immuno-fluorescence binding method the new coils yielded a Kd of ~30 pM. This is approximately two orders of magnitude below the lowest relevant dose of EGF or NRG used in vitro and would ensure complete binding of the bivalent components.

Immunofluorescent Binding Assay

Characterization of the coiled coil interaction shown in FIG. 8 was performed by an immuno-fluorescent binding assay on streptavidin-coated wells. Biotinylated C1 was incubated on the well surface and a titration of cognate coil concentrations was used to generate a binding curve. Controls included non-biotinylated ligand to measure non-specific adsorption and staining of biotinylated ligand with 2° antibody to control for variations in bound ligand. Fitting these data to a one-parameter binding isotherm gives a $K_d$ of 30 pM.

Far Western Blotting

Figure 44:
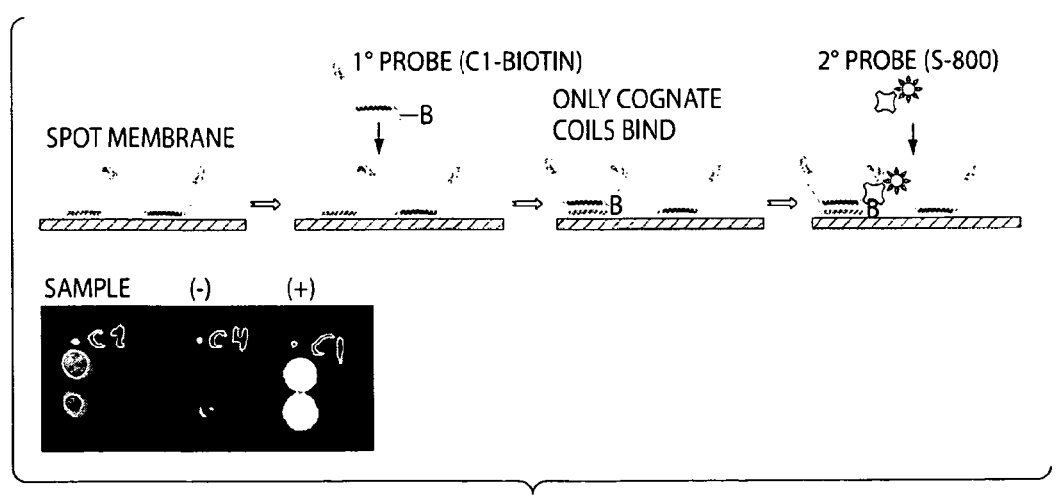
FIG. 44 shows a far Western analysis of coiled coil interaction. C2, C4 and C1 (control) protein were spotted in duplicate onto a nitrocellulose membrane (labeled C2, C4, and C1, bottom). The membrane is then probed with soluble C1 to allow binding between C1 and C2. Evidence of binding is seen in the positive signal seen over the two C2 spots. The negative control C4 should not bind C1 and is shown to produce only background signal. C1 is spotted directly (positive control, rightmost spots). Membrane was probed with streptavidin-800 IR dye to detect biotinylated C1.

Coiled coil binding was also investigated using far Western blotting. This was carried out by spotting 0.5 μl of sample ligand binding partner and controls in duplicate at 1 μM concentration onto a nitrocellulose membrane that was pre-wetted with 1 X transfer buffer (4:1 MQ water:methanol and MES buffer). Membranes were washed three times with 20 mM tris-buffered saline+Tween-20 (TBST), pH 7.4 (TBST) then blocked for 1 hour with Licor Odyssey blocking buffer (OBB) then biotinylated cognate binding proteins were added to the blocking buffer at 100 nM and incubated overnight at 4° C. The membranes were then washed three times with TBST and probed for 1 hour with IR dye conjugated streptavidin (Rockland, Gilbertsville, Pa.) diluted 1:10,000 in OBB. The membranes were then washed three times in TBST and scanned on a LI-COR ODYSSEY IR scanner. FIG. 44 illustrates the experimental concept and the resulting data. Binding due to the coiled coil interaction is evident from the significant signal in the cognate binding pair C1+C2.

Surface Plasmon Resonance

Surface plasmon resonance was performed on a BIA-CORE2000 instrument using a streptavidin-coated gold analysis chip. Biotinylated C1 was immobilized on the chip surface and brought to equilibrium with running buffer. The conjugation of C1 to the chip surface exhibited a stable baseline within 90 seconds of flowing C1 and remained stable over long buffer wash times, indicating a stable surface binding of C1. Attempts to conjugate additional C1 showed no change in the baseline, indicating saturation of the chip surface.

Figure 45:
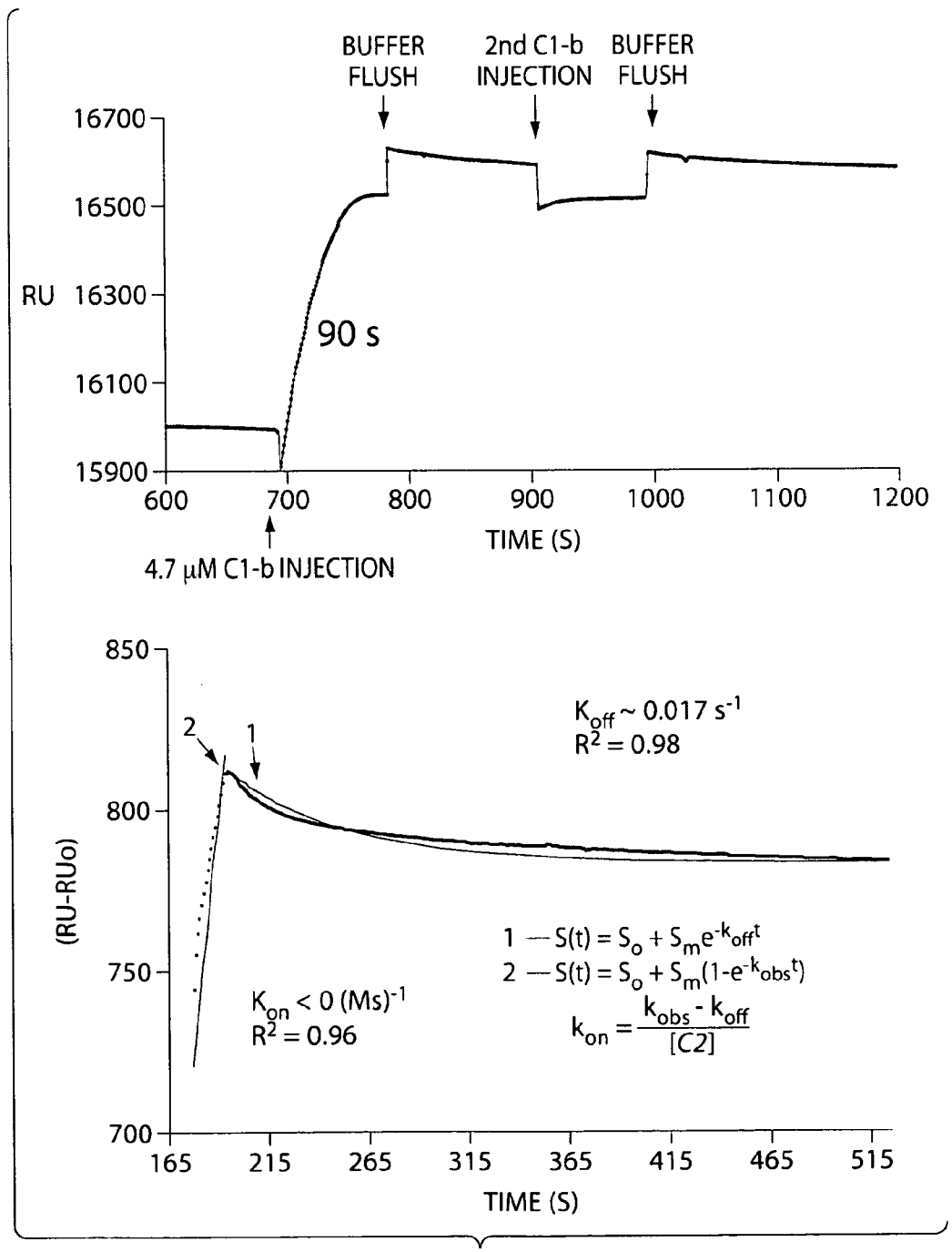
FIG. 45 shows a Surface Plasmon Resonance analysis of coiled coil interaction.

Cognate binding partner C2 was then flowed over the surface and binding signal collected. FIG. 45 shows data from the biotin-streptavidin chip conjugation and the C2 binding analysis. Data analysis is performed on the separate binding and unbinding portions of the response curve. During binding the partner in the mobile phase (C2) undergoes both binding and unbinding and so the data produced contain a combination of both effects. This is captured in the lumped variable called $k_{obs}$ as shown in equation 2.1. The unbinding portion of the data reflects purely unbinding since the mobile phase does not contain appreciable amounts of C2 during this step. The pure unbinding is captured by $k_{off}$ as shown in equation 2.2. In order to obtain the on rate during the binding step, the $k_{obs}$ is transformed by subtracting $k_{off}$ and normalizing by the ligand concentration in the mobile phase during the binding step. In this way both $k_{off}$ and $k_{on}$ are obtained, allowing the dissociation constant to be calculated as shown in equation 2.4.

$$S(t) = S_o + S_m(1 - e^{-k_{obs}t}) \qquad (2.1)$$

$$S(t) = S_o + S_m e^{-k_{off}t} \qquad (2.2)$$

$$k_{on} = \frac{k_{obs} - k_{off}}{[C2]} \qquad (2.3)$$

$$K_d = \frac{k_{off}}{k_{on}} \qquad (2.4)$$

The data produced by SPR are generally acceptable for binding affinities weaker than low nanomolar. Very tight binding interactions that are high picomolar and below generally produce data which cannot be fit reliably with the approach outlined above. This happens to be the case for the binding interaction between C1 and C2. As seen in FIG. 45 the $k_{on}$ fitting gives a non-physical value. This can be interpreted as an effect of the extremely tight binding of this coil pair. The binding affinity obtained from the immunofluorescent binding assay (30 pM) confirms this effect.

Isothermal Titration Calorimetry

Isothermal titration calorimetry can be used to study interactions between proteins with dissociation constants that are between 100 nM-100 µM. The ability of this method to detect very tight interactions is limited by the ability to track changes in differential heat transfer that occur over a small range of titration volumes. Although the data could not be fit to obtain a binding constant they are supportive of previous results of an extremely tight binding interaction.

Example 3

Influence of Soluble Bivalent Ligands on Cell Signaling and Phenotype

Introduction

Evidence supports the concept that EGFR family members must homo- or hetero-dimerize in order to initiate intracellular signaling events, and that ligand binding to at least one dimer member is required under most normal physiological circumstances.[2, 58] However, the sequence of events leading to an active ligand-occupied receptor dimer pair is not fully understood and may ultimately depend on the cellular context. In the canonical model, applicable to the ligand-binding receptors EGFR, Her-3 and Her-4 receptors exist on the surface in a closed configuration stabilized by interactions between extracellular subdomains II and IV.[94] When ligand binds, the receptor opens and adopts a new stable configuration, exposing a "dimerization arm" on the extracellular domain, leading to creation of dimers stabilized by both extracellular and intracellular domains of the receptor.[95-97] An alternate model holds that receptors exist in pre-formed dimers or higher-level aggregates,[98-101] but that activation requires conformational changes induced by ligand binding.[70, 95] Her-2 does not precisely fit either model, as it has no known ligands and is constitutively present in a conformation with the dimerization loop exposed to allow heterodimerization with EGFR, Her-3 and Her-4, even in the absence of ligand.[2, 58, 63] Notably, cells that overexpress Her-2—i.e., that express Her-2 at levels associated with some pathology—have constitutively active Her-2 due to homodimerization.[102] Bivalent ligands can serve to drive particular dimerization events between lone receptors; to stabilize pre-existing dimers; or to disrupt pre-existing unoccupied receptor interactions (such as Her-3 clusters) and drive new ones.

For all members of the EGFR family, signal attenuation is achieved by at least two known mechanisms: tyrosine phosphatase deactivation; and receptor internalization and intracellular trafficking to lysomal degradation.[61, 103] Upon ligand binding, EGFR is internalized within minutes and later degraded in lyzosomes.[104] The internalization depends on the dimerization status, as Her-2 heterodimerization with EGFR decreases the internalization rate constant for EGFR and increases the fraction of EGFR recycled to the cell surface following internalization.[105] Dimer composition can also affect the relative rate of dephosphorylation by altering the trafficking and localization of a liganded receptor dimer as well as by differentially recruiting phosphatases to adaptor sites.

Much of the understanding of the Her receptor signaling pathway comes from studies with either natural or deliberate genetic mutations of ligands and receptors in cell lines, and use of inhibitors of binding and signaling. The development of the bivalent ligand system described in Example 2 allows a new approach to manipulate the Her system by using a purely exogenous method, in the form of bivalent ligands, to form selective Her dimers as shown, for example, in FIG. 46.

Biasing EGFR Family Receptor Dimerization

Figure 46:
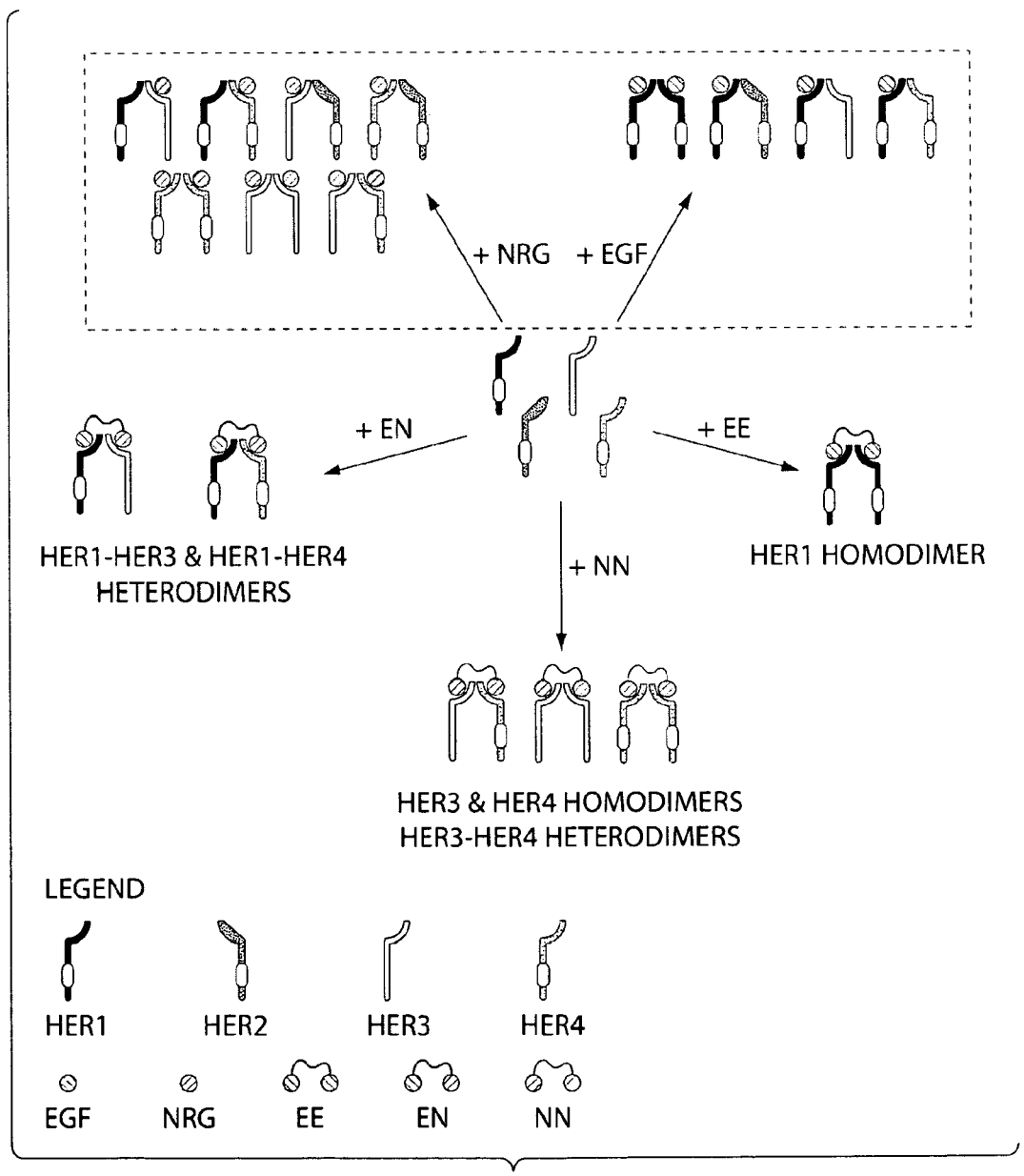
FIG. 46 shows examples of Her receptor dimerization outcomes. Stimulation of cells expressing different Her receptors with wild type monovalent ligands gives rise to heterogeneous distributions of Her dimers (dotted box). Bivalent ligand stimulation is predicted to bias receptor dimerization as shown in the lower panel.

FIG. 46 depicts possible outcomes of Her receptor dimerization when a cell expressing all four types of Her receptors is stimulated with either wild type (monovalent) ligands (EGF or NRG) or with dimer ligands (EE, EN or NN). For example, the EGF-EGF ligand dimer is expected to drive EGFR homodimerization and thereby inhibit EGFR-Her-2 heterodimerization. Although few cells express appreciable amounts of all four receptors, the figure illustrates that stimulation with dimer ligands can bias the degree of homo- or hetero-dimerization, with the practical outcome of either fostering formation of desirable dimerizations, or excluding potentially deleterious dimerizations (e.g., sequestering Her-3 in inactive pairs; preventing EGFR-Her-2 dimers). In addition to the dimeric outcomes illustrated in FIG. 46, a bivalent ligand could also lead to formation of oligomers, by serving as a bridge between two different adjacent receptor dimers.

The quantitative outcome of stimulation by either monovalent or bivalent ligand is expected to depend on both the absolute number of each EGFR family member expressed as well as the relative numbers. For example, in cells that express high levels of any single receptor (>200,000 per cell), pre-formed receptor dimers could compete more with the effects of ligand dimers. Thus, a particular dimer ligand can exert a different phenotypic and signaling response in epithelial cells expressing high levels of multiple EGFR receptor family members as compared to mesenchymal stem cells, which express EGFR, Her-2 and Her-3 at levels below 10,000 receptors/cell, and do not express Her-4. These differences, however, can be evaluated by those of skill in the art with the methods provided herein.

Despite how the context of an individual cell may influence outcomes, it is possible to make predictions about how particular types of receptor biasing is expected to influence downstream signaling based on what is known about the signaling pathways initiated by each Her receptor dimer. For example, activation of the Her-1 homodimer is expected to produce increases in pERK leading to proliferative signaling that are weaker than those produced by Her-1-Her-2 heterodimers.[22] EGFR homodimers are trafficked via endocytosis at a higher rate than its heterodimers[17] and so preferential recruitment of EGFR homodimers might result in increased receptor internalization and degradation.[22]

Bivalent dimers of EGF-NRG would bring together Her-1-Her-3 or Her-1-Her-4 heterodimers and would likely give rise to canonical Her-1 signaling through STAT3 as well as Her-3 mediated PI3K signaling.[90] The phenotypic outcomes resulting from this type of stimulation will likely depend on the relative expression levels of the various Her receptors with respect to each other.

The EGF-NRG bivalent ligand is expected to reduce the mitogenic signaling that arises from the free association between Her-2 and Her-3 that normally occurs in cells expressing high amounts of these receptors.[106] The Her-2-3 heterodimer is the most potent mitogenic pair in certain tumor cell types,[49] hence inhibiting heterodimerization with N—N bivalent ligands is expected to have therapeutic potential.

Stimulation of cells expressing Her-3 along with EGFR or Her-2 and lacking Her-4 using the N—N homodimer is expected to silence Her-3-mediated signaling because Her-3 receptors are kinase deficient and must heterodimerize to signal. As NRG also binds with high affinity to Her-4, stimulation of cells expressing both Her-3 and Her-4 (a relatively uncommon situation) will have a complex response that can be parsed using inhibitors that block binding to Her-4.

Rationale for Choice of Cell Lines Used in Signaling and Phenotypic Studies

In one non-limiting example, EGFR family signaling is manipulated to influence regenerative responses of mesenchymal stem cells (MSC). Signaling by members of the EGFR family has been implicated in numerous facets of bone development, homeostasis, and regeneration.[107] Human MSC, even very early after isolation from marrow, express EGFR, Her-2, and Her-3 but no detectable levels of Her-4.[57] The expression levels of EGFR family members in both an hTERT-immortalized human MSC line and in primary bone marrow-derived MSC are relatively low and regulated by culture conditions: EGFR is expressed at 5,000-10,000 copies per cell, Her-2 at about half the level of EGFR, and Her-3 at low but detectable levels.[57, 90] It is expected that all monovalent and bivalent NRG stimulation acts through Her-3, as MSC do not express detectable levels of Her-4. In MSC, it is expected that all three bivalent ligands—EE, EN, and NN—will exert different effects than their monovalent counterparts through biasing EGFR homodimers at the expense of EGFR-Her-2 heterodimers (EE), inhibiting Her-3 signaling by preventing heterodimerization with Her-2 or EGFR(NN), and driving EGFR-Her-3 heterodimers at the expense of the more highly favored Her-3-Her-2 heterodimers (EN). Phenotypic responses of MSC to EGFR family ligands include colony formation, survival, growth, migration and differentiation.

Although the MSC system is attractive for regeneration medicine, it has limitations for exploring the effects of bivalent EGFR family ligands on cell signaling and phenotypic responses. Many phenotypic responses have been studied; however, relatively few investigations have focused on EGFR family-mediated signaling in MSCs. Because these cells have relatively few receptors, some signaling responses may be at the limit of detection with available reagents, even though phenotypic responses are robust. The relative paucity of receptors is also representative of only one end of the spectrum of parameter space of interest—cells with one or more EGFR family members highly expressed may represent a different regime of balance between binding and signaling phenomena by virtue of having a different dynamic equilibrium among dimer states.

Therefore, in addition to analyzing responses in human MSC, responses in two epithelial tumor lines that express select EGFR family members at relatively high levels and have well-characterized EGFR family-mediated behaviors were investigated. HeLa cells, a cervical cancer-derived line that is often used as a model of EGFR-mediated signaling, have relatively high EGFR and Her-2 expression (~50,000 surface receptors for both EGFR and Her-2) with robust response to EGF treatment and low Her-3 and Her-4 expression with weak response to NRG treatment.[91] Because HeLa cells express roughly comparable levels of EGFR and Her-2, and EGFR-Her-2 heterodimers signal more robustly for growth than do EGFR-EGFR homodimers, HeLa cells would likely respond to EE ligand dimers by exhibiting both a Her-2 phosphorylation level and a level of proliferation that is between monomeric EGF-stimulated and completely unstimulated HeLa cells. Thus HeLa cells are well suited to characterize bivalent ligands which contain EGF.

As a model cell system for analyzing cell responses to bivalent ligands containing NRG, without confounding effects of high EGFR expression, the mammary tumor line MCF-7 was used, which express Her-3 at relatively high levels, and EGFR at relatively low levels (<5000 EGFR/cell). MCF-7 cells also express low levels of Her-2 and Her-4, exhibit a robust response to NRG stimulation, and have well characterized Her-3 signaling pathways. Because MCF-7 express Her-4, and antibodies that block NRG binding to Her-4 are available, these cells represent an useful model to screen primary phenomena occurring during stimulation with NRG-containing bivalent ligands. It is expected that MCF-7 and other Her-3-dependent cancer cell lines will respond to N—N ligand dimers by forming Her-3 homodimers thus becoming quiescent or apoptotic due to the kinase deficiency of Her-3 and sequestration of Her-3 receptors into silent complexes; this effect would likely be mitigated in cells (such as MCF-7) that also express Her-4.

Materials and Methods

Cell Culture

Human telomerase reverse transcriptase (hTERT)-immortalized human Mesenchymal Stem Cells (hTMSC) were a gift from Dr. Junya Toguchida (Kyoto University, Kyoto, Japan). HeLa cells were obtained from (ATCC, Manassas, Va.). HeLa and htMSCs were maintained in Dulbecco's modified Eagle's medium (DMEM) containing: 10% fetal bovine serum (FBS), 1% L-glutamine, and 1% penicillin/streptomycin at 37° C., 95% humidity, and 5% $CO_2$. MCF7 cells were maintained in phenol red free medium of the same composition and under the same incubation conditions. For single-cell migration studies, hTMSCs were maintained in a DMEM medium containing: 0.5% dialyzed fetal bovine serum (FBS), 1% L-glutamine, and 1% penicillin/streptomycin at 37° C., 95% humidity, and 5% $CO_2$.

Cells were washed with PBS at 37° C. and trypsinized. Once the cells had detached, trypsin action was blocked by adding growth medium. Cell solution was then centrifuged for 3 minutes at 500 rpm at 4° C. The solution was then aspirated and the pellet was resuspended in quiescent medium—Dulbecco's modified Eagle's medium (DMEM), 0.5% dialyzed FBS (dFBS), 1 mM pyruvate, 1 mM L-glutamine, 1 μM nonessential amino acids, and 100 units/ml penicillin-streptomycin (Invitrogen, Carlsbad, Calif.)—to obtain a concentration of 300,000 cells per ml. In a twelve-well plate, 1 ml of cell solution was added per well (area is 3.8 $cm^2$). After 16-20 hours, medium was aspirated and replaced with stimulation medium (quiescent medium containing ligand at known concentration). The ligand solutions were prepared just before stimulation and maintained at 37° C. After stimulation the lysates were collected according to phosphoprotein assay protocols (described below).

Phosphoprotein Assays

Cell signaling data of common nodes (pERK1/2, pEGFR, pHer-3, pHer-3, pHer-4, etc.) were collected using standard immunoblotting, in cell Western, or LUMINEX assay (Biorad, Hercules, Calif.). Immunoblotting was performed by normalizing cell lysates to total protein content as determined by BCA assay (Pierce) and running on SDS-PAGE 4-12% tris-acetate gels (Invitrogen). These were transferred to nitrocellulose then probed with corresponding primary antibodies (9106 pERK, 2236 pEGFR, 4791 pHer-3, 4757 pHer-4, Cell Signaling, Danvers, Mass.) and secondary IR-Dye conjugate antibodies (IR-Dye700/800, Rockland). Membranes were scanned using a LI-COR ODYSSEY IR scanner (Licor Systems, Inc., Lincoln, Nebr.). In cell Western analyses were similarly performed in black-walled 96 well plates and using correspondingly higher dilutions of antibodies.

Novagen bead kits were used for phosphorylated Her-2 (pTyr) and total EGFR and Her-2 determination (EMD Sciences) and BIOPLEX bead kits were used for phosphorylated ERK1/2 ($Thr_{202}/Tyr_{204}$, $Thr_{185}/Thr_{187}$). Phosphorylated EGFR (pTyr) determination was performed with BIOPLEX bead kits for dose responses and with Novagen bead kits for time courses. The fluorescent beads are coated with antibodies that bind target proteins in cells lysates and the assays are designed to work with a BIOPLEX 200 System (BioRad, LUMINEX technology). Linearity of the pTyrEGFR and pERK1/2 Bio-Rad assays was checked using varying ratios of stimulated lysates from hTMSC and results were used to determine the optimal loading per well. For phosphoprotein detection 10 μg of protein lysates and 5 μg for total protein detection from each sample were incubated overnight in filter plates (Millipore, Billerica, Mass.) with the appropriate antibody-bead conjugates. Unbound proteins were washed away by vacuum filtration of the plate, trapping the beads in the well. Beads were rinsed with vendor-supplied buffers and incubated with a biotinylated antibody specific for a second epitope on the target. Beads were rinsed again and incubated with streptavidin phycoerythin (Strep-PE), fluorescently tagging the antibody bound to the second epitope. The beads are intrinsically fluorescent at a wavelength matched to the target protein in the BIOPLEX software, hence, intensity of PE fluorescence relative to the fiduciary fluorescence of the bead allows quantification of the target protein. Total EGFR and Her-2 fluorescence were normalized to a standard curve generated with increasing concentrations of the extracellular domain of EGFR provided by the manufacturer (Novagen). Phosphorylated protein signals were normalized to the signal of an unstimulated lysate for the time course experiments.

In Vitro Inhibition Experiments

Low passage MCF7 cells (ATCC) were plated into 12 well plates at 250,000 cells per well in serum containing medium and incubated for 48 hours. Cells were then serum starved for 5 hours prior to ligand treatment. Inhibition experiments which blocked Her-4 with anti-Her-4 antibody clone H4.72.8 (Millipore #05-478) were pretreated with 10 μM antibody 30 minutes prior to subsequent treatments. $IC_{50}$ measurements were made by dosing cells with concentrations of bivalent NRG ligand (C34) in the range of 1 μM to 1 fM for 10 minutes followed by a pulse of 3 nM NRG for an additional 10 minutes (this dose of NRG and endpoint time were validated by generating a NRG dose response curve for MCF-7 cells in the concentration range 1 μM to 1 fM for 20 minutes. 3 nM NRG was the lowest dose that produced near maximal pERK signal at 20 minutes). Following all stimulation experiments cells were placed on ice, medium aspirated, washed with ice cold PBS, and lysed with lysis buffer Calbiochem # FNN0011; 10 mM Tris, pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS, 0.5% deoxycholate, 1 mM PMSF, protease inhibitor cocktail (Sigma Cat. #P-2714) and two phosphatase inhibitor cocktails (Sigma Cat. #P28504 and P5726).

Cell Survival and Apoptosis Assays

MCF-7 cells were treated as described above and evaluated for viability at various timepoints post treatment. Cells were subjected to either a flow cytometric assay to measure the PI positive population or terminal deoxynucleotidyl transferase dUTP nick end labeling (TUNEL) staining. PI staining was performed by diluting PI in growth medium following resuspension of trypsinized cells from each condition. Cells were then directly read on an Acuri Flow cytometer. Unstained MCF-7 cells were used as a negative control to set the analysis gate and calculate percent PI positive. TUNEL staining was performed on cells according to the manufacturer's instructions (Trevingen).

Migration Assays/Transwell Assays

HTS FLUOROBLOCK transwell well chambers (Becton Dickinson) for a 24 well plate format were seeded with hTMSCs in expansion medium supplemented with mitomycin-c. After seeding and attachment for 2 hours the chambers were transferred to their respective conditions, and cells were allowed to migrate for 12 hours. At the end of the experiment the upper chambers were transferred to 4% formaldehyde, washed twice in PBS then incubated in SYTOX-16 nuclear stain (Invitrogen) for 15 minutes. These were again washed with PBS then placed in a clean 24 well plate and read using a SPECTRAMAX M2e multi-well fluorescent plate reader (Molecular Devices Corp., CA). A standard curve correlating fluorescence with cell number was obtained by plating known numbers of cells in a 12 well plate in culture medium containing mitomycin-C (Calbiochem). Standard cell numbers were confirmed by a ViCell hemacytometer (Beckman-Coulter, Fullerton, Calif.).

Time Lapse VidoMicroscopy Assays a) Surface Preparation

A solution of 3 μg/mL of human fibronectin (FN, Sigma) in PBS was used to coat the bottom of a glass-bottom 24-well plate (MatTek) for 2 hours at room temperature, followed by two PBS washes. A 1% (w/v) of BSA solution was then added to each well to block any uncoated regions on the glass for 1 hr at room temperature. Each well was then washed three times with PBS, and the plate was then UV-sterilized for 30 min.

b) CMFDA-Cell Tagging

A 1 μM solution of CELLTRACKER Green (5-Chloromethylfluorescein diacetate) from Molecular Probes (Invitrogen) was made by adding 10 μL of stock CMFDA (1 mM) to 10 mL of a serum-free DMEM media containing: 1% L-glutamine, and 1% penicillin/streptomycin. A 70-80% confluent htMSC petri dish washed with 10 mL of sterile PBS followed by the addition of 10 mL of the CMFDA-containing serum-free DMEM media. Cells were then incubated at 37° C., 95% humidity and 5% $CO_2$ for 20 minutes. CMFDA-containing medium was then aspirated and replaced with 10 mL serum-free DMEM media and incubated (37° C., 95% humidity, 5% $CO_2$) for 30 minutes. Cells were then washed with sterile PBS followed by treatment with 5 mL of trypsin (1×) solution. Upon cell detachment, adding 10 mL of growth medium blocked trypsin action, and cell solution was spun down at 1000 rpm for 5 minutes. Growth media was then aspirated and cell pellet was resuspended in 5 mL of quiescent media. Cell solution was counted and diluted in quiescent media to give a concentration of 4000 cells per mL. In a 24-well plate, 1.5 mL of cell solution was added per well to seed about 6000 cells per well or about 5000 cells per cm$^2$. Cells were allowed to seed for 16-24 hours at 37° C., 95% humidity, 5% $CO_2$ conditions. After initial seeding time, medium was aspirated and replaced with stimulation medium (quiescent medium containing ligand at known concentration). The ligand solutions were prepared just before stimulation and maintained at 37° C. Stimulation was carried out for 6 hours before beginning imaging.

c) Time-Lapse Microscopy and Data Analysis

To generate time-lapse movies of cells migrating on the 2D FN coated surfaces, GFP-widefield images were taken every 10 min for 12 h using a BD CARVII spinning disk confocal with an AXIO OBSERVER Zeiss microscope equipped with environmental control (37° C., 95% humidity, 5% $CO_2$). Cells were imaged using a field of view of 1306×13006 um with 2.551×2.551-um pixels. All movies with the slightest drifts in x or y-direction were assessed and were not included for further analysis. Imaris (Bitplane, Zurich, Switzerland) was used to visualize the 2D time-lapse images. The spots function was used to calculate centroids of fluorescent CMFDA-htMSCs and migratory tracks of individual cells were generated by using the Brownian motion tracking algorithm (H.-D. Kim et al, 2008). All generated tracks were then manually verified for accuracy and modified when the automated logarithm presented errors. Cells undergoing division, death as identified as the release of fluorescence, or blebbing were not tracked. Additionally, cells were seeded on a surface at a low density to minimize any cell-to-cell contact. Wind-Rose plots were generated from the tracks produced from randomly choosing 50 tracks from the motile population and overlaying the starting coordinates at the origin of the plots to graphically represent average cell dispersion during migration. Only tracks longer than 2 hrs that had migrated independently without physical contact with other cells were used for the calculation of directional persistence. To calculate cell speed cell tracks were used as long as their migration was independent of any physical contact with other cells and no cell death or division occurred during their tracks. Average individual speeds (S) were calculated from individual cell tracks by averaging the distances over the time interval. Mean squared displacements (MSD), $<d^2>$, at various time intervals (t) were calculated using the method of nonoverlapping intervals (Dickinson and Tranquillo, 1993) and directional persistence time (P) was obtained by fitting data to the persistent random walk model (PRW):

$$\langle d^2 \rangle = 2S^2 P \left[ t - P \left( 1 - e^{-\frac{t}{P}} \right) \right] \quad (3.1)$$

Results

Activation of EGFR and ERK1/2 Signaling by Bivalent EGF-containing Ligands

Figure 47:
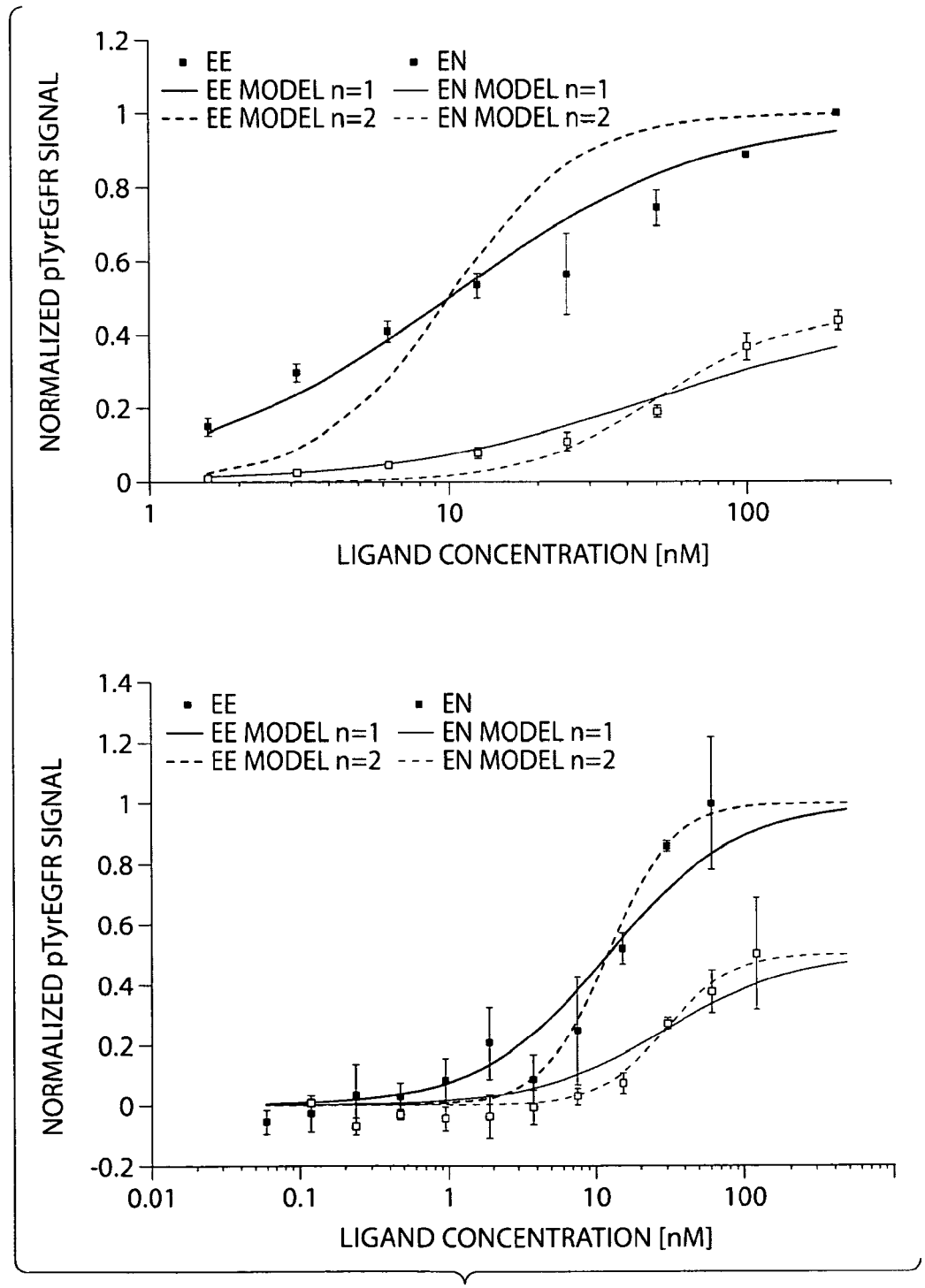
FIG. 47 shows pTyrEGFR dose-response for EE and EN at 1 and 15 minutes. hTMSC were stimulated for 1 (A) or 15 minutes (B) with serial dilutions of EE or EN. Lysates were collected according to BioRad protocol and pTyrEGFR fluorescence levels were measured by LUMINEX technology. Data were normalized by the average signal of the maximum EE concentration. The experimental data were fitted to a Hill-function of first (solid line) and second-order (dashed line). For EN, the model was weighted by the signal ratio at maximum concentration. At 15 minutes the models plotted here have an $EC_{50}$ of 10 nM for EE and 50 nM for EN. Data are shown from n=3 biological replicates.

The dose response for activation of EGFR in hT-MSC by the bivalent ligands EE and EN was examined, using a pan-phospho antibody. Stimulation by EGFR by canonical ligands such as EGF typically leads to a dramatic increase in pEGFR within a minute, peaking in the first few minutes, and a slow decay over 1-2 hr, as was previously illustrated for stimulation of hTMSC. To assess dose-response, pY-EGFR was measured after 1 min and 15 min of stimulation by EE or EN (FIG. 47). The data are best fit with a two parameter model including a Hill coefficient as shown in equation 3.2, where L is the ligand concentration and $EC_{50}$ is a parameter representing the dose of ligand which produces a half maximal response.

$$\Theta = \frac{L^2}{L^2 + EC50} \quad (3.2)$$

An $EC_{50}$ of 10 nM for stimulation by EE at both the 1 min and 15 min time points was determined (FIG. 47). This value is slightly higher than the $EC_{50}$ for wild type EGF. At equimolar concentrations of bivalent ligand (which results in half the concentration of E ligand for the case of EN compared to EE), EN stimulates a fraction (at most, half) of the signal of EE for pY-EGFR at both 1 min and 15 minutes post-stimulation, up to ligand concentrations of 100 nM. The different ways that EE and EN ligands can activate EGFR in the context of hTMSC, which are known to express about 10,000 EGFR, 2,000 Her-2, moderate levels of Her-3 and no Her-4 were considered. Options for bivalent EE ligand include: (i) bivalent EE binds to individual EGFR and acts essentially through only one EGF moiety, allowing both EGFR homodimers and EGFR-Her-2 heterodimers to form (ii) bivalent EE binds to EGFR and either stabilizes pre-formed homodimers or drives homodimerization to the exclusion of heterodimerization with Her-2 (iii) bivalent EE ligand binds to individual EGFR through a single EGF as described in (i), and two such individual, bivalent ligand-occupied receptors homodimerize, allowing recruitment of additional free EGFR into oligomers which may also include Her-2.

In all of these scenarios, it is possible for essentially all cell surface EGFR to bind ligand and become phosphorylated, through interactions with other ligand-bound EGFR or with Her-2. It is possible that dimer ligands may alter the kinetics of phosphorylation/dephosphorylation compared to wtEGF, by imposing steric constraints on the receptors, fostering different ratios of homo and heterodimers, or altering the ability of the EGFR to interact with other cell surface receptors that are implicated in transactivation. The theoretical limit of EGFR-Her-2 heterodimers in these cells is about one third of total possible EGFR in heterodimers when all EGFR are occupied and dimerized (i.e., 2000 heterodimers and 4000 homodimers). Further, differences in the relative phosphorylation of particular phosphosites may be affected by the receptor dimer composition.[108]

Using a similar analysis for the binding of bivalent EN, the possibilities are that (i) bivalent EN binds to individual EGFR and acts essentially through only one EGF moiety, allowing both EGFR homodimers and EGFR-Her-2 heterodimers to form (ii) bivalent EN binds to EGFR and drives heterodimerization with Her-3 to the exclusion of heterodimerization with Her-2 (iii) bivalent EN ligand binds to individual EGFR through a single EGF as described in (i), and two such individual, bivalent ligand-occupied receptors homodimerize, allowing recruitment of Her-3 into oligomers which may also include Her-2; (iv) bivalent EN binds to Her-3 via a single NRG moiety, allowing Her-2-Her-3 heterodimerization and possibly oligomerization, as well as Her-3-Her-3 homodimerization (v) bivalent EN binds to individual EGFR or Her-3 but heterodimers are sterically inhibited from forming.

If scenario (i) were predominant, it is expected that responses from EE and EN are similar, presuming similar receptor-ligand affinities. The degree to which Her-3 acts as a "sink" as described in scenario EN (iv) or (v) is difficult to estimate precisely, because the total number of Her-3 relative to EGFR is unknown in these cells (presumed to be <10,000), but is a plausible explanation for the effects observed. An alternative explanation is that EGFR-Her-3 heterodimers are relatively ineffective in these cells at phosphorylating EGFR. A pan-pY antibody was used to assess phosphorylation. It is also possible that the antibody reacts with different affinity to different pY sites on the EGFR, or that more than one antibody can bind to a single pYEGFR if it is phosphorylated on different sites, so that different patterns of pY on EGFR might result in different signal strength even if the total number of pYEGFR is the same.

The time course of EGFR and Her-2 activation using wtEGF and bivalent EE was examined, under conditions of comparable $EC_{50}$ and under conditions that should saturate the EGFR (i.e., concentrations 3-10 fold above $EC_{50}$).

The EE saturating concentration of 100 nM was chosen because it is 3 times higher than the $EC_{50}$ of EE. For EGF, 30 nM was used which is 30 times above its $EC_{50}$, therefore signal maximum should be achieved, also this concentration is the same as the $EC_{50}$ of EE, providing a means in each case of comparing EE and EGF at equimolar concentrations. Cells were stimulated with 15 nM of EE because in this case the number of EGF molecules (2 EGF molecules in EE) would be identical to 30 nM of EGF and with 1 nM EGF ($EC_{50}$ of wtEGF).

Figure 48A:
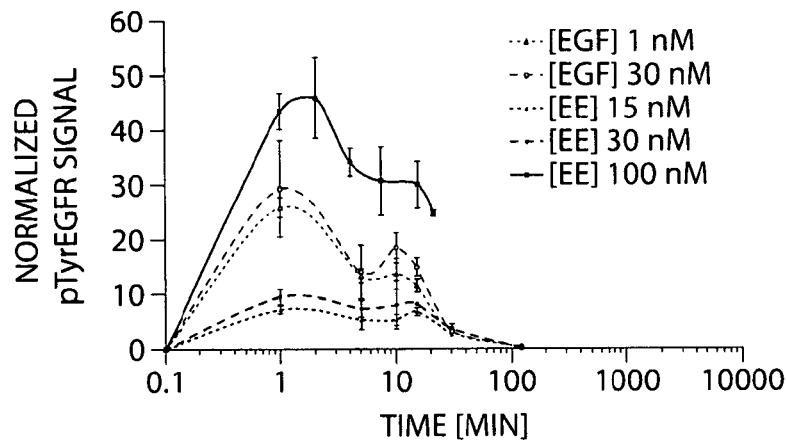
FIG. 48 shows a time course of EE and EGF stimulation. Data plotted for EGF-stimulated and EE-stimulated. A, B) Time course of bivalent EGF ('EE') and wtEGF stimulation in hTMSC cells. Lysates were collected and pTyrEGFR (A) and pTyrHER2 (B) fluorescence levels were measured by LUMINEX technology. The figure represents normalized levels of pTyrEGFR and pTyrHER2 with respect to an unstimulated control. Data are shown with n=3 biological replicates. C, D) Time course of bivalent EGF ('EE') and wtEGF stimulation in HeLa cells at 100 nM. Errors are (+/−) standard error of the mean for n=2 independent experimental replicates.
Figure 48B:
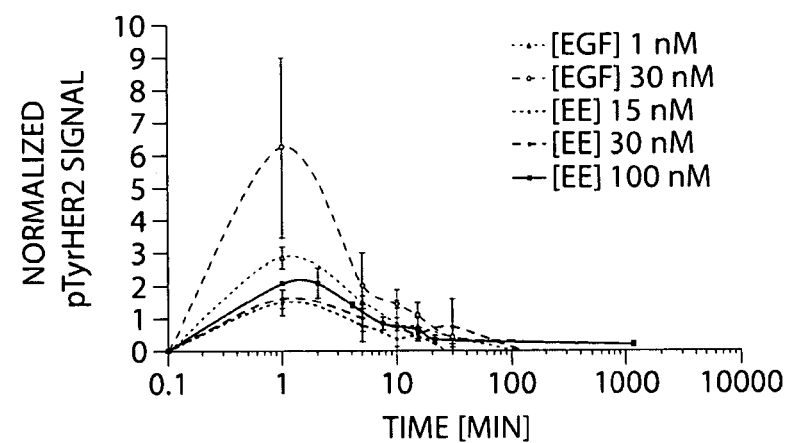

From the data shown in FIGS. 48A and 48B, comparing each condition at equimolar concentration, EGF-stimulated cells show both a stronger EGFR and Her-2 phosphorylation than EE stimulated cells. For 100 nM EE stimulation (solid blue curve), the phosphorylated EGFR levels are considerably higher over the whole course of the experiment. This strong increase of phosphorylated EGFR for EE compared to EGF is not correlated with an increase in pTyrHER2 signal. Even at 100 nM EE, the phosphorylated Her-2 signal is lower than that of 1 nM EGF.

Weaker Her-2 activation with bivalent EGF, EE, indicates that Her-2 can be prevented from dimerizing with EGFR by the bivalent EE ligand. At the saturating concentrations (i.e., concentrations of ligand several-fold excess above $EC_{50}$) it would be expected that all EGFR is ligand-bound and phosphorylated, and thus comparable levels of receptor activation for wtEGF and for the bivalent EE at saturating conditions is expected. The more robust phosphorylation signal for bivalent EE may indicate that EE alters phosphorylation patterns and/or renders pY-EGFR less susceptible to phosphatase activity.

The pY-HER2 levels are significantly reduced for the bivalent ligand EE case. Taken together, the results in FIGS. 48A and 48B suggest that EE is capable of inhibiting EGFR-Her-2 heterodimerization, or at least, of allowing Her-2 to become activated if such dimers form.

The kinetics of EGFR activation and downstream signaling using HeLa cells were analyzed, as they express abundant EGFR and Her-2. Using 100 nM EGF and EE a marked increase (almost two-fold) of EGFR phosphorylation is observed in the EE-stimulated case versus wtEGF over much of the early stimulation time course (<100 minutes). This observation suggests a differential effect exerted by EE versus wtEGF.

Figure 48C:
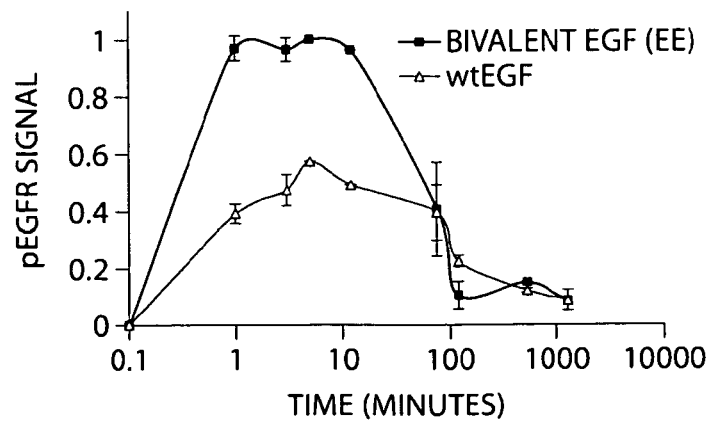
Figure 48D:
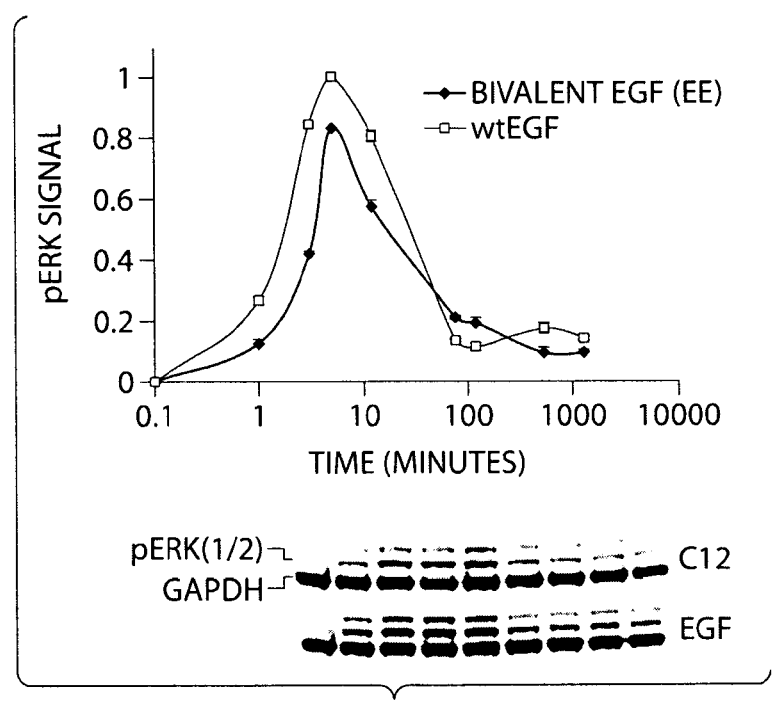

Stimulation of EGFR prominently activates the downstream kinase pathway leading to ERK1/2, a key signaling node integrating multiple signaling networks.[17, 25] Despite the more robust EGFR signal elicited by EE bivalent ligands compared to wtEGF (FIG. 48C), activation of ERK1/2 is substantially lower for stimulation by EE compared to wtEGF (FIG. 48D). This observation is consistent with previous findings which have shown reduced signaling potency of EGFR homodimers compared to EGFR-Her-2 heterodimers. Taken together these data suggest that EE is able to bias EGFR dimerization toward homodimers compared to heterodimers.

Manipulation of EFGR Family Signaling Pathways with Bivalent NRG-Containing Ligands.

It would be expected that the bivalent neuregulin (NN) ligand is capable of shutting off NRG-mediated signaling in cells where Her-3 is expressed and where Her-4 is either not expressed or is able to be specifically excluded from binding NRG (e.g., through the use of blocking antibodies), because Her-3 is kinase-deficient, recruitment of Her-3 homodimers would produce a null signaling outcome. Two cell types were used that have known Her-3 and Her-4 expression profiles; MCF-7 cells known to express both Her-3 and Her-4; and htMSCs known to express only Her-3. Signaling mediated by wtNRG is typically robust and can be readily detected by measuring pERK1/2.

Figure 49:
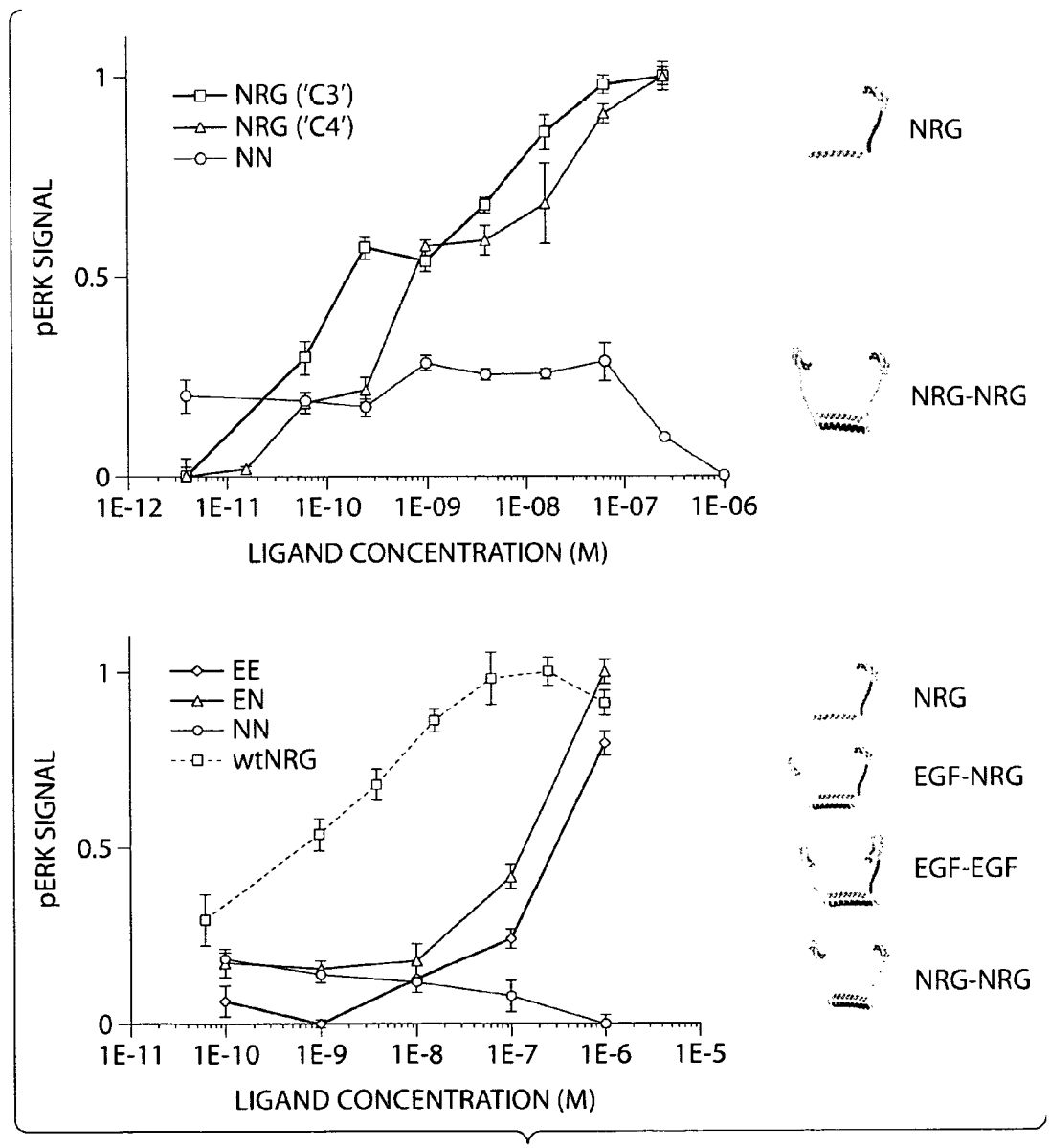
FIG. 49 shows signal silencing in MSC cells with bivalent NRG (NN). The effect of stimulating MSCs with a range of doses of various bivalent ligand combinations, including comparisons of NN signaling. Signal is measured as pERK1/2 levels relative to unstimulated minima. Errors are (+/−) standard error of the mean for n=3 independent experimental replicates.

When hTMSC, which express Her-3 but not Her-4, are stimulated with monovalent engineered NRG1, a robust dose-dependent pERK response is observed that is similar for either configuration of the engineered ligand and similar to wtNRG1 (FIG. 49). In stark contrast, stimulation with bivalent NN ligand appears to activate ERK1/2 modestly at low doses, but this mild effect is erased at higher ligand doses, suggesting that the bivalent NN ligand captures Her-3 in homodimers—which are inherently incapable of downstream signal propagation.

Dose responses with bivalent EGF (EE) and mixed ligand EGF-NRG (EN) show a rightward shifted $EC_{50}$ (mid nM) and a steeper response region consistent with bivalent avidity. One possible explanation for the rightward shifted $EC_{50}$ is the exclusion of Her-2 from receptor dimer complexes. It has been demonstrated that Her-2 plays a role in increasing ligand binding affinity of both EGF to EGFR and NRG to Her-3 (or Her-4) and in the case of NRG lowered the $EC_{50}$ by one order of magnitude, thus suggesting a stabilizing role for Her-2, the exclusion of which could contribute to a reduction in apparent affinity as evidence by the rightward shifted $EC_{50}$.

Figure 50A:
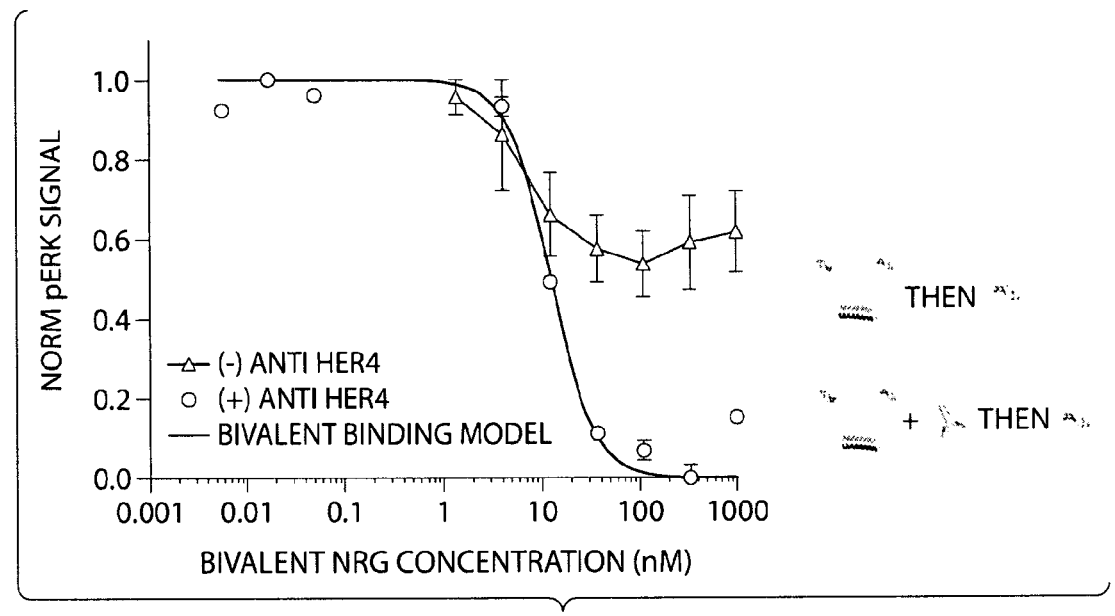
FIG. 50 shows signal silencing in MCF-7 cells with bivalent NRG (NN). (A) The $IC_{50}$ of N2 versus a 3 nM NRG challenge and effect of Her-4 signaling are depicted. Errors are (+/−) standard error of the mean for n=3 independent experimental replicates. (B) a representative immunoblot of an N2 $IC_{50}$ experiment.
Figure 50B:
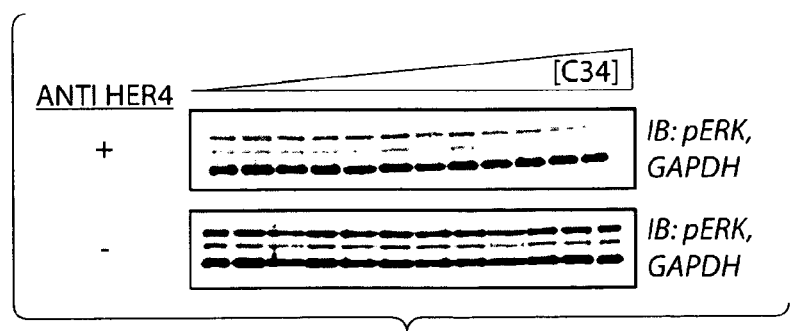

The ability of the bivalent NN ligand to silence signaling through Her-3 suggested a possible therapeutic use in cancer cell signaling. Responses in a cancer cell line were investigated in MSCF, which expresses Her-3 at a much more robust level than hTMSC. Because MCF-7 also express Her-4, which also binds NRG1, they are a model for analyzing the effects of co-expression of Her-4. FIG. 50 depicts data from an inhibition experiment where bivalent neuregulin (NN) is used to inhibit signaling in a dose-dependent manner versus a 3 nM wtNRG challenge. Signal silencing is mediated by the putative recruitment of Her-3 homodimers to produce a silent phenotype.

Pretreatment of MCF-7 cells with an anti-Her-4 (ECD) antibody specifically excludes Her-4 from ligand binding and thus excludes Her-4 from participating in signaling following wtNRG stimulation. Absence of anti-Her-4 antibody pretreatment reconstitutes wtNRG-stimulated signaling. The NN inhibition curve (circles) was fit with a second order model to yield an $IC_{50}$ of 12 nM and a Hill coefficient of n=2, which is indicative of bivalent avidity.

Taken together, results from time course experiments in HeLa and inhibition in MCF-7 indicate that bivalent ligands may recruit respective Her receptors into dimeric complexes of known composition and produce expected signaling outcomes consistent with known mechanisms of ligand binding and receptor dimerization.

Stimulation of MSC with Bivalent Ligands Influences Cell Migration

Figure 51:
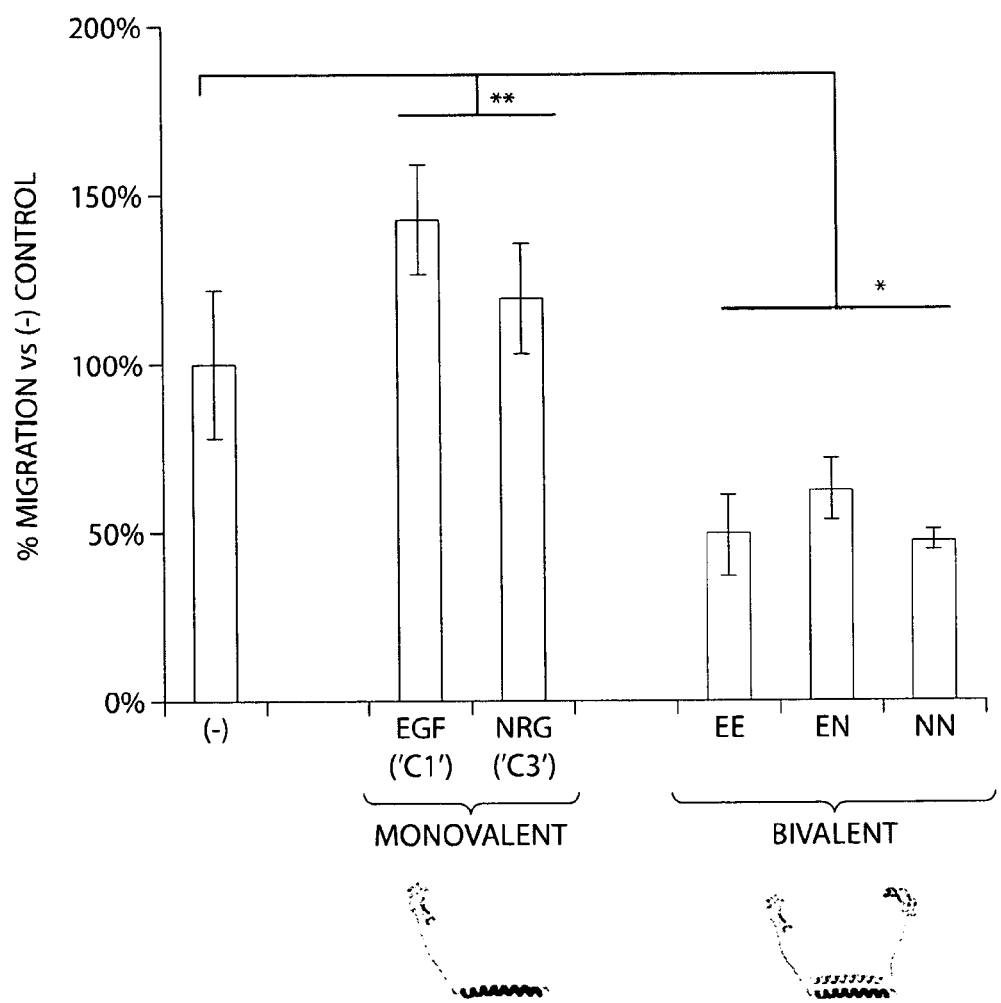
FIG. 51 shows inhibition of cell migration with bivalent ligands versus natural ligand stimulation. Inhibition of cell migration with bivalent ligands forces Her-1-1, Her-1-3 and Her-3-3 receptor dimers versus natural ligand stimulation. Errors are (+/−)standard error of the mean for n=3 independent experimental replicates *p=0.01, **p=0.05 vs (−) control; n=3; error bars: 99% C.I. All ligands were dosed at 100 nM.

The effects of EGF family ligands on cell migration are well documented.[109] The stimulation of EGFR with EGF can give rise to increases in both speed and persistence. To screen bivalent ligands for possible effects on cell migration phenotypes, transwell migration assays were used. Transwell assays measure chemotactic migration and can give a rapid readout of ligand effects that arise from modulated speed or persistence. Although in a transwell experiment one cannot determine speed and persistence, modulation of these parameters would manifest itself as a difference in transwell migration. As seen in FIG. 51 monovalent ligands stimulate increased transwell migration by approximately 40% and 25% for EGF and NRG, respectively. In contrast, all bivalent ligands produce reductions in transwell migration relative to an unstimulated control. This is consistent with previous findings in which reduced migration is observed for cells in which the predominant signaling mode is through Her-1 homodimers.[3, 60]

Figure 52:
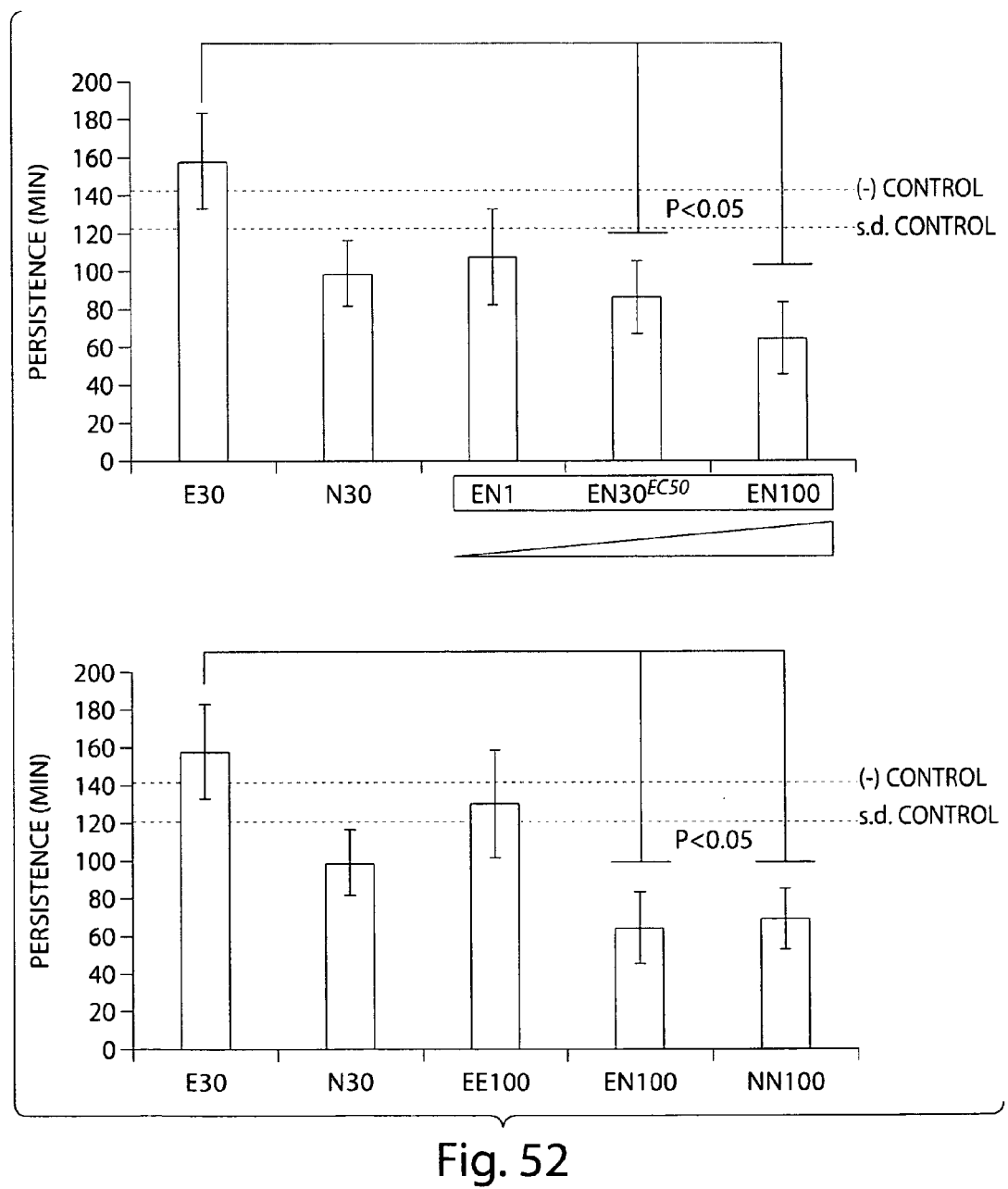
FIG. 52 shows persistence analysis: time-lapse microscopy of 2D cell migration. Bivalent ligand stimulation with EN results in reduced directional persistence that is dose dependent (top graph). Both EN and NN resulted in reduced directional persistence of approximately 55% versus the EGF stimulated condition (bottom plot).

Although limited data are available on the effect of forced Her-1-Her-3 heterodimers on migration it appears that exclusion of Her-2 from signaling complexes can contribute to this effect for all the bivalent ligand combinations. Reduced transwell migration of cells stimulated with bivalent ligands may result from the exclusion of Her-2 from signaling complexes, as Her-2 increases cell persistence.[110, 111] If this is the case then the physical parameters which underlie cellular motility should reflect this change. In the context of transwell migration the parameter of directional persistence can be expected to play an important role in the fate of a cell. It is reasonable to expect that a cell with reduced directional persistence would encounter a transwell pore with a different frequency than a cell with high directional persistence. If the frequency of encounters with a pore is reduced in cells with reduced directional persistence then the number of opportunities to migrate through a pore would also be reduced. In the case of a membrane with a sparse arrangement of pores relative to the number of cells this is a reasonable assumption. FIG. 52 illustrates the effect of bivalent ligands on cellular persistence.

As expected, the bivalent ligands EN and NN appear to reduce the directional persistence of cells. In particular, this effect appears to be dose dependent in the case of EN (FIG. 52, top), where the effect becomes statistically different than the control at the $EC_{50}$ of EN. In the case of EN and NN, the effect is equivalent in magnitude and appears to reflect the transwell migration results at the same dose (100 nM). The reduction in directional persistence at this dose is approximately 55% versus the unstimulated control. In terms of cell motility this means that a cell spends half as long moving in one direction and will explore a smaller area over long times than cells with higher persistence. By comparison the reduction in transwell migration was 50% for bivalent ligand stimulation at this dose.

Stimulation of Cells with Bivalent Ligands Influences Cell Survival and Proliferation The human telomerase reverse transcriptase immortalized human mesenchymal stem cells used in the migration studies described above have been shown to survive serum free conditions for several days if cultured at sufficiently high confluence (>50%). While cell division is greatly reduced these cells can tolerate the absence of serum and remain quiescent for a period of 3-7 days before undergoing programmed cell death. This behavior presents a convenient breakpoint in cell fate that can be influenced by the addition of survival stimuli such as EGF or NRG. Previous work has shown that MSCs can be rescued from stressful or pro-death conditions by addition of EGF or NRG. The ability of wild type ligands to rescue MSCs from apoptosis during stressful conditions is mediated by signaling through the Her receptors which stimulates a number of pro-survival down stream effectors. Variation in cell survival outcomes resulting from stimulation with any of the bivalent ligands as compared to natural ligands would indicate modulated signaling related to biased receptor dimerization.

Figure 53:
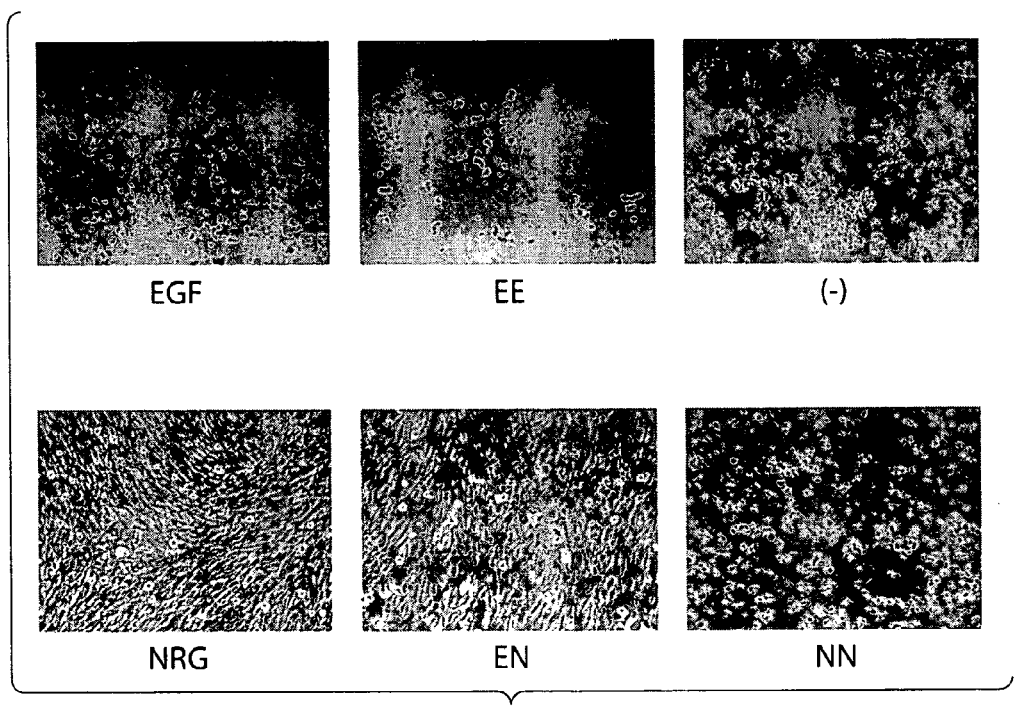
FIG. 53 shows micrographs of cell cultures of htMSCs at 30 days. Stimulation with NRG and EN may promote viability in long term serum free cultures. EGF, EE, and NN consistently result in reduced viability under these conditions. The absence of viability in NN cultures corresponds with the expected outcome given the silencing of signaling. Comparison of (−) with NN illustrates similar outcomes. Scale bar is 100 μm.

FIG. 53 shows a set of photomicrographs of MSCs cultured for 30 days in serum free medium containing the indicated conditions. Medium was changed every three days during the 30 day period. After a period of 10 days the wells containing EGF and EE showed early signs of apoptosis and reduced rates of medium acidification as evidenced by phenol red indicator color.

After 14 days the wells containing NN and (−) showed similar characteristics. At 21 days the wells containing EGF, EE, NN, and (−) appeared to be completely dead and no longer caused changes in phenol red indicator. Wells containing NRG and EN showed a normal morphology and exhibited signs of metabolism by rapid acidification of medium. The addition of NRG appears to confer a survival advantage under these conditions which is consistent with previous findings. The addition of EN appears to recapitulate this effect even though the presence of an EGF moiety in the bivalent construct might be expected to counteract this effect based on the results from wild type EGF stimulation. The NN condition did not perform better than the (−) control, a result which is entirely consistent with signaling the data showing no stimulation of pERK in MSCs with NN.

The inhibition of signaling observed in MCF-7 cells was expected to also produce phenotypic survival differences under stressful conditions such as serum starvation. The same conditions described in FIG. 49 were used to replicate the signaling effect but were maintained for several days (48 to 96 hours, depending on the experiment).

Figure 54:
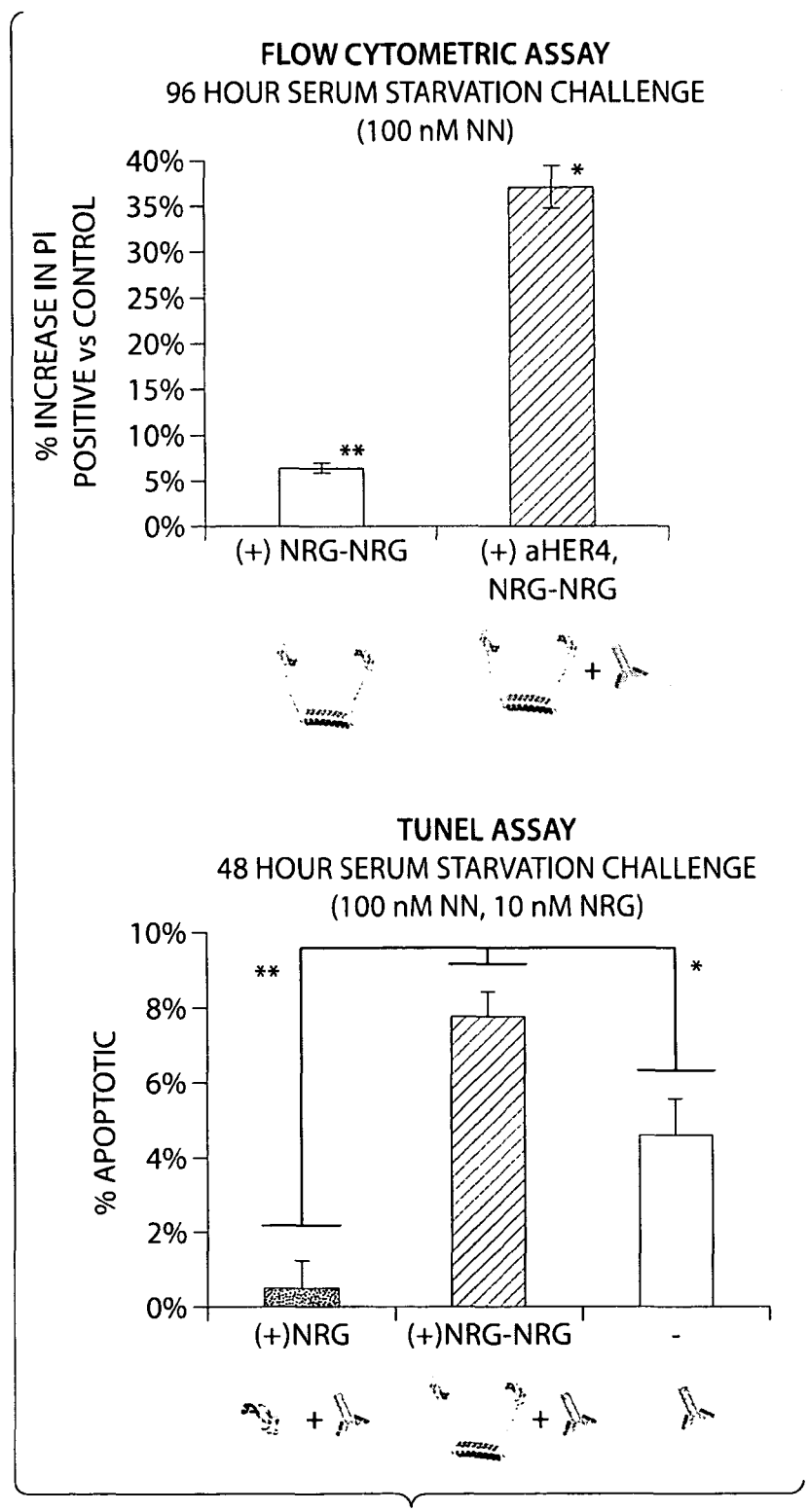
FIG. 54 shows bivalent NRG effect on the survival of serum starved MCF-7 cells. A significant increase in the % PI positive population of MCF-7 cells results from treatment with bivalent NRG under conditions which lead to signal attenuation through the Her-3 and Her-4 mediated pathway. Likewise a significant increase in apoptotic (TUNEL positive) cells is seen by 48 hours under the same conditions. These results support the proposed signaling attenuation mechanism. Left plot: *p=0.01 vs control (10 nM NRG), **p=0.02 vs control (10 nM NRG), n=3, (+/−) SEM; Right plot *p=0.009 NN vs (−) control, **p=0.001 NN vs 10 nM NRG; p=0.01 10 nM NRG vs (−), n=3, (+/−) s.d.

The extended time period under these conditions permits sufficient differences in survival to be detected. Two types of assays were performed to study this effect in MCF-7 cells: a cell permeabilization assay which is a late marker of apoptosis and a terminal deoxynucleotidyl transferase dUTP nick end labeling (TUNEL) assay which measures breaks in double stranded DNA, a mid to late maker of apoptosis. In the cell permeabilization assay a total propidium iodide (PI) positive population was measured using flow cytometry and gives a relative measure of cell death. TUNEL labeling is more specific to apoptosis and gives a quantitative indication of cells undergoing programmed cell death. FIG. 54 shows the results of these two assays for MCF-7 cells cultured under the indicated conditions.

Imposing conditions which result in signal attenuation also result in increased cell death under serum starvation. An increase of 35% in PI % cells is seen over the control condition (FIG. 54, left). The exclusion of anti-Her-4 antibody treatment allows NRG to rescue cells from death (7% PI+) and reflects the signaling data shown earlier. The TUNEL analysis shows the same effect. In this case the treatment that results in signal attenuation produces 8% apoptotic cells vs <1% in the positive control. Phenotypic results such as these agree well with the signaling data and support the proposed mechanism of signal attenuation. These data suggest the exclusion of Her-3 receptors from productive signaling complexes through the action of bivalent NRG.

REFERENCES

1. Jones, R. B., Gordus, A., Krall, J. A. & Macbeath, G. A quantitative protein interaction network for the ErbB receptors using protein microarrays. Nature (2005).

2. Yarden, Y. & Sliwkowski, M. X. Untangling the ErbB Signaling Network. Nature Reviews—Molecular Cell Biology 4, 5 (2001).
3. Muthuswamy, S. K., Gilman, M. & Brugge, J. S. Controlled Dimerization of ErbB Receptors Provides Evidence for Differential Signaling by Homo- and Heterodimers. Molecular and Cellular Biology 19, 6845 (1999).
4. Caplan, A. I. Review: Mesenchymal Stem Cells: Cell-Based Reconstructive Therapy in Orthopedics. Tissue Engineering 11, 1198-1211 (2005).
5. Connolly, G. R., Tiedeman J, et al. Autologous marrow injection as a substitute for operative grafting of tibial nonunions. Clin Orthop Relat Res, 259-270 (1991).
6. Garg, N. K. & Gaur, S. Percutaneous autogenous bone-marrow grafting in congenital tibial pseudarthrosis. Journal of Bone & Joint Surgery, British Volume 77, 830-831 (1995).
7. Healey, Z. P., McDonnell J M, et al. Percutaneous bone marrow grafting of delayed union and nonunion in cancer patients. Clin Orthop Relat Res, 280-285 (1990).
8. Brodke, D. et al. Bone grafts prepared with selective cell retention technology heal canine segmental defects as effectively as autograft. J Orthop Res 24, 857-866 (2006).
9. Muschler, M. Y., Nitto H, et al. Selective retention of bone marrow-derived cells to enhance spinal fusion. Clin Orthop Relat Res, 242-251 (2005).
10. Muschler, N. H., Matsukura Y, et al. Spine fusion using cell matrix composites enriched in bone marrow-derived cells. Clin Orthop Relat Res, 102-118 (2003).
11. Patterson, T. E., Kumagai, K., Griffith, L. & Muschler, G. F. Cellular Strategies for Enhancement of Fracture Repair. The Journal of Bone and Joint Surgery 90, 111 (2008).
12. Jones, A. L. et al. Recombinant Human BMP-2 and Allograft Compared with Autogenous Bone Graft for Reconstruction of Diaphyseal Tibial Fractures with Cortical Defects. A Randomized, Controlled Trial. The Journal of Bone and Joint Surgery 88, 1431 (2006).
13. Masi, L. et al. In Vitro Structural and Functional Relationships Between Preosteoclastic and Bone Endothelial Cells: A Juxtacrine Model for Migration and Adhesion of Osteoclast Precursors. Journal of Cellular Physiology 162, 199-212 (1995).
14. Bruder, S. P., Fink, D. J. & Caplan, A. I. Mesenchymal stem cells in bone development, bone repair, and skeletal regeneration therapy. J Cell Biochem 56, 283-94 (1994).
15. Barou, O. et al. Relationships between trabecular bone remodeling and bone vascularization: a quantitative study. Bone 30, 604-612 (2002).
16. Kolf, C. M., Cho, E. & Tuan, R. S. Mesenchymal stromal cells. Biology of adult mesenchymal stem cells: regulation of niche, self-renewal and differentiation. Arthritis Res Ther 9, 204 (2007).
17. Pinkas-Kramarski, R. et al. Diversification of Neu differentiation factor and epidermal growth factor signaling by combinatorial receptor interactions. EMBO J. 15, 2452-2467 (1996).
18. Tzahar, E. et al. A hierarchical network of interreceptor interactions determines signal transduction by Neu differentiation factor/neuregulin and epidermal growth factor. Molecular and Cellular Biology 16, 5276-5287 (1996).
19. Tamama, K., Fan, V. H., Griffith, L. G., Blair, H. C. & Wells, A. Epidermal Growth Factor as a Candidate for Ex Vivo Expansion of Bone Marrow-Derived Mesenchymal Stem Cells. Stem Cells 24, 686-695 (2006).
20. Griffith, L. G. Emerging Design Principles in Biomaterials and Scaffolds for Tissue Engineering. Annals of the New York Academy of Sciences 961, 83-95 (2002).
22. Bublil, E. M. & Yarden, Y. The EGF receptor family: spearheading a merger of signaling and therapeutics. Current Opinion in Cell Biology 19, 124-134 (2007).
23. Citri, A. & Yarden, Y. EGF-ERBB signalling: towards the systems level. Nat Rev Mol Cell Biol 7, 505-16 (2006).
24. Miettinen, P. J. et al. Epidermal growth factor receptor function is necessary for normal craniofacial development and palate closure. Nature Genetics 22, 69-73 (1999).
25. Gibbs, S. et al. Epidermal growth factor and keratinocyte growth factor differentially regulate epidermal migration, growth, and differentiation. Wound Repair and Regeneration 8, 192-203 (2000).
26. Tokumaru, S. et al. Ectodomain Shedding of Epidermal Growth Factor Receptor Ligands Is Required for Keratinocyte Migration in Cutaneous Wound Healing. The Journal of Cell Biology 151, 209-220 (2000).
27. Maheshwari, G., Wells, A., Griffith, L. G. & Lauffenburger, D. A. Biophysical Integration of Effects of Epidermal Growth Factor and Fibronectin on Fibroblast Migration. Biophysical Journal 76, 2814-2823 (1999).
28. Traverse, S. et al. Research Paper EGF triggers neuronal differentiation of PC12 cells that overexpress the EGF receptor. Current Biology 4, 694-701 (1994).
29. Freeman, M. Reiterative use of the EGF receptor triggers differentiation of all cell types in the *Drosophila* eye. Cell 87, 651-60 (1996).
30. Miettinen, P. J. 2617-2627 (2000).
31. Kratchmarova, I., Blagoev, B., Haack-Sørensen, M., Kassem, M. & Mann, M. 1472-1477 (American Association for the Advancement of Science, 2005).
32. Fan, V. H. et al. Tethered Epidermal Growth Factor Provides a Survival Advantage to Mesenchymal Stem Cells. Stem Cells 25, 1241 (2007).
33. Wang, K., Yamamoto, H., Chin, J. R., Werb, Z. & Vu, T. H. Epidermal Growth Factor Receptor-deficient Mice Have Delayed Primary Endochondral Ossification Because of Defective Osteoclast Recruitment. Journal of Biological Chemistry 279, 53848 (2004).
34. Sibilia, M. et al. Mice humanised for the EGF receptor display hypomorphic phenotypes in skin, bone and heart. Development 130, 4515-4525 (2003).
35. Qin, L. et al. Amphiregulin Is a Novel Growth Factor Involved in Normal Bone Development and in the Cellular Response to Parathyroid Hormone Stimulation. Journal of Biological Chemistry 280, 3974 (2005).
36. Chan, S. Y. & Wong, R. W. C. Expression of Epidermal Growth Factor in Transgenic Mice Causes Growth Retardation. Journal of Biological Chemistry 275, 38693-38698 (2000).
37. Kuznetsov, S. A., Friedenstein, A. J. & Gehron Robey, P. Factors required for bone marrow stromal fibroblast colony formation in vitro. British Journal of Haematology 97, 561-570 (1997).
38. Kimura, A., Katoh, O. & Kuramoto, A. Effects of platelet derived growth factor, epidermal growth factor and transforming growth factor-β on the growth of human marrow fibroblasts. British Journal of Haematology 69, 9-12 (1988).
39. Gronthos, S. & Simmons, P. J. The growth factor requirements of STRO-1-positive human bone marrow stromal precursors under serum-deprived conditions in vitro. Blood 85, 929-40 (1995).
40. Owen, M. E. 731-738 (1987).
41. Satomura, K. et al. Receptor tyrosine kinase expression in human bone marrow stromal cells. Journal of Cellular Physiology 177, 426-438 (1998).

42. Garnett, D. C. et al. Heregulin-stimulated signaling in rat pheochromocytoma cells. Evidence for ErbB3 interactions with Neu/ErbB2 and p85. J Biol Chem 270, 19022-7 (1995).
43. Garnett, D. C. & Cerione, R. A. Oncogenically activated or ligand-stimulated neu kinase stimulates neurite outgrowth in PC12 cells. FEBS Lett 351, 335-9 (1994).
44. Morrissey, T. K., Levi, A. D., Nuijens, A., Sliwkowski, M. X. & Bunge, R. P. Axon-induced mitogenesis of human Schwann cells involves heregulin and p185erbB2. Proceedings of the National Academy of Sciences of the United States of America 92, 1431 (1995).
45. Oshima, M., Weiss, L., Dougall, W. C., Greene, M. I. & Guroff, G. Down-Regulation of c-neu Receptors by Nerve Growth Factor in PC 12 Cells. J. Neurochem. 65, 427-433 (1995).
46. Kim, D. et al. Neuregulin Stimulates Myogenic Differentiation in an Autocrine Manner. Journal of Biological Chemistry 274, 15395-15400 (1999).
47. Fu, A. K. Y. et al. Cdk5 is involved in neuregulin-induced AChR expression at the neuromuscular junction. Nature Neuroscience 4, 374-381 (2001).
48. Dezawa, M. et al. 314-317 (American Association for the Advancement of Science, 2005).
49. Gui, C. et al. Heregulin protects mesenchymal stem cells from serum deprivation and hypoxia-induced apoptosis. Molecular and Cellular Biochemistry 305, 171-178 (2007).
50. Stadelmann, W. K., Digenis, A. G. & Tobin, G. R. Impediments to wound healing. Am J Surg 176, 39S-47S (1998).
51. Herard, A. L. et al. Fibronectin and its alpha 5 beta 1-integrin receptor are involved in the wound-repair process of airway epithelium. American Journal of Physiology—Lung Cellular and Molecular Physiology 271, 726-733 (1996).
52. Deans, R. J. & Moseley, A. B. Mesenchymal stem cells Biology and potential clinical uses. Experimental Hematology 28, 875-884 (2000).
53. Irvine, D. J., Hue, K. A., Mayes, A. M. & Griffith, L. G. Simulations of Cell-Surface Integrin Binding to Nanoscale-Clustered Adhesion Ligands. Biophysical Journal 82, 120-132 (2002).
54. Koo, L. Y., Irvine, D. J., Mayes, A. M., Lauffenburger, D. A. & Griffith, L. G. Co-regulation of cell adhesion by nanoscale RGD organization and mechanical stimulus. Journal of Cell Science 115, 1423-1433 (2002).
55. Hersel, U., Dahmen, C. & Kessler, H. RGD modified polymers: biomaterials for stimulated cell adhesion and beyond. Biomaterials 24, 4385-4415 (2003).
56. Tamama, K., Fan, V. H., Griffith, L. G., Blair, H. C. & Wells, A. Epidermal Growth Factor as a Candidate for Ex Vivo Expansion of Bone Marrow-Derived Mesenchymal Stem Cells. Stem Cells 24, 686 (2006).
57. Wiley, H. S. Trafficking of the ErbB receptors and its influence on signaling. Experimental Cell Research 284, 78-88 (2003).
58. Sliwkowski, M. X. et al. Coexpression of erbB2 and erbB3 proteins reconstitutes a high affinity receptor for heregulin. Journal of Biological Chemistry 269, 14661-14665 (1994).
59. Tzahar, E. et al. Bivalence of EGF-like ligands drives the ErbB signaling network. The EMBO Journal 16, 4938-4950 (1997).
60. Zhan, L., Xiang, B. & Muthuswamy, S. K. 5201-5208 (AACR, 2006).
61. Linggi, B. & Carpenter, G. ErbB receptors: new insights on mechanisms and biology. Trends in Cell Biology 16, 649-656 (2006).
62. Jorissen, R. N. et al. Epidermal growth factor receptor: mechanisms of activation and signalling. Experimental Cell Research 284, 31-53 (2003).
63. Witton, C. J., Reeves, J. R., Going, J. J., Cooke, T. G. & Bartlett, J. M. S. Expression of the HER 1-4 family of receptor tyrosine kinases in breast cancer. The Journal of Pathology 200, 290-297 (2003).
64. Ii, D. J. R. & Stern, D. F. Specificity within the EGF family/ErbB receptor family signaling network. Bioessays 20, 41-48 (1998).
70. Zhang, X., Gureasko, J., Shen, K., Cole, P. A. & Kuriyan, J. An Allosteric Mechanism for Activation of the Kinase Domain of Epidermal Growth Factor Receptor. Cell 125, 1137-1149 (2006).
71. Ogiso, H. et al. Crystal Structure of the Complex of Human Epidermal Growth Factor and Receptor Extracellular Domains. Cell 110, 775-787 (2002).
72. Moll, J. R., Ruvinov, S. B., Pastan, I. & Vinson, C. Designed heterodimerizing leucine zippers with a ranger of pIs and stabilities up to 10-15 M. Protein Science 10, 649 (2001).
73. Zhang, K., Diehl, M. R. & Tirrell, D. A. Artificial polypeptide scaffold for protein immobilization. J. Am. Chem. Soc 127, 10136-10137 (2005).
74. Shen, W., Zhang, K., Kornfield, J. A. & Tirrell, D. A. Tuning the erosion rate of artificial protein hydrogels through control of network topology. Nat. Mater 5, 153-158 (2006).
75. Martin, A., Baker, T. A. & Sauer, R. T. Rebuilt AAA+ motors reveal operating principles for ATP-fuelled machines. Nature 437, 1115-20 (2005).
76. Kaszkin, M., Seidler, L., Kast, R. & Kinzel, V. Epidermal-growth-factor-induced production of phosphatidylalcohols by HeLa cells and A431 cells through activation of phospholipase D. Biochem. J. 287, 1-57 (1992).
77. Oksvold, M. P., Skarpen, E., Lindeman, B., Roos, N. & Huitfeldt, H. S. Immunocytochemical localization of Shc and activated EGF receptor in early endosomes after EGF stimulation of HeLa cells. J Histochem Cytochem 48, 21-33 (2000).
78. Yuste, L., Esparís-Ogando, A., Santos, E. & Pandiella, A. Overexpression of RasN17 Fails to Neutralize Endogenous Ras in MCF7 Breast Cancer Cells. Journal of Biochemistry 137, 731-739 (2005).
79. Olsson, P. et al. Uptake of a boronated epidermal growth factor-dextran conjugate in CHO xenografts with and without human EGF-receptor expression. Anti-Cancer Drug Design 13, 279-289 (1998).
80. Krug, A. W. et al. Human Epidermal Growth Factor Receptor-1 Expression Renders Chinese Hamster Ovary Cells Sensitive to Alternative Aldosterone Signaling. Journal of Biological Chemistry 277, 45892-45897 (2002).
81. Blagoev, B. et al. A proteomics strategy to elucidate functional protein-protein interactions applied to EGF signaling. Nature Biotechnology 21, 315-318 (2003).
82. Vieira, A. V., Lamaze, C. & Schmid, S. L. Control of EGF Receptor Signaling by Clathrin-Mediated Endocytosis. Science 274, 2086 (1996).
83. Hutchings, S. E. & Sato, G. H. Growth and Maintenance of HeLa Cells in Serum-Free Medium Supplemented with Hormones. Proceedings of the National Academy of Sciences of the United States of America 75, 901-904 (1978).

84. Stove, C. & Bracke, M. Roles for neuregulins in human cancer. Clinical and Experimental Metastasis 21, 665-684 (2005).
85. Wallasch, C. et al. Heregulin-dependent regulation of HER2/neu oncogenic signaling by heterodimerization with HER3. EMBO J. 14, 4267-4275 (1995).
86. Tan, M., Grijalva, R. & Yu, D. 1620-1625 (AACR, 1999).
87. Graus-Porta, D., Beerli, R. R., Daly, J. M. & Hynes, N. E. ErbB-2, the preferred heterodimerization partner of all ErbB receptors, is a mediator of lateral signaling. The EMBO Journal 16, 1647-1655 (1997).
88. Lenferink, A. E. et al. Differential endocytic routing of homo- and hetero-dimeric ErbB tyrosine kinases confers signaling superiority to receptor heterodimers. The EMBO Journal 17, 3385 (1998).
89. Moulder, S. L. et al. 8887-8895 (AACR, 2001).
90. Olayioye, M. A., Neve, R. M., Lane, H. A. & Hynes, N. E. The ErbB signaling network: receptor heterodimerization in development and cancer. EMBO J. 19, 3159-3167 (2000).
91. Adam, L. et al. Heregulin Regulates Cytoskeletal Reorganization and Cell Migration through the p21-activated Kinase-1 via Phosphatidylinositol-3 Kinase. Journal of Biological Chemistry 273, 28238-28246 (1998).
92. Arndt, K. M., Pelletier, J. N., Müller, K. M., Plückthun, A. & Alber, T. Comparison of In Vivo Selection and Rational Design of Heterodimeric Coiled Coils. Structure 10, 1235-1248 (2002).
93. Arndt, K. M., Müller, K. M. & Plückthun, A. Helix-stabilized Fv (hsFv) antibody fragments: substituting the constant domains of a Fab fragment for a heterodimeric coiled-coil domain. J. Mol. Biol. 312, 221-228 (2001).
94. Ferguson, K. M. et al. EGF activates its receptor by removing interactions that autoinhibit ectodomain dimerization. Molecular cell 11, 507-517 (2003).
95. Jura, N. et al. Mechanism for Activation of the EGF Receptor Catalytic Domain by the Juxtamembrane Segment. Cell 137, 1293-1307 (2009).
96. Macdonald-Obermann, J. L. & Pike, L. J. The Intracellular Juxtamembrane Domain of the Epidermal Growth Factor (EGF) Receptor Is Responsible for the Allosteric Regulation of EGF Binding. Journal of Biological Chemistry 284, 13570 (2009).
97. Red Brewer, M. et al. The Juxtamembrane Region of the EGF Receptor Functions as an Activation Domain. Molecular Cell 34, 641-651 (2009).
98. Liu, P. et al. Investigation of the dimerization of proteins from the epidermal growth factor receptor family by single wavelength fluorescence cross-correlation spectroscopy. Biophysical journal 93, 684-698 (2007).
99. Park, E., Baron, R. & Landgraf, R. Higher-Order Association States of Cellular ERBB3 Probed with Photo-Cross-Linkable Aptamers. Biochemistry 47, 11992-12005 (2008).
100. Szabo, A., Horváth, G., Szöll si, J. & Nagy, P. Quantitative characterization of the large-scale association of ErbB1 and ErbB2 by flow cytometric homo-FRET measurements. Biophysical Journal 95, 2086-2096 (2008).
101. Tao, R. H. & Maruyama, I. N. All EGF (ErbB) receptors have preformed homo- and heterodimeric structures in living cells. Journal of Cell Science 121, 3207 (2008).
102. Penuel, E., Schaefer, G., Akita, R. W. & Sliwkowski, M. X. Structural requirements for ErbB2 transactivation. Semin Oncol 28, 36-42 (2001).
103. Sorkin, A. & Goh, L. K. Endocytosis and intracellular trafficking of ErbBs. Experimental cell research 314, 3093-3106 (2008).
104. Haugh, J. M., Schooler, K., Wells, A., Wiley, H. S. & Lauffenburger, D. A. Effect of epidermal growth factor receptor internalization on regulation of the phospholipase C-gamma1 signaling pathway. J Biol Chem 274, 8958-8965 (1999).
105. Hendriks, B. S., Orr, G., Wells, A., Wiley, H. S. & Lauffenburger, D. A. Parsing ERK Activation Reveals Quantitatively Equivalent Contributions from Epidermal Growth Factor Receptor and HER 2 in Human Mammary Epithelial Cells. Journal of Biological Chemistry 280, 6157-6169 (2005).
106. Tamama, K., Fan, V. H., Griffith, L. G., Blair, H. C. & Wells, A. Epidermal Growth Factor as a Candidate for Ex Vivo Expansion of Bone Marrow-Derived Mesenchymal Stem Cells. Stem Cells 24, 686 (2006).
107. Gavrieli, Y., Sherman, Y. & Ben-Sasson, S. A. Identification of programmed cell death in situ via specific labeling of nuclear DNA fragmentation. Journal of cell Biology 119, 493-501 (1992).
108. Kumar, N., Wolf-Yadlin, A., White, F. M. & Lauffenburger, D. A. Modeling HER2 effects on cell behavior from mass spectrometry phosphotyrosine data. PLoS Comput Biol 3, e4 (2007).
109. Harms, B. D., Bassi, G. M., Horwitz, A. R. & Lauffenburger, D. A. Directional persistence of EGF-induced cell migration is associated with stabilization of lamellipodial protrusions. Biophysical journal 88, 1479-1488 (2005).
110. Xue, C. et al., Vol. 66 1418-1426 (AACR, 2006).
111. Feldner, J. C. & Brandt, B. H. Cancer cell motility—on the road from c-erbB-2 receptor steered signaling to actin reorganization. Experimental cell research 272, 93-108 (2002).

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All patents and patent publications references and other publications, including kit protocols that are recited in this application are incorporated in their entirety herein by reference. Their citation, however, is not an admission that they are prior art.

What is claimed is:

1. A method of controlling Her-3 receptor dimerization, comprising:
   contacting cells that express Her-3 receptors with a ligand dimer that comprises two Her-3 ligands and a linker in an amount effective to cause the dimerization of a Her-3 receptor pair.

2. The method of claim 1, wherein the cells express at least two types of Her receptors.

3. The method of claim 1, wherein the linker comprises a coiled coil domain.

4. The method of claim 3, wherein the linker further comprises peptide spacers.

5. The method of claim 4, wherein the peptide spacer is a 20 amino acid peptide.

6. The method of claim 1, wherein the linker comprises a water soluble flexible polymer that covalently links the two Her-3 ligands.

7. The method of claim 6, wherein the water soluble flexible polymer is polyethylene oxide (PEO), dextran, polyacrylic acid or polyacrylamide.

8. A ligand dimer, comprising two ligands, each of which is a Her-3 ligand, and a linker, wherein the ligand dimer causes dimerization of a Her-3 receptor.

9. A composition comprising the ligand dimer of claim 8, wherein the ligand dimer is attached to a substrate.

10. A composition comprising the ligand dimer of claim 8, wherein the composition further comprises a pharmaceutically acceptable carrier.

11. A method for assessing the ability of one or more ligand dimers to control dimerization of a Her-3 receptor pair, comprising:
    contacting cells that express a Her-3 receptor with one or more of the ligand dimers of claim 8, and
    determining whether or not dimerization of a Her-3 receptor pair occurred.

12. The ligand dimer of claim 8, wherein the linker comprises a coiled coil domain.

13. The ligand dimer of claim 12, wherein the linker further comprises peptide spacers.

14. The ligand dimer of claim 13, wherein the peptide spacer is a 20 amino acid peptide.

15. The ligand dimer of claim 8, wherein the linker comprises a water soluble flexible polymer that covalently links the two Her-3 ligands.

16. The ligand dimer of claim 15, wherein the water soluble flexible polymer is polyethylene oxide (PEO), dextran, polyacrylic acid or polyacrylamide.

* * * * *